US012753395B2

(12) United States Patent
Takeshita et al.

(10) Patent No.: US 12,753,395 B2
(45) Date of Patent: Oct. 6, 2026

(54) CELL CULTURE METHOD AND CELL CULTURE DEVICE USED WITH CELL CULTURE METHOD

(71) Applicant: YAMAGUCHI UNIVERSITY, Yamaguchi (JP)

(72) Inventors: Yukio Takeshita, Yamaguchi (JP); Susumu Fujikawa, Yamaguchi (JP); Kinya Matsuo, Yamaguchi (JP); Miwako Fujisawa, Yamaguchi (JP); Masaya Tamada, Yamaguchi (JP); Masashi Okamoto, Yamaguchi (JP); Takaya Shiota, Yamaguchi (JP); Tomohiro Hata, Yamaguchi (JP); Haruto Fukusako, Yamaguchi (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 609 days.

(21) Appl. No.: 18/304,305

(22) Filed: Apr. 20, 2023

(65) Prior Publication Data

US 2023/0313149 A1 Oct. 5, 2023

Related U.S. Application Data

(63) Continuation of application No. PCT/JP2021/039014, filed on Oct. 21, 2021.

(30) Foreign Application Priority Data

Oct. 23, 2020 (JP) ................................ 2020-178448

(51) Int. Cl.

| | |
|---|---|
| ***C12N 5/071*** | (2010.01) |
| ***C12M 1/00*** | (2006.01) |
| ***C12M 1/12*** | (2006.01) |
| ***C12M 3/00*** | (2006.01) |

(52) U.S. Cl.

CPC .......... *C12N 5/0697* (2013.01); *C12M 21/08* (2013.01); *C12M 23/38* (2013.01); *C12M 25/04* (2013.01); *C12N 2539/10* (2013.01)

(58) Field of Classification Search

None

See application file for complete search history.

(56) References Cited

U.S. PATENT DOCUMENTS

| | | | |
|---|---|---|---|
| 5,665,596 | A | 9/1997 | Mussi |
| 7,879,607 | B2 | 2/2011 | Crespi et al. |
| 9,267,101 | B2 | 2/2016 | Schmidt et al. |
| 11,447,752 | B2 | 9/2022 | Takeshita et al. |
| 2007/0269850 | A1 | 11/2007 | Crespi et al. |
| 2013/0267019 | A1 | 10/2013 | Schmidt et al. |
| 2019/0144832 | A1 | 5/2019 | Takeshita et al. |

FOREIGN PATENT DOCUMENTS

| | | | |
|---|---|---|---|
| EP | 2955220 | A1 | 12/2015 |
| JP | 2007-306925 | A | 11/2007 |
| JP | 5674953 | B2 | 2/2015 |
| RU | 2668157 | C1 | 9/2018 |
| WO | 2012/045368 | A1 | 4/2012 |
| WO | 2017/179375 | A1 | 10/2017 |

OTHER PUBLICATIONS

International Search Report issued in PCT/JP2021/039014 mailed on Dec. 28, 2021 with English Translation (5 pages).

Written Opinion of International Searching Authority issued in PCT/JP2021/039014 mailed on Dec. 28, 2021 with English Translation (7 pages).

Office Action issued in Japanese Patent Application No. 2022-557611 mailed on Oct. 31, 2025, with English Translation (12 pages).

Decision of Refusal issued in Japanese Patent Application No. 2022-557611 mailed on Mar. 17, 2026, with English Translation (7 pages).

Extended European Search Report issued in European Patent Application No. 21882912.5, dated Feb. 4, 2026 (9 pages).

Office Action issued in Chinese Patent Application No. 202180072115.X dated Jan. 28, 2026, with English Translation (28 pages).

Office Action issued in Chinese Patent Application No. 202180072115.X dated Jun. 6, 2026, with English Translation (23 pages).

*Primary Examiner* — Teresa E Knight

(74) *Attorney, Agent, or Firm* — Nakanishi IP Associates, LLC

(57) ABSTRACT

A cell culture method and a cell culture device used with the cell culture method allow mass-producing a three-layer blood-brain barrier (BBB) in vitro model including a vascular endothelial cell, a pericyte, and an astrocyte. A cell culture method enhances mass production of the three-layer BBB models. A cell culture method includes injecting a suspended cell culture medium into an outer surface of a porous membrane in a cell culture insert, seeding the cell culture medium with an astrocyte to culture the astrocyte, seeding the cell culture insert being inverted with a pericyte to culture the pericyte, seeding the cell culture insert with a temperature-sensitive vascular endothelial cell embedded in a temperature-sensitive gel to culture the vascular endothelial cell, and melting the temperature-sensitive gel.

7 Claims, 42 Drawing Sheets

CELL CULTURE METHOD AND CELL CULTURE DEVICE USED WITH CELL CULTURE METHOD

BACKGROUND OF INVENTION

Field of the Invention

The present invention relates to a technique for in vitro culture of cells forming a blood-brain barrier in vitro model (hereafter referred to as a BBB model), or particularly relates to a cell culture method that allows mass production of three-layer BBB models including a vascular endothelial cell, a pericyte, and an astrocyte, and to a cell culture device used with the cell culture method. In vitro is Latin for "within the glass" and typically indicates the state of a part of a living organism being extracted or isolated from the living organism.

Background Art

A blood-brain barrier (BBB) is anatomically a brain capillary vessel, and includes, for example, brain-derived vascular endothelial cells, pericytes, and astrocytes. Pericytes surrounding the vascular endothelial cells control differentiation or growth of vascular endothelial cells. Astrocytes provide nutrients to neurons and immediately remove excess ions or neurotransmitters to protect neurons.

The BBB regulates the exchange of substances between the blood and brain tissue fluid. This function maintains neuron homeostasis. However, this function can obstruct development of preventive or therapeutic drugs for central nervous diseases. For example, drugs to act on the central nervous system may be actually prevented by the BBB from crossing into the brain and cannot produce expected effects. In addition, drugs unexpected to cross into the brain may cross the BBB and adversely affect the central nervous system.

No rules have been defined for substances that cross the BBB. Thus, the development of preventive or therapeutic drugs for central nervous diseases involves screening using a BBB model.

The inventors have successfully developed a model that accurately reproduces an anatomical architecture of the BBB. Thus, the level of research in drug screening has greatly increased in recent days.

This BBB model includes layers of an astrocyte and a pericyte holding a porous membrane in between, and a vascular endothelial cell layer directly in contact with the pericyte. This BBB model has been manually fabricated by skilled researchers. The fabrication involves special techniques, and thus the BBB model is not mass-producible.

Example techniques associated with fabrication of the BBB model include a device named a cell culture insert described in Patent Literature 1, which is directed to coculturing cells on the two surfaces of a porous membrane.

The cell culture device described in Patent Literature 1 includes an outer pipe body having a lower end to which a porous film is attached, a complementary pipe body that fits to the outer diameter of the lower end of the outer pipe body, and a hanging component that includes at least one flange extending laterally from an upper end and has the outer diameter either entirely or partially fitting to the inner diameter of the outer pipe body. In a first stage, the outer pipe body is coupled to the complementary pipe body to form an independent insert for first cell culture. In a second stage, the outer pipe body is disengaged from the complementary pipe body and attached to the hanging component for second cell culture.

In this cell culture device, the complementary pipe body is coupled to the lower end of the outer pipe body, and both pipe bodies are inverted to form a cell culture chamber. In the cell culture chamber, cells are sown onto the outer surface of a membrane protruding in the complementary pipe body (first cell seeding). After an appropriate culture period, the coupled pipe bodies are inverted, the hanging component is coupled to the outer pipe body, and then the complementary pipe body is removed. Thus, a hanging insert is obtained. The hanging insert is placed in a well in a cell culture plate to perform second cell seeding on an inner surface of the membrane protruding upward.

Thus, the cell culture device with the above structure performs two separate stages of cell seeding on the outer surface and the inner surface of the membrane to coculture the cells on the two surfaces of the membrane.

CITATION LIST

Patent Literature

Patent Literature 1: Japanese Patent No. 5674953

SUMMARY OF INVENTION

Technical Problem

The device described in Patent Literature 1 can fabricate a cell culture model including different types of cell layers on the two surfaces of a porous membrane, but involves sequential manual operations for forming the cell culture chamber and the hanging insert, and is thus unsuitable for mass production of cell culture models. Thus, when the cell culture device described in Patent Literature 1 is used for fabricating a BBB model, mass production of the BBB model may fail.

In response to the above circumstances, one aspect of the present invention is directed to a cell culture method for mass-producing a three-layer BBB model including a vascular endothelial cell, a pericyte, and an astrocyte, and to a cell culture device used with the cell culture method. Another aspect of the present invention is directed to a cell culture method for enhancing mass production of BBB models including layers of the three cells by retaining the laminate of three cells for a long time.

Solution to Problem

A cell culture device according to a first aspect of the present invention includes a plurality of pairs of upper cell culture chambers and lower cell culture chambers. Each of the plurality of pairs is defined by an inner wall divided by a porous membrane. The inner wall is tubular. The upper cell culture chambers are coupled and integrated, and the lower cell culture chambers are coupled and integrated. The porous membrane has two surfaces to which a living organism material is to be fixed. The cell culture device includes a cell culture chamber cover that simultaneously closes at least the integrated upper cell culture chambers or the integrated lower cell culture chambers.

The cell culture device with the above structure includes the cell culture chamber cover covering an opening end of the cell culture chambers. A cell culture medium injected into the cell culture chambers or cells sown into the cell culture chambers are thus less likely to leak from the cell culture chambers during handling.

At least the upper cell culture chambers or the lower cell culture chambers are closed by the cell culture chamber cover. This allows a living organism material to be cultured on the two surfaces of the porous membrane without the two surfaces being closed. More specifically, either of the upper cell culture chambers or the lower cell culture chambers including the living organism material fixed on the upper surface (first surface) of the porous membrane are closed first and are inverted to face downward for the other cell culture chambers to face upward. The living organism material is then fixed to the back surface (second surface) of the porous membrane, and the cell culture chambers remain uninverted after the operation.

Simultaneously closing at least the integrated upper cell culture chambers or the integrated lower cell culture chambers refers to simultaneously closing all the integrated cell culture chambers, and simultaneously closing each cell culture chambers included in the integrated cell culture chambers.

A cell culture device according to a second aspect of the present invention is the cell culture device according to the first aspect of the present invention further including a cell culture plate having a plurality of first through-holes each being the inner wall, and a bottom surface receiving a sheet including the porous membrane to cover the plurality of first through-holes, a first bottom cover placeable on the bottom surface of the cell culture plate and including an open top and a bottom board having a plurality of second through-holes each being the inner wall together with a corresponding first through-hole of the plurality of first through-holes, and a second bottom cover being the cell culture chamber cover placeable on the bottom board in the first bottom cover. The plurality of second through-holes align with the plurality of first through-holes in a plan view of the first bottom cover placed on the bottom surface of the cell culture plate.

In the second aspect, in addition to the effects of the first aspect, when an astrocyte is sown into the second through-holes together with the cell culture medium after the first bottom cover is placed on the bottom surface with the cell culture plate being inverted, the second through-holes have their inner walls preventing leakage of the cell culture medium and the astrocyte, and thus facilitate culture of the astrocyte on the outer surface of the porous membrane. When the second bottom cover is placed on the first bottom cover, and a pericyte and a vascular endothelial cell are sown with the cell culture medium into the first through-holes in the cell culture plate after the cell culture plate is inverted together with the first bottom cover and the second bottom cover, the first through-holes have their inner walls preventing leakage of the cell culture medium, the pericyte, and the vascular endothelial cell, and thus facilitate culture of the pericyte and the vascular endothelial cell on the inner surface of the porous membrane. The cell culture plate with the first bottom cover and the second bottom cover placed on the cell culture plate serves as a microplate.

A cell culture device according to a third aspect of the present invention is the cell culture device according to the first aspect of the present invention further including a first inner wall of a cell culture insert having one end closed by the porous membrane and being the inner wall of each of the upper cell culture chambers and the lower cell culture chambers, a cell culture plate having a plurality of through-holes each receiving the cell culture insert and being the inner wall of each of the upper cell culture chambers and the lower cell culture chambers, and a planar first plate cover and a planar second plate cover each being the cell culture chamber cover and placeable over two surfaces of the cell culture plate to cover the plurality of through-holes each receiving the cell culture insert.

In the third aspect, in addition to the effects of the first aspect, after the first plate cover is placed over the upper surface of the cell culture plate having the through-holes receiving the cell culture inserts with the bottom facing downward, the cell culture plate and the first plate cover are inverted, and the astrocyte is sown with the cell culture medium into the through-holes in the cell culture plate. Thus, the through-holes in the cell culture plate have their inner walls preventing leakage of the cell culture medium and the astrocyte and facilitate culture of the astrocyte on the outer surface of the porous membrane. In addition, when the second plate cover is placed over the surface of the cell culture plate uncovered with the first plate cover, and the cell culture plate is inverted together with the first plate cover and the second plate cover, the through-holes in the cell culture plate hold the cell culture inserts with the bottoms facing downward. This facilitates seeding the cell culture inserts with the cell culture medium, the pericyte, and the vascular endothelial cell, or culture of the vascular endothelial cell and the pericyte in the cell culture inserts. In addition, the cell culture plate with the second plate cover placed over the cell culture plate serves as a microplate.

A cell culture device according to a fourth aspect of the present invention is the cell culture device according to the first aspect of the present invention further including a membrane holder being one of the plurality of pairs of upper cell culture chambers and lower cell culture chambers and including a second inner wall having one end closed by the porous membrane and being the inner wall, a plate including a planar first base, a plurality of first through-holes in the planar first base, and a plurality of first cylinders extending perpendicularly to one surface of the planar first base, being continuous with the plurality of first through-holes, receiving the membrane holder inside, and each being the inner wall together with a corresponding first through-hole of the plurality of first through-holes, a plate cover including a planar second base and a plurality of first protrusions on one surface of the planar second base to simultaneously fit into the plurality of first cylinders, and being the cell culture chamber cover to cover the plurality of first through-holes receiving the membrane holder inside, a spacer cover including a planar third base and a plurality of second protrusions on one surface of the planar third base to simultaneously fit into the plurality of first cylinders, and being the cell culture chamber cover to cover the plurality of first through-holes receiving the membrane holder inside, and a spacer including a planar fourth base and a plurality of second through-holes, being as many as the plurality of first through-holes and each being the inner wall, in the planar fourth base. The spacer includes a plurality of second cylinders extending continuously with the plurality of second through-holes and perpendicularly to one surface of the planar fourth base. The plurality of second cylinders defines the upper cell culture chambers and lower cell culture chambers together with the plurality of first cylinders, are simultaneously received in the plurality of first cylinders, and are each the inner wall together with a corresponding second through-hole of the plurality of second through-holes. The cell culture device includes a pusher including a planar push plate and a plurality of push portions extending perpendicularly to one surface of the planar push plate to be simultaneously received in the plurality of first through-holes.

In the fourth aspect, in addition to the effects of the first aspect, when the membrane holder is placed at upper ends of the second cylinders in the spacer, the first cylinders in the plate are fitted to the second cylinders in the spacer, and the spacer cover is attached to the spacer to fit the second protrusions to the first cylinders, the spacer cover prevents leakage of the cell culture medium injected into the second cylinders in the spacer through the first through-holes in the plate. In addition, the second cylinders in the spacer hold the membrane holder. This facilitates culture of the astrocyte on the inner surface of the porous membrane.

After the cell culture medium in the second cylinders in the spacer is removed, the spacer cover is attached to the spacer to fit the first protrusions to the first cylinders, the spacer is inverted together with the plate cover and the spacer cover. When the spacer cover is removed, and then the pericyte is sown with the cell culture medium into the second cylinders in the spacer, the second cylinders in the spacer have their inner walls preventing leakage of the cell culture medium and the pericyte and facilitate culture of the pericyte on the outer surface of the porous membrane.

The plate cover, the spacer cover, and the spacer are removed from the plate. Each push portion of the pusher is placed in the corresponding first through-hole in the plate, and then the pusher is placed closer to the plate to place the push plate into contact with the first base of the plate. Thus, the push portion pushes the membrane holder out of the corresponding first cylinder.

After the vascular endothelial cell sheet is laid on the upper surfaces of the membrane holders pushed out of the first cylinders in the plate, the vascular endothelial cell sheet is punched out with the sleeves from above and the membrane holders are placed at the distal ends of the sleeves by pushing the sleeves into the membrane holders to integrate the membrane holders and the sleeves together. Thus, a cell culture insert including three cell layers of the pericyte, the astrocyte, and the vascular endothelial cell sheet at the bottom is obtained.

A cell culture device according to a fifth aspect of the present invention is the cell culture device according to the first aspect of the present invention further including a membrane holder being one of the plurality of pairs of upper cell culture chambers and lower cell culture chambers and including a third inner wall having one end closed by the porous membrane and being the inner wall, a plate being one of the plurality of pairs of upper cell culture chambers and lower cell culture chambers and including a planar base and a plurality of through-holes located in the planar base, each receiving the membrane holder inside, and each being the inner wall of each of the upper cell culture chambers and the lower cell culture chambers, two planar plate covers each being the cell culture chamber cover and placeable on the plate to cover the plurality of through-holes each receiving the membrane holder inside, and a pusher including a planar push plate and a plurality of push portions extending perpendicularly to one surface of the planar push plate to be simultaneously received in the plurality of through-holes.

In the fifth aspect, in addition to the effects of the first aspect, when the plate cover is attached to the lower surface of the plate, each membrane holder is placed in the corresponding through-hole to have the outer surface of the porous membrane facing downward, and then the cell culture medium is injected into the through-holes in the plate. The through-holes in the plate have their inner walls preventing leakage of the cell culture medium and facilitate culture of the astrocyte on the inner surface of the porous membrane.

When another plate cover is attached to the upper surface of the plate, the plate is inverted, and then the previously attached plate cover is removed from the plate, the membrane holder is inverted in the through-holes of the plate and the outer surface of the porous membrane faces upward. Thus, when the pericyte is sown into the through-holes in the plate, the pericyte is easily cultured on the inner surface of the porous membrane.

In addition, when the other plate cover is removed from the plate, the push portions of the pusher are received in the through-holes in the plate, and then the pusher is placed toward the plate to place the push plate into contact with the base of the plate, the push portions push the membrane holders out of the cylinders.

After the vascular endothelial cell sheet is laid on the upper surfaces of the membrane holders pushed out of the cylinders in the plate, the vascular endothelial cell sheet is punched out with the insert bodies from above, and the membrane holders are placed at the distal ends of the insert bodies by pushing the insert bodies into the membrane holders to integrate the membrane holders and the insert bodies. Thus, a cell culture insert including three cell layers of the pericyte, the astrocyte, and the vascular endothelial cell sheet at the bottom is obtained.

A cell culture device according to a sixth aspect of the present invention is the cell culture device according to the fifth aspect of the present invention in which the plate includes, on two surfaces of the planar base, a plurality of first protrusions and a plurality of second protrusions being continuous with the plurality of through-holes and surrounding the plurality of through-holes in a plan view of the planar base. The two plate covers each include, on one surface of the plate cover, a plurality of first cylinders to simultaneously fit to the plurality of first protrusions or the plurality of second protrusions. The pusher includes a plurality of second cylinders shorter than the plurality of push portions on one surface of the push plate. The plurality of second cylinders surround the plurality of push portions. The plurality of second cylinders simultaneously fit to the plurality of first protrusions and the plurality of second protrusions.

In the sixth aspect, the plurality of first protrusions and the plurality of second protrusions in the plate, the plurality of first cylinders in the plate cover, and the plurality of second cylinders in the pusher correspond respectively to generic concepts of first annular protrusions **14*b* and second annular protrusions 14*c* in a plate 14, short cylinders included in a holder 15*b* in a plate cover 15, and short cylinders included in a holder 17*b* in a pusher 17 described later in an embodiment with reference to FIGS. 11A, 11C, and 11**F.

In the sixth aspect, in addition to the effects of the fifth aspect, fitting each first cylinder in the plate cover to the corresponding first or second protrusion in the plate enhances adhesion of the plate cover to the plate, and fitting each second cylinder in the pusher to the corresponding first or second protrusion in the plate allows accurate positioning of the pusher with respect to the plate.

A cell culture device according to a seventh aspect of the present invention is the cell culture device according to the first aspect of the present invention further including a plurality of cell culture inserts being the upper cell culture chambers and the lower cell culture chambers and each including a fourth inner wall having one end closed by the porous membrane and being the inner wall, a cell culture case including the upper cell culture chambers and the lower cell culture chambers and including an open top and a bottom board having a plurality of through-holes each being the inner wall and receiving the plurality of cell culture inserts, an insert holder that holds the plurality of cell culture inserts while allowing the plurality of cell culture inserts to be simultaneously received in the plurality of through-holes in cell culture case, and a case lid being the cell culture chamber cover that covers the open top of the cell culture case.

In the seventh aspect, in addition to the effects of the first aspect, after the cell culture case is placed with the multiple cell culture inserts being held by an insert holder facing down and the bottoms of the cell culture inserts protruding through the respective through-holes, the cell culture medium is injected into the cell culture case. The cell culture case traps the cell culture medium without allowing leakage of the cell culture medium to facilitate culture of the astrocyte on the outer surface of the porous membrane.

After the case lid is attached to the top of the cell culture case, and the cell culture case is inverted together with the insert holder, the case lid prevents leakage of the cell culture medium from the cell culture case, and the multiple cell culture inserts are simultaneously inverted to face upward. Thus, when sown into the cell culture inserts, the pericyte is easily cultured on the inner surface of the porous membrane.

When the cell culture inserts including three cell layers including the vascular endothelial cell, the pericyte, and the astrocyte at the bottom are obtained by sowing and culturing the vascular endothelial cell in the cell culture inserts, the cell culture inserts are integrated by the insert holder to facilitate transfer of the inserts to the wells in the microplate.

A cell culture method according to an eighth aspect of the present invention is a method for fabricating a three-layer blood-brain barrier in vitro model including a vascular endothelial cell, a pericyte, and an astrocyte using a plurality of pairs of upper cell culture chambers and lower cell culture chambers. Each of the plurality of pairs is defined by an inner wall divided by a porous membrane. The inner wall is tubular. The porous member has two surfaces to which a living organism material is to be fixed. The method includes seeding, with the astrocyte, a first surface of the two surfaces of the porous membrane facing upward, culturing the astrocyte, simultaneously closing upper end openings of the plurality of pairs of upper cell culture chambers and lower cell culture chambers, simultaneously inverting the plurality of pairs of upper cell culture chambers and lower cell culture chambers to seed a second surface of the two surfaces of the porous membrane with the pericyte, culturing the pericyte, laying a sheet of the vascular endothelial cell on the second surface of the porous membrane, and culturing the vascular endothelial cell.

In embodiments of the present invention, the process of culturing the astrocyte, the pericyte, and the vascular endothelial cell and the process of injecting the cell culture medium into the cell culture inserts are described as separate processes. However, depending on the structure of the cell culture device, the cell culture inserts used for culturing the astrocyte may be used for culturing the pericyte or the vascular endothelial cell to eliminate additional injection of the cell culture medium into the cell culture inserts. Thus, in the eighth and ninth aspects of the present invention, the process of culturing the astrocyte, the pericyte, and the vascular endothelial cell includes either a process of using the cell culture medium injected into the cell culture inserts or a process of additionally injecting the cell culture medium into the cell culture inserts.

The method according to the eighth aspect includes a process of simultaneously inverting the multiple pairs of cell culture chambers with the upper end openings of the cell culture chambers being simultaneously closed. Thus, the cell culture medium injected into the cell culture chambers or the seeded cells are prevented from leaking from the cell culture chambers during handling.

A cell culture method according to a ninth aspect of the present invention is the cell culture method according to the eighth aspect of the present invention in which the vascular endothelial cell is temperature sensitive and stops growing at a temperature. The cell culture method includes, instead of laying the sheet of the vascular endothelial cell on the second surface of the porous membrane, seeding the second surface of the porous membrane with the vascular endothelial cell embedded in a temperature-sensitive gel, and melting the temperature-sensitive gel after culturing the vascular endothelial cell.

In the ninth aspect, in addition to the effects of the eighth aspect, melting of the temperature-sensitive gel completes precise laminate of the astrocyte, the pericyte, and the vascular endothelial cell, and the laminate of the three cells is maintained until the temperatures of these cells are lowered to the temperature at which cell growth is started.

Advantageous Effects

In the structure according to the first aspect, the multiple pairs of upper cell culture chambers and lower cell culture chambers each divided by the porous membrane are coupled and integrated, and at least the integrated upper cell culture chambers or the integrated lower cell culture chambers are closed by the cell culture chamber cover. Thus, the cell culture medium injected into the cell culture chambers or the seeded cells can be simultaneously handled without leaking when being inverted during handling. Thus, a handling device can efficiently invert the porous membrane or transfer fabricated BBB models into the wells in the microplate. The handling device can also handle the multiple cell culture chambers with no time difference and thus can homogeneously culture the cells between the cell culture chambers.

In addition to the effects of the first aspect, the structure according to the second aspect uses the cell culture plate directly as a microplate without using the cell culture inserts. Thus, compared with the method using the cell culture inserts or the microplate, the structure according to the second aspect enhances mass production of three-layer BBB models including the vascular endothelial cell, the pericyte, and the astrocyte.

In addition to the effects of the first aspect, the structure according to the third aspect reduces the spill of the cell culture medium and the astrocyte from the outer surface of the porous membrane and thus can efficiently form the cell layer of the astrocyte on the outer surface. When the cell culture plate receiving the cell culture inserts in the multiple through-holes is inverted, the porous membranes in all the cell culture inserts are inverted simultaneously. Thus, the astrocyte and pericyte cell layers are formed on the two surfaces of the porous membrane in a short time. Thus, the structure according to the third aspect allows efficient fabrication of three-layer BBB models including a vascular endothelial cell, a pericyte, and an astrocyte.

In the structure according to the fourth aspect, the multiple porous membranes and the membrane holders simultaneously undergo inversion of the porous membranes, removal of the membrane holders from the through-holes in the plate, and placement of the vascular endothelial cell over the pericyte. Thus, in addition to the effects of the first aspect, the structure according to the fourth aspect can fabricate multiple BBB models in a short time.

In the structure according to the fifth aspect, the multiple porous membranes and the membrane holders simultaneously undergo inversion of the porous membrane used to culture the astrocyte and the pericyte on the two surfaces of the porous membrane, removal of the membrane holders from through-holes in the plate, and placement of the vascular endothelial cell over the pericyte. Thus, in addition to the effects of the first aspect, the structure according to the fifth aspect can fabricate multiple BBB models in a short time.

In addition to the effects of the fifth aspect, in the structure according to the sixth aspect, the first cylinders enhance adhesion of the plate cover to the plate and thus effectively prevent leakage of the cell culture medium injected into the through-holes between the plate and the plate cover. In the structure according to the sixth aspect, the second cylinders accurately position the pusher with respect to the plate, and thus the plate and the pusher are less likely to be broken.

The structure according to the seventh aspect allows inversion of the cell culture inserts integrated together and transfer of the cell culture inserts to the wells in the microplate. Thus, in addition to the effects of the first aspect, the structure according to the seventh aspect can fabricate multiple BBB models in a short time.

The structure according to the eighth aspect prevents leakage of the cell culture medium injected into the cell culture chambers or the sown cells during handling. Thus, multiple pairs of cell culture chambers can be efficiently inverted simultaneously using, for example, the handling device. Thus, the structure according to the eighth aspect enhances mass production of three-layer BBB models including a vascular endothelial cell, a pericyte, and an astrocyte.

In addition to the effects of the eighth aspect, the structure according to the ninth aspect eliminates preparation of the vascular endothelial cell sheet and thus can eliminate the process of forming the cell sheet. Thus, the structure according to the ninth aspect can enhance mass production of BBB models including the three cell layers.

DETAILED DESCRIPTION

Figure 1A:
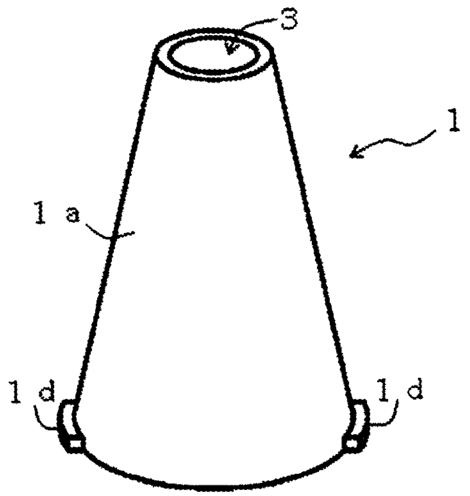
FIG. 1A is an external perspective view of a cell culture insert.

A cell culture method according to one or more embodiments of the present invention and a cell culture device used with the cell culture method are described with reference to FIGS. 1A to 42C. The components included in the cell culture device according to one or more embodiments of the present invention are all formed from plastics. The components described once are denoted with the same reference numerals without being described redundantly. Although the structure according to one or more embodiments includes a microplate having twelve wells, the microplate may have more or fewer wells. For example, the operations and effects of the present invention described below are similarly applicable to the microplate having 384 wells. Although a temperature-sensitive gel that melts at 37° C. is described below as an example, the temperature-sensitive gel may melt at a temperature other than 37° C. at which a vascular endothelial cell stops growing.

First Embodiment

Figure 1B:
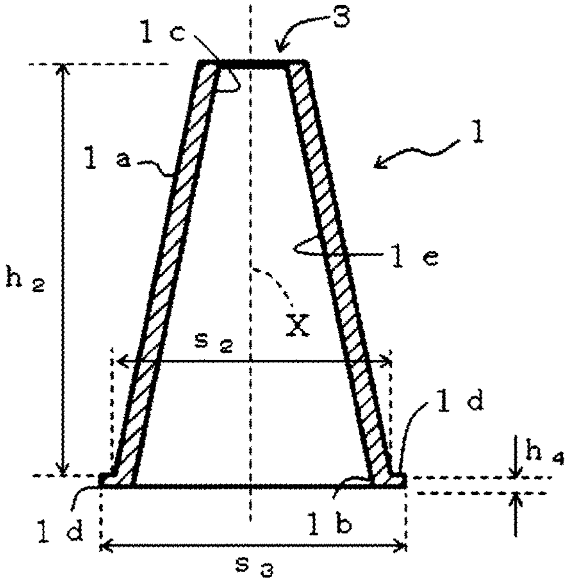
FIG. 1B is a longitudinal sectional view of the cell culture insert.
Figure 1C:
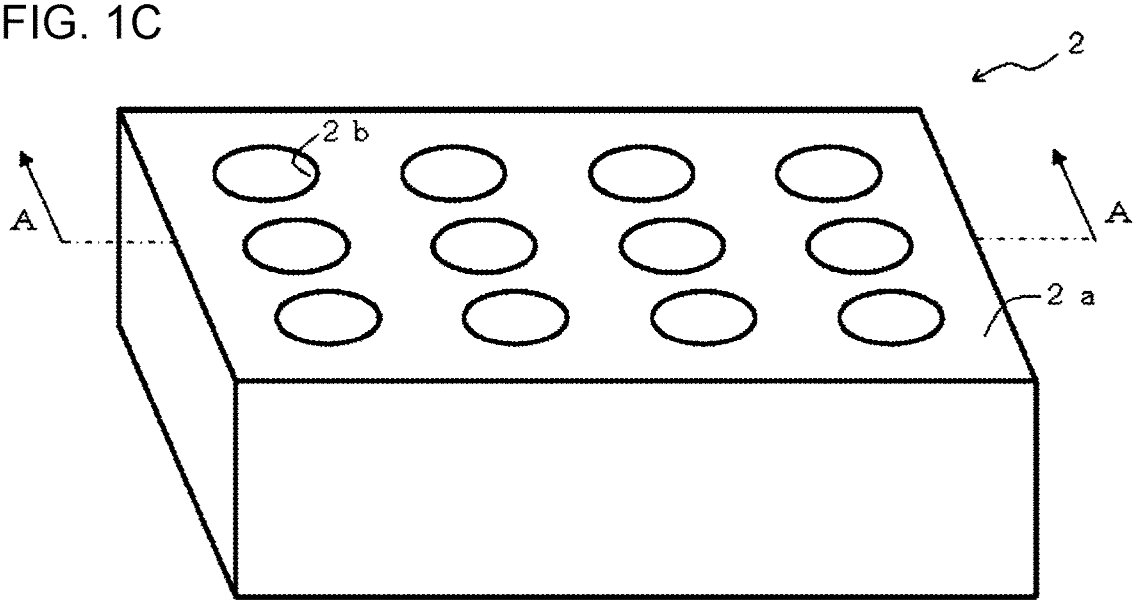
FIG. 1C is an external perspective view of a microplate.
Figure 1D:
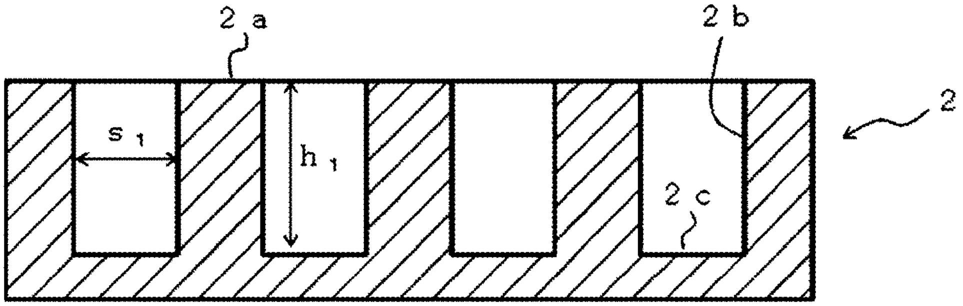
FIG. 1D is a cross-sectional view taken along line A-A as viewed in the direction indicated by arrows in FIG. 1C.

A cell culture device according to a first embodiment of the present invention will now be described with reference to FIGS. 1A to 1D. FIG. 1A is an external perspective view of a cell culture insert. FIG. 1B is a longitudinal sectional view of the cell culture insert. FIG. 1C is an external perspective view of a microplate. FIG. 1D is a cross-sectional view taken along line A-A as viewed in the direction indicated by arrows in FIG. 1C. To avoid complexity in the drawings, a single well alone is denoted with the reference numeral in FIGS. 1C and 1D.

As shown in FIGS. 1A to 1D, the cell culture device according to the present embodiment is placed in each well 2*b* in a microplate 2 being a circular bottomed hole to perform biochemical analysis or clinical testing using the microplate 2. The cell culture device includes a cell culture insert 1 having a flared side surface 1*a*.

The cell culture insert 1 includes a pair of flanges 1*d* located opposite to each other on the outer surface of an end adjacent to a large-diameter opening 1*b*, and a polycarbonate porous membrane 3 placed on the bottom inner surface to close a small-diameter opening 1*c*. The two surfaces of the porous membrane 3 allow a living organism material to be fixed on the surfaces. The microplate 2 is a rectangular prism with twelve (3 columns by 4 rows) wells 2*b* in an upper surface 2*a*.

The porous membrane 3 has pores with diameters of about 1 to 3 μm to allow a cell culture medium (described later) to pass through them. The porous membrane 3 is fixed to the cell culture insert 1 through thermal bonding.

An inner diameter $s_1$ (refer to FIG. 1D) of each well 2*b* is larger than an outer diameter $s_2$ (refer to FIG. 1B) of a side surface 1*a* in a portion with the pair of flanges 1*d*, and smaller than a distance $s_3$ (refer to FIG. 1B) between the outermost surfaces of the pair of flanges 1*d*. A depth $h_1$ (refer to FIG. 1D) of the well 2*b* is larger than a distance $h_2$ (refer to FIG. 1B) along a central axis X from the end face of the side surface 1*a* adjacent to the small-diameter opening 1*c* to the portion including the pair of flanges 1*d*. More specifically, the microplate 2 receives a portion of the cell culture insert 1 other than the portion with the pair of flanges 1*d* in the well 2*b* while spacing the outer surface of the porous membrane 3 from a bottom surface 2*c* (refer to FIG. 1D) of the well 2*b* and while allowing the pair of flanges 1*d* to be hooked on the edge of the well 2*b* (refer to FIG. 4A). Each cell culture insert 1 including a fourth inner wall 1*e* used as the inner wall of a cell culture chamber is used as the cell culture chamber below.

A cell culture method according to one or more embodiments of the present invention for fabricating three-layer BBB models each including a vascular endothelial cell, a pericyte, and an astrocyte using the cell culture device according to the present embodiment will now be described with reference to FIGS. 2 to 4B.

Figure 2:
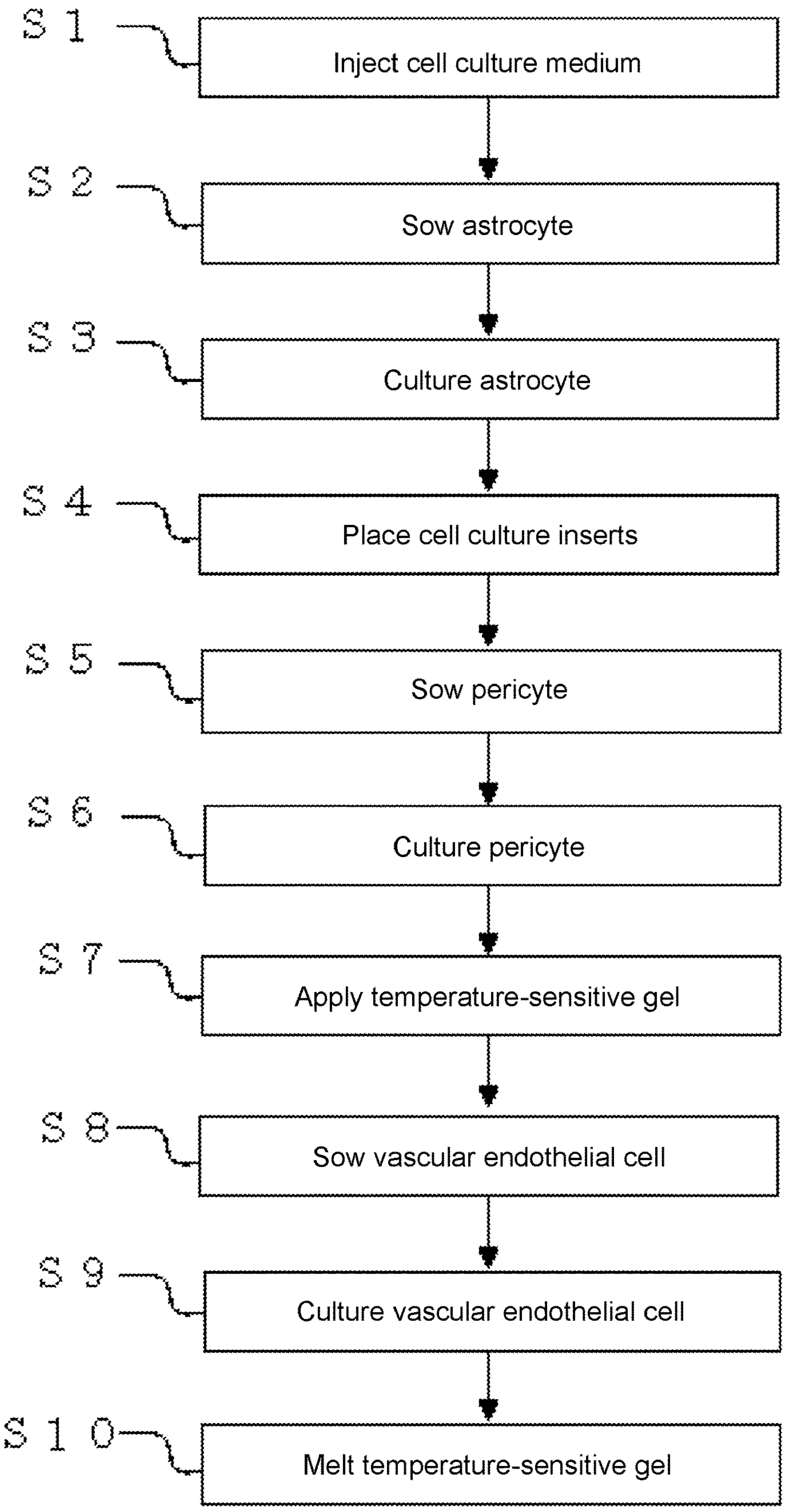
FIG. 2 is a flowchart of a cell culture method according to a first embodiment of the present invention.
Figure 3A:
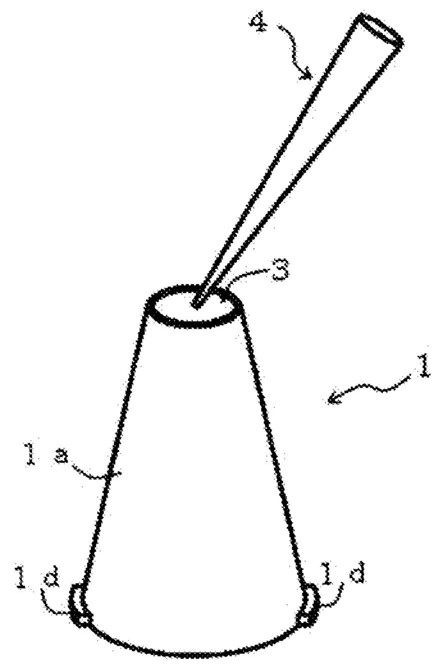
FIGS. 3A and 3B are diagrams of the cell culture insert having the outer surface of a porous membrane into which a cell culture medium is injected.
Figure 3B:
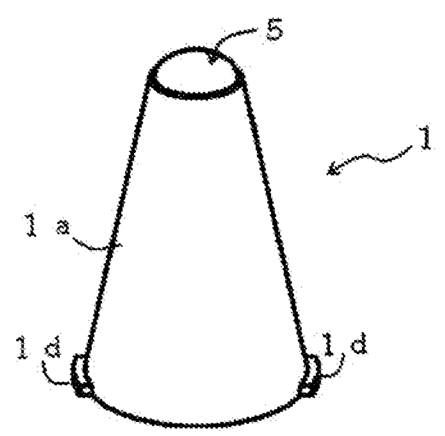
Figure 3C:
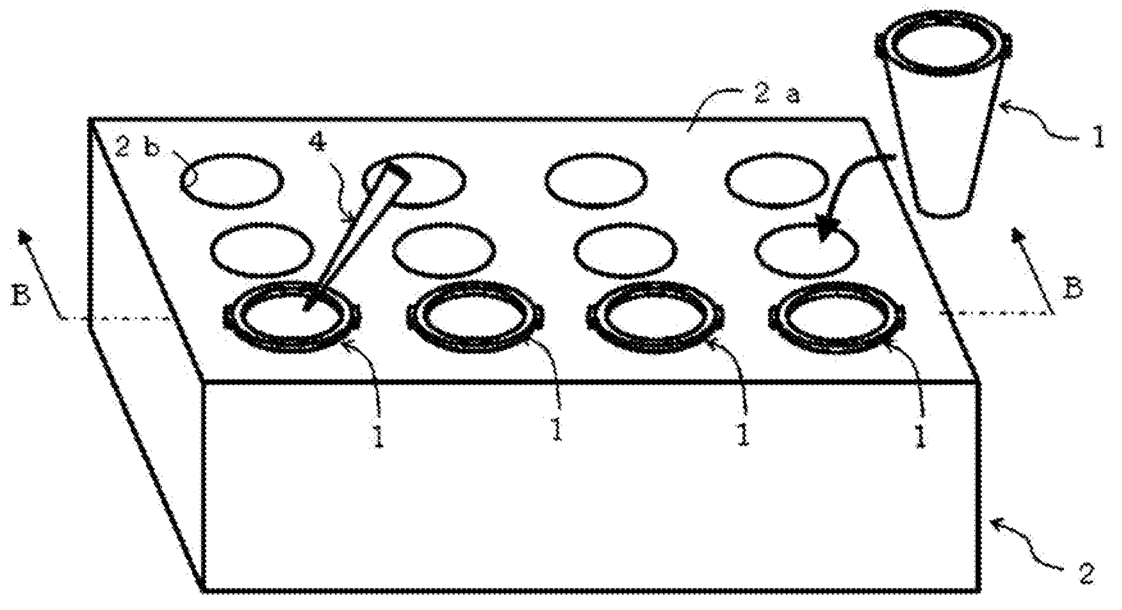
FIG. 3C is a diagram of the cell culture inserts placed in wells in the microplate seeded with cells.
Figure 4A:
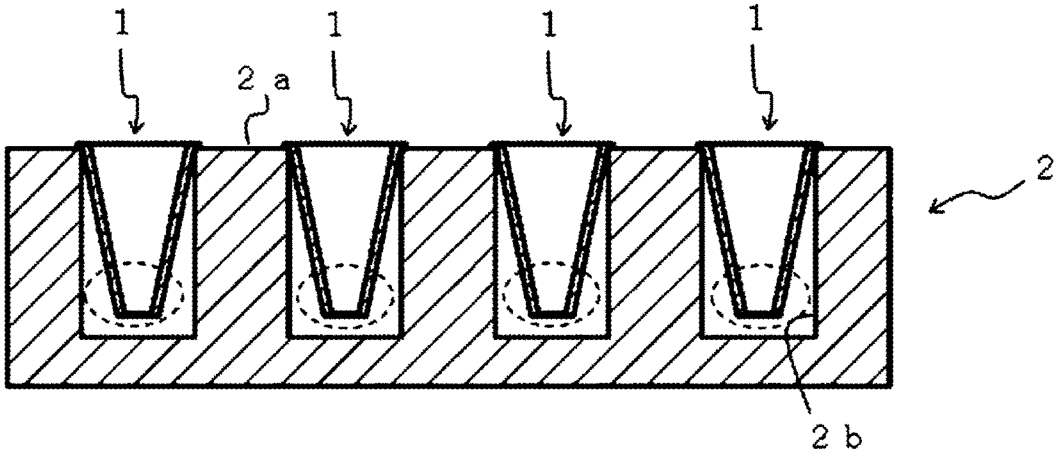
FIG. 4A is a cross-sectional view taken along line B-B as viewed in the direction indicated by arrows in FIG. 3C.
Figure 4B:
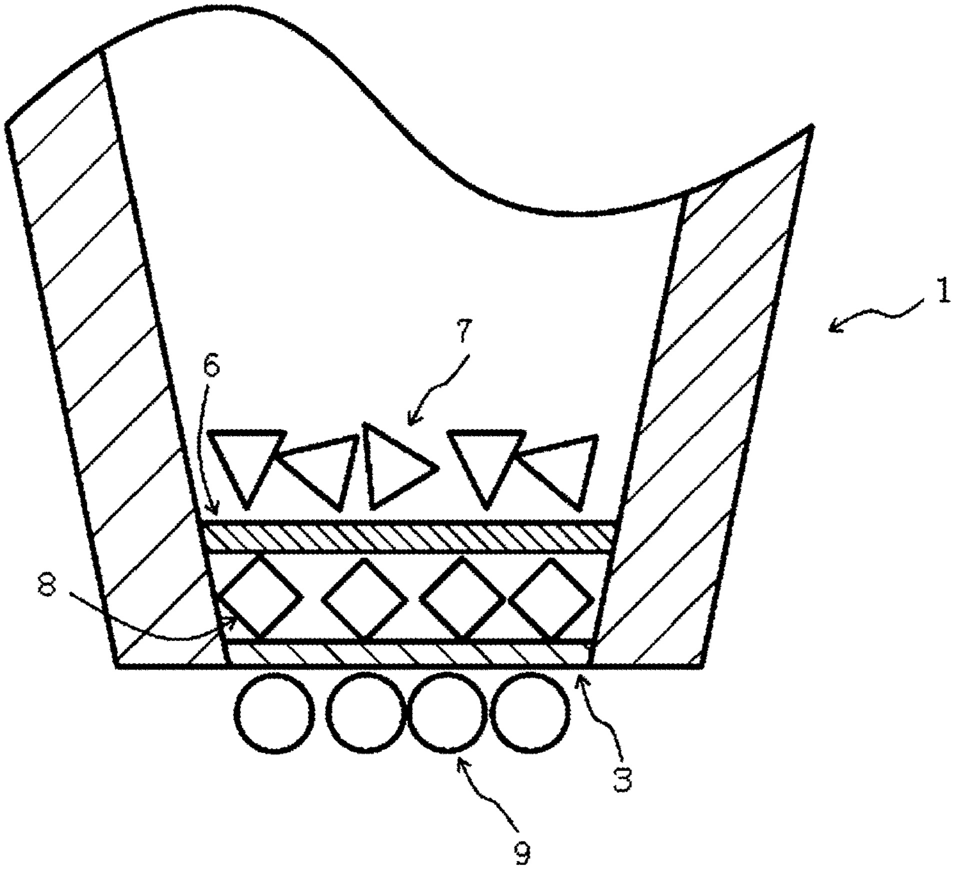
FIG. 4B is an enlarged view of one of the portions encircled with the dotted lines in FIG. 4A.

FIG. 2 is a flowchart of a cell culture method according to the first embodiment of the present invention. FIGS. 3A and 3B are diagrams of the cell culture insert having the outer surface of a porous membrane into which a cell culture medium is injected, and FIG. 3C is a diagram of the cell culture inserts placed in wells in the microplate seeded with cells. FIG. 4A is a cross-sectional view taken along line B-B as viewed in the direction indicated by arrows in FIG. 3C, and FIG. 4B is an enlarged view of one of the portions encircled with the dotted lines in FIG. 4A.

To avoid complexity in the drawings, in FIGS. 3C and 4A, a single well alone is denoted with the reference numeral, and four of twelve wells included in the microplate receive the cell culture inserts in FIG. 3C.

As shown in FIG. 3A, the cell culture insert 1 is first placed while facing down (having the bottom located above), and a suspended cell culture medium 5 is injected into the outer surface of the porous membrane 3 using a pipette 4 (step S1 in FIG. 2). As shown in FIG. 3B, the cell culture medium 5 then rises in a substantially hemispherical shape on the outer surface of the porous membrane 3 without passing through the porous membrane 3 due to surface tension, and is seeded with the astrocyte (step S2 in FIG. 2). The astrocyte is cultured for several days until forming into a layer with the temperature of the cell culture medium 5 maintained at, for example, 33° C. (step S3 in FIG. 2).

The cell culture insert 1 inverted from the position shown in FIG. 3B is placed in the well 2*b* in the microplate 2 filled with the cell culture medium 5 as shown in FIGS. 3C and 4A (step S4 in FIG. 2). Thereafter, a pericyte is sown into the cell culture insert 1 using the pipette 4 (step S5 in FIG. 2), and cultured for several days until forming into a layer with the temperature inside the cell culture insert 1 maintained at, for example, 33° C. (step S6 in FIG. 2). When the pericyte grows into a layer, the cell culture medium 5 is removed.

Thus, the astrocyte formed into a layer on the outer surface of the porous membrane 3 has cell projections extending through pores in the porous membrane 3 to a position near the pericyte formed on the inner surface of the porous membrane 3.

Subsequently, a temperature-sensitive gel 6 (e.g., Gelatin LS-250 from Nitta Gelatin Inc.) that melts at or over a temperature (e.g., 37° C.) at which the vascular endothelial cell stops growing is applied to a pericyte cell layer (step S7 in FIG. 2). In addition, the vascular endothelial cell is embedded in the temperature-sensitive gel 6 (step S8 in FIG. 2) to culture the vascular endothelial cell for several days with the temperature inside the cell culture insert 1 maintained at, for example, 33° C. (step S9 in FIG. 2).

Thus, as shown in FIG. 4B, three cell layers including a vascular endothelial cell 7 embedded in the temperature-sensitive gel 6, a pericyte 8, and an astrocyte 9 are formed at the bottom of the cell culture insert 1. Although the pericyte 8 controls differentiation or growth of the vascular endothelial cell 7, the vascular endothelial cell 7 embedded in the temperature-sensitive gel 6 is not in contact with the pericyte 8 in this state, and thus the pericyte 8 cannot control the vascular endothelial cell 7. When the temperature inside the cell culture insert 1 is raised to 37° C., the vascular endothelial cell 7 stops growing, and the temperature-sensitive gel 6 melts (step S10 in FIG. 2). Thus, the vascular endothelial cell 7 comes into contact with the pericyte 8. The temperature inside the cell culture insert 1 is maintained at 33° C. to restart culture of the vascular endothelial cell 7. This completes the three-layer BBB model including the vascular endothelial cell 7, the pericyte 8, and the astrocyte 9.

Thus, the cell culture device according to the present embodiment simplifies injection of the cell culture medium 5 into the outer surface of the porous membrane 3 in the cell culture insert 1, sowing of the astrocyte 9, or transfer of the cell culture insert 1 having a BBB model at the bottom to the well 2*b* in the microplate 2. Thus, a handling device with a simple structure is usable for each operation. Such a handling device allows mass production of three-layer BBB models each including the vascular endothelial cell 7, the pericyte 8, and the astrocyte 9.

The cell culture method according to the present embodiment includes a process of seeding the cell layer of the pericyte 8 with the vascular endothelial cell 7 embedded in the temperature-sensitive gel 6. In this case, the vascular endothelial cell 7 remains apart from the pericyte 8 until the temperature-sensitive gel 6 melts. Thus, the pericyte 8 that controls differentiation or growth of the vascular endothelial cell 7 cannot function. More specifically, the cell culture method according to the present embodiment, with the temperature inside the cell culture insert 1 maintained at the temperature at which the temperature-sensitive gel 6 remains unmelted, allows a laminate of the vascular endothelial cell 7, the pericyte 8, and the astrocyte 9 formed at the bottom of the cell culture insert 1 through the processes in steps S1 to S9 in FIG. 2 to be maintained for a long time. The use of the temperature-sensitive gel 6 eliminates preparation of the vascular endothelial cell sheet and thus can eliminate a process of forming the cell sheet. Thus, the above cell culture method can enhance mass production of BBB models including the three cell layers.

The cell culture insert 1 including the fourth inner wall 1*e* serving as the inner wall of the cell culture chamber is used as the cell culture chamber as described below.

Second Embodiment

Figure 5A:
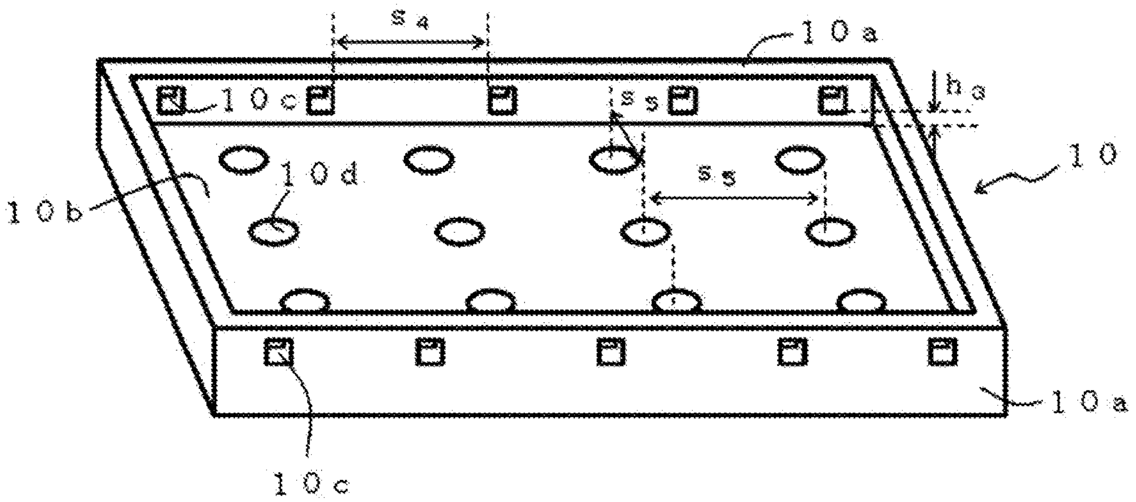
FIG. 5A is an external perspective view of an insert holding plate.
Figure 5B:
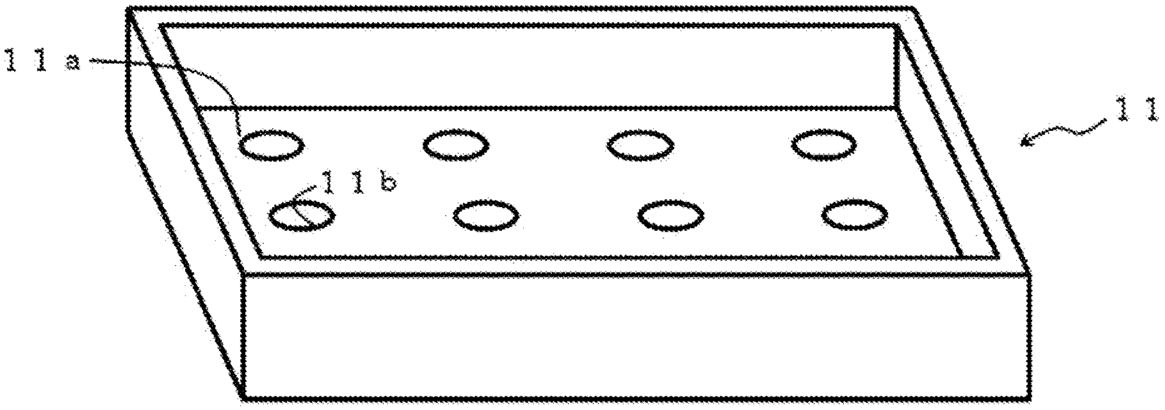
FIG. 5B is an external perspective view of a cell culture case.
Figure 6A:
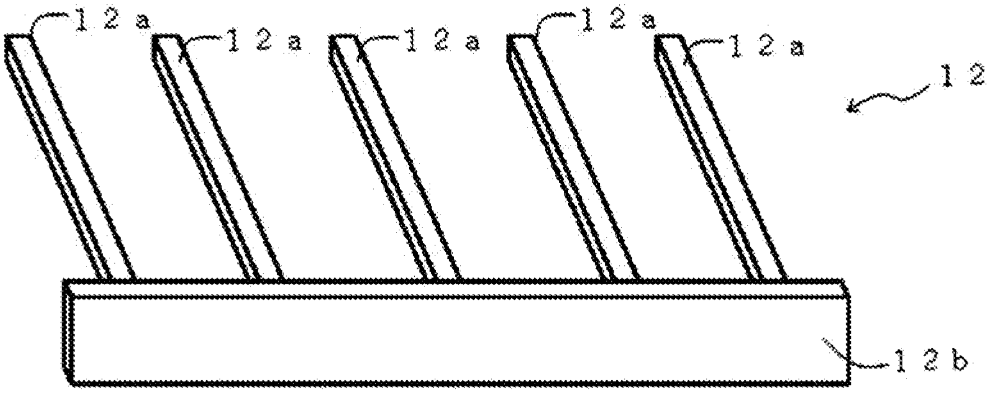
FIG. 6A is an external perspective view of an insert retainer.
Figure 6B:
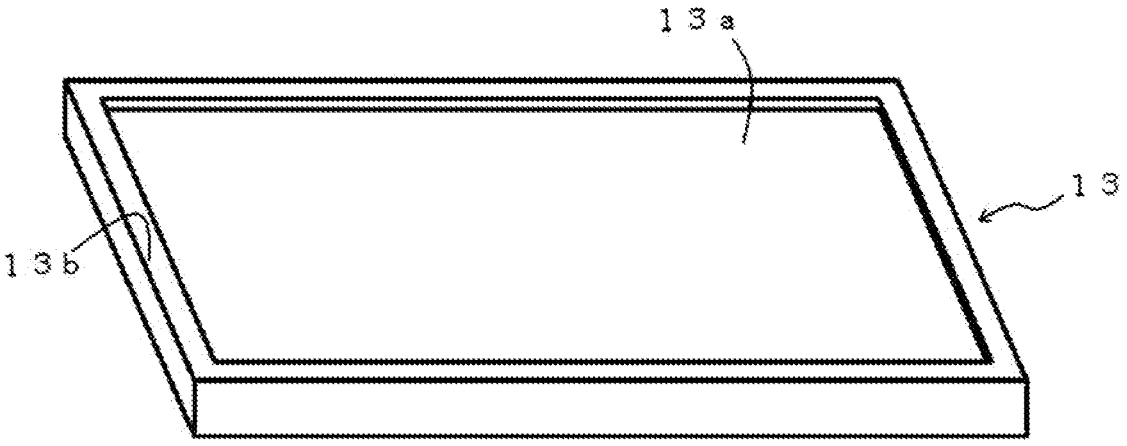
FIG. 6B is an external perspective view of a case lid.

With reference to FIGS. 5A to 6B, a cell culture device according to a second embodiment of the present invention will now be described. FIG. 5A is an external perspective view of an insert holding plate. FIG. 5B is an external perspective view of a cell culture case. FIG. 6A is an external perspective view of an insert retainer. FIG. 6B is an external perspective view of a case lid.

To avoid complexity in the drawings, a subset of angular holes and circular holes alone is denoted with reference numerals in FIGS. 5A and 5B.

The cell culture device according to the present embodiment includes an insert holding plate 10 (refer to FIG. 5A) and a cell culture case 11 (refer to FIG. 5B), which are rectangles with the same size as viewed in plan, an insert retainer 12 (refer to FIG. 6A), and a case lid 13 (refer to FIG. 6B).

As shown in FIG. 5A, the insert holding plate 10 has five angular holes 10*c* each in parallel with side plates 10*a* of a pair, and twelve (3 columns by 4 rows) circular holes 10*d* in a bottom board 10*b*. As shown in FIG. 5B, the cell culture case 11 has an open top, and has twelve (3 columns by 4 rows) circular through-holes 11*b* in a bottom board 11*a*.

The bottom board 10*b* in the insert holding plate 10 has the three circular holes 10*d* in a vertical line with their central axes on the same plane perpendicular to the side plates 10*a* and the bottom board 10*b*. The four circular holes 10*d* in a lateral line have their central axes on the same plane parallel to the side plates 10*a*. An interval $s_5$ (refer to FIG. 5A) between center lines of the two circular holes 10*d* is longer than the distance $s_3$ (refer to FIG. 1B) between the outermost surfaces of the pair of flanges 1*d* in the cell culture insert 1. More specifically, when the multiple cell culture inserts 1 are arranged on the bottom board 10*b* in the insert holding plate 10 to align their central axes X (refer to FIG. 1B) with the central axes of the circular holes 10*d*, the adjacent cell culture inserts 1 remain out of contact with each other.

When the cell culture case 11 is placed over the insert holding plate 10 to be parallel to and fully overlap the insert holding plate 10 as viewed in plan, the central axes of the twelve through-holes 11*b* align with the central axes of the twelve circular holes 10*d* in the insert holding plate 10.

As shown in FIG. 6A, the insert retainer 12 includes five square bars 12*a* parallel to each other and simultaneously receivable in the five angular holes 10*c*, and a coupler 12*b* that couples ends of the five square bars 12*a*. The square bars 12*a* are longer than the distance between the outer surfaces of the pair of side plates 10*a* in the insert holding plate 10.

As shown in FIG. 6B, the case lid 13 that is rectangular as viewed in plan and used as a cell culture chamber cover includes a rectangular recess 13*a*, and a frame-shaped protrusion 13*b* surrounding the recess 13*a*. The recess 13*a* placed over the cell culture case 11 allows the pair of side plates 10*a* to be positioned inside the protrusion 13*b*.

The cell culture case 11 including the through-hole 11*b* used as the inner wall of the cell culture chamber is used as the cell culture chamber as described below.

A cell culture method according to one or more embodiments of the present invention for fabricating three-layer BBB models including a vascular endothelial cell, a pericyte, and an astrocyte using the cell culture device according to the present embodiment will now be described with reference to FIGS. 7 to 10B.

Figure 7:
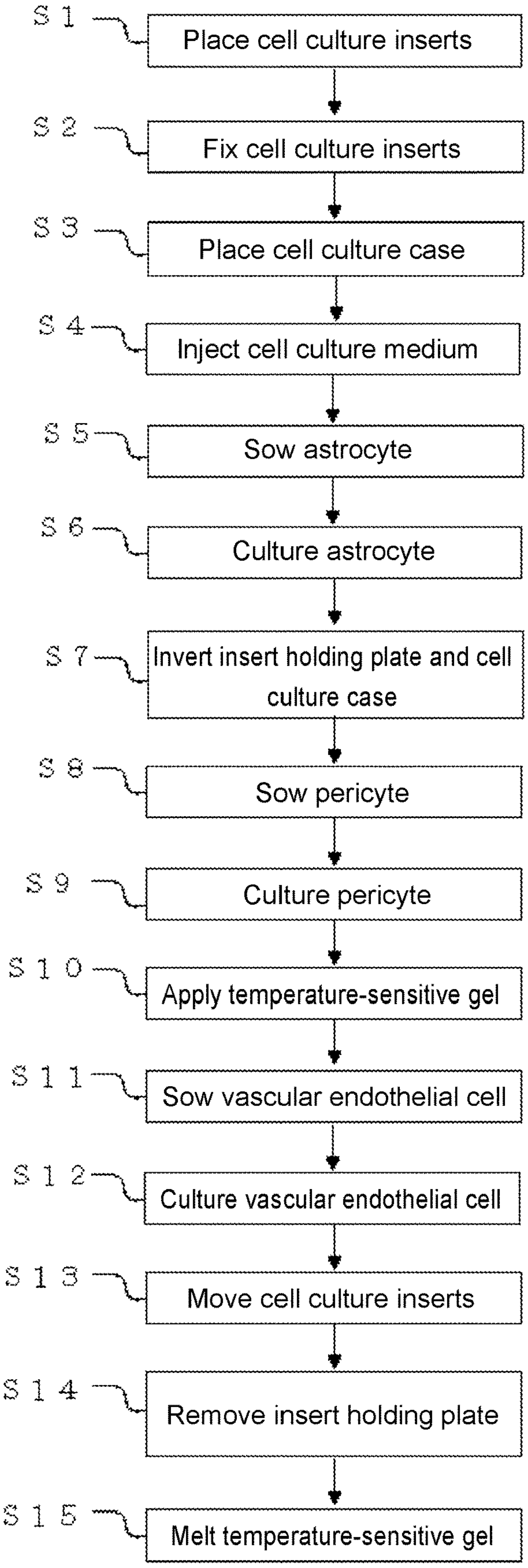
FIG. 7 is a flowchart of a cell culture method according to a second embodiment of the present invention.
Figure 8A:
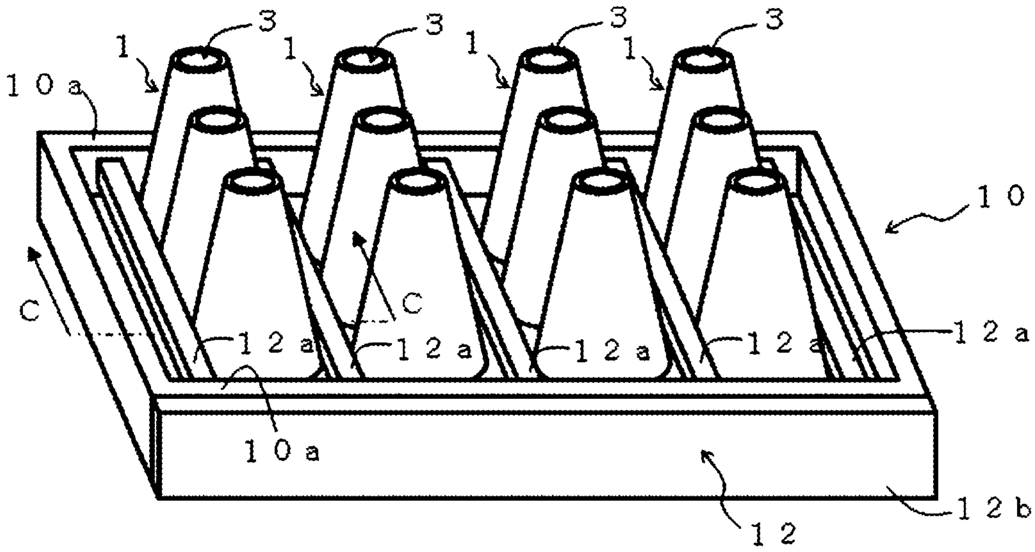
FIG. 8A is a perspective view of cell culture inserts placed on an insert holding plate.
Figure 8B:
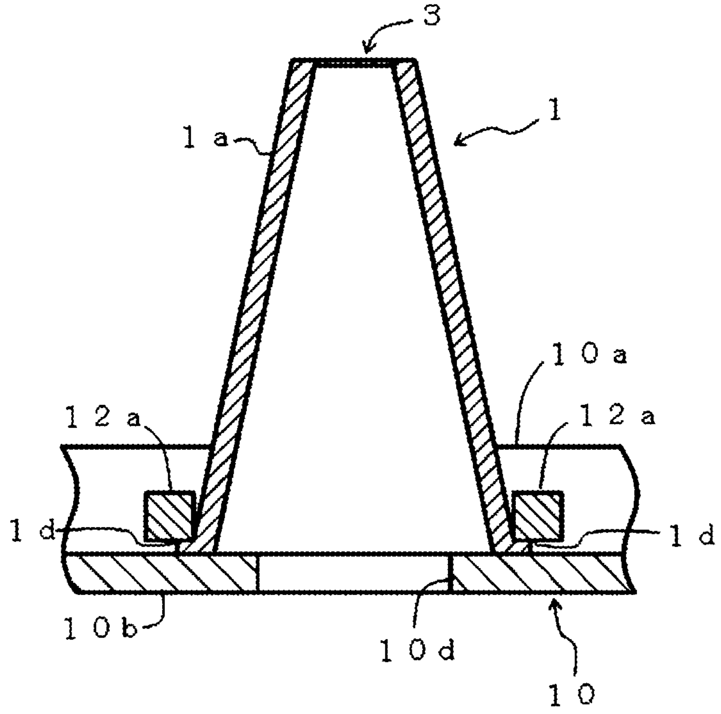
FIG. 8B is a cross-sectional view taken along line C-C as viewed in the direction indicated by arrows in FIG. 8A.
Figure 9A:
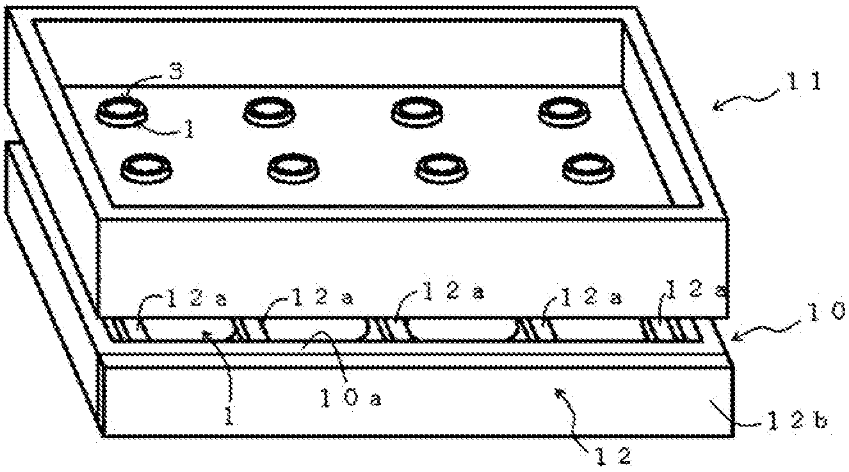
FIG. 9A is a perspective view of a cell culture case placed over the insert holding plate in FIG. 8A.
Figure 9B:
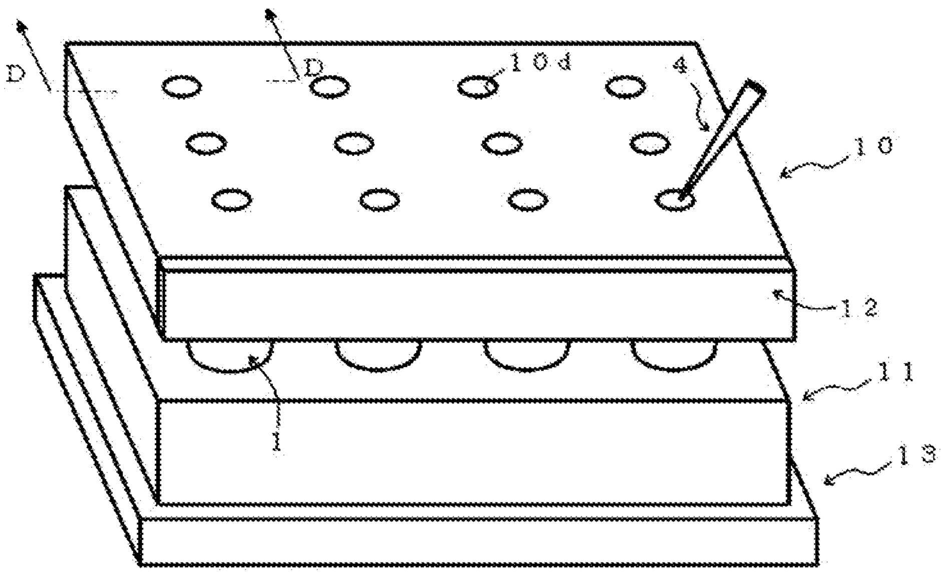
FIG. 9B is a perspective view of the cell culture case in FIG. 9A inverted together with the insert holding plate after a case lid is attached.
Figure 10A:
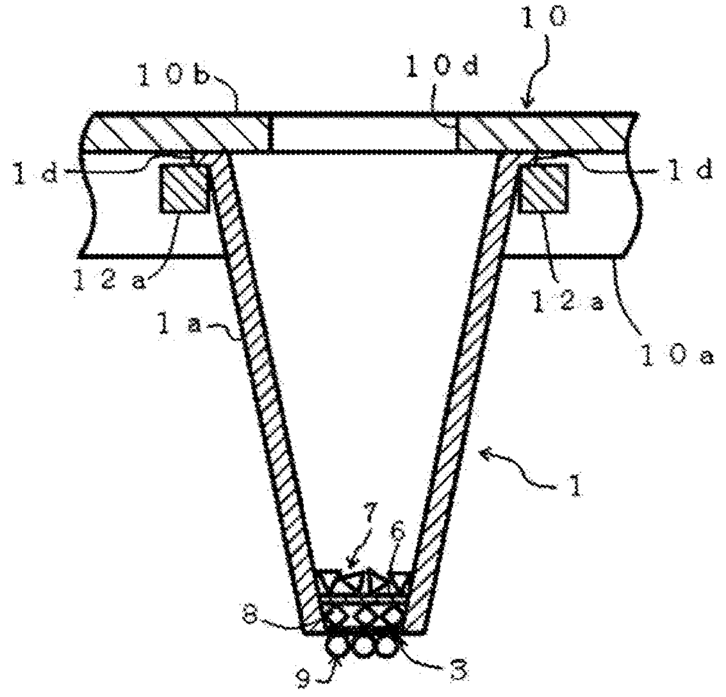
FIG. 10A is a cross-sectional view taken along line D-D as viewed in the direction indicated by arrows in FIG. 9B.
Figure 10B:
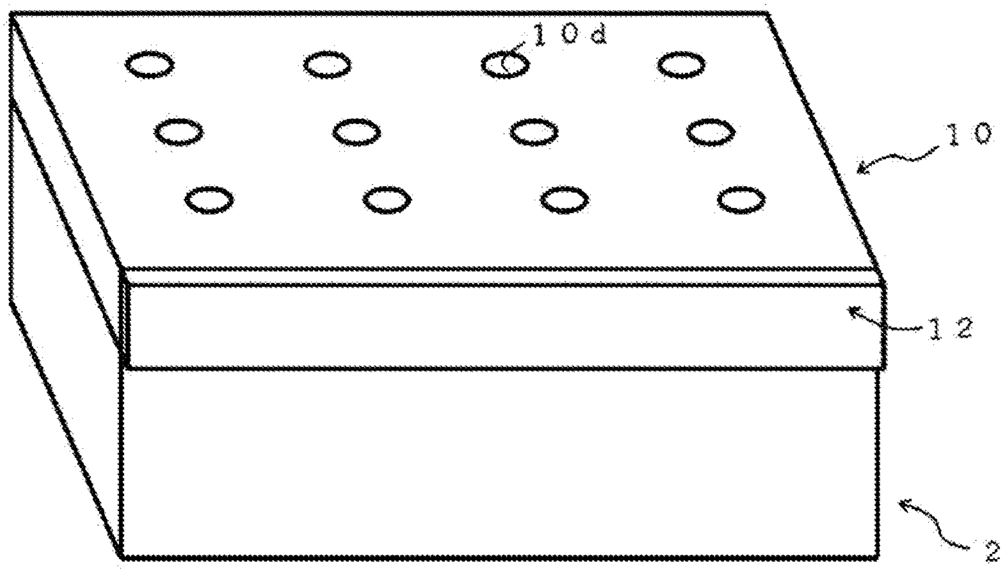
FIG. 10B is a perspective view of the cell culture inserts, placed in wells in a microplate, to which the insert holding plate and an insert retainer are attached.

FIG. 7 is a flowchart of a cell culture method according to the second embodiment of the present invention. FIG. 8A is a perspective view of cell culture inserts fixed to the insert holding plate by the insert retainer. FIG. 8B is a cross-sectional view taken along line C-C as viewed in the direction indicated by arrows in FIG. 8A. FIG. 9A is a perspective view of a cell culture case placed over the insert holding plate in FIG. 8A. FIG. 9B is a diagram of the cell culture case in FIG. 9A inverted together with the insert holding plate after a case lid is attached. FIG. 10A is a cross-sectional view taken along line D-D as viewed in the direction indicated by arrows in FIG. 9B. FIG. 10B is a perspective view of the cell culture inserts, placed in wells in a microplate, to which the insert holding plate and the insert retainer are attached.

To avoid complexity in the drawings, in FIGS. 9B and 10B, a subset of the angular holes and the circular holes alone is denoted with reference numerals, and in FIGS. 9A and 9B, one cell culture insert alone is denoted with the reference numerals. The cell culture case and the case lid are not shown in FIG. 10A.

As shown in FIG. 8A, the twelve cell culture inserts 1 facing down are placed on the bottom board 10*b* in the insert holding plate 10 to align the central axes X (refer to FIG. 1B) with the central axes of the circular holes 10*d* (step S1 in FIG. 7). Subsequently, the five square bars 12*a* in the insert retainer 12 are simultaneously received in all the angular holes 10*c* in the pair of side plates 10*a* in the insert holding plate 10.

The interval $s_4$ (refer to FIG. 5A) of the two angular holes 10*c* in the insert holding plate 10 is longer than the outer diameter $s_2$ (refer to FIG. 1B) of the side surface 1*a* of each cell culture insert 1 in the portion with the pair of flanges 1*d*, and shorter than the distance $s_3$ (refer to FIG. 1B) between the outermost surfaces of the pair of flanges 1*d*. A height $h_3$ (refer to FIG. 5A) of the angular holes 10*c* from the bottom board 10*b* is slightly larger than a thickness $h_4$ (refer to FIG. 1B) of the flanges 1*d* in the cell culture insert 1. The angular holes 10*c* are formed in the two side plates 10*a* to oppose to each other and to allow the square bars 12*a* (refer to FIG. 6A) in the insert retainer 12 to pass through them. Thus, as shown in FIG. 8A, the twelve cell culture inserts 1 placed on the bottom board 10*b* in the insert holding plate 10 are arranged with every three cell culture inserts 1 between the two square bars 12*a* in the insert retainer 12, and with the pair of flanges 1*d* located between the two square bars 12*a* and the bottom board 10*b* in the insert holding plate 10 (refer to FIG. 8B). Thus, the cell culture inserts 1 are unseparable from the insert holding plate 10.

Thus, each square bar 12*a* in the insert retainer 12 is received in the corresponding pair of angular holes 10*c* formed in the pair of side plates 10*a* in the insert holding plate 10 to oppose to each other. Thus, the cell culture inserts 1 are fixed to the insert holding plate 10 (step S2 in FIG. 7).

As shown in FIG. 9A, the cell culture case 11 is subsequently placed over the insert holding plate 10 in FIG. 8A to be parallel to, and to fully overlap the insert holding plate 10 as viewed in plan. In addition, the bottom of each cell culture insert 1 protrudes from the through-hole 11*b*, and exposes the outer surface of the porous membrane 3 to the inside of the cell culture case 11 (step S3 in FIG. 7). The suspended cell culture medium (not shown) is injected into the cell culture case 11 and seeded with the astrocyte 9 (steps S4 and S5 in FIG. 7). The astrocyte 9 is then cultured for several days until forming into a layer (step S6 in FIG. 7) with the temperature of the cell culture medium maintained at, for example, 33° C.

After the case lid 13 is attached to the upper surface of the cell culture case 11, as shown in FIG. 9B, the cell culture case 11 is carefully inverted together with the insert holding plate 10 and the insert retainer 12 (step S7 in FIG. 7) not to spill the cell culture medium and the astrocyte 9. The pericyte 8 is sown into the cell culture inserts 1 through the circular holes 10*d* in the insert holding plate 10 using the pipette 4 (step S8 in FIG. 7), and the pericyte 8 is cultured for several days until forming into a layer (step S9 in FIG. 7), with the temperature inside the cell culture inserts 1 maintained at, for example, 33° C. The cell culture medium is then removed after the pericyte is grown into a layer. Thus, the astrocyte 9 that has grown into a layer on the outer surface of each porous membrane 3 has cell projections extending through pores in the porous membrane 3 to a position near the pericyte 8 on the inner surface of the porous membrane 3.

When the bottom of each cell culture insert 1 protrudes from the through-hole 11*b*, the inside of the cell culture case 11 is usable as a cell culture chamber as in the cell culture insert 1, and the inside of the cell culture insert 1 and the inside of the cell culture case 11 are partitioned by the porous membrane 3. Specifically, when the multiple cell culture inserts 1 are placed on the cell culture case 11 to have the bottoms protruding from the through-holes 11*b*, the inside of the cell culture case 11 is partitioned by the multiple cell culture inserts 1 and the porous membrane 3. In the cell culture device according to the present embodiment, the fourth inner wall 1*e* (refer to FIG. 1B) of each tubular cell culture insert 1 and the inner wall of the corresponding through-hole 11*b* formed in the bottom board 11*a* in the cell culture case 11 thus define a pair of upper and lower cell culture chambers divided by the porous membrane 3. Multiple upper cell culture chambers are integrally coupled together, and lower cell culture chambers are integrally coupled together.

Subsequently, the temperature-sensitive gel 6 that melts at or over a temperature (e.g., 37° C.) at which the vascular endothelial cell stops growing is applied to the pericyte cell layer inside the cell culture insert 1 (step S10 in FIG. 7), and then the vascular endothelial cell 7 is embedded in the temperature-sensitive gel 6 (step S11 in FIG. 7). The vascular endothelial cell 7 is cultured for several days (step S12 in FIG. 7) with the temperature inside the cell culture insert 1 maintained at, for example, 33° C.

Thus, as shown in FIG. 10A, three cell layers including the vascular endothelial cell 7 embedded in the temperature-sensitive gel 6, the pericyte 8, and the astrocyte 9 are formed at the bottom of the cell culture insert 1. The twelve cell culture inserts 1 fixed to the insert holding plate 10 by the insert retainer 12 are removed from the through-holes 11*b* in the cell culture case 11, and the insert holding plate 10 and the insert retainer 12 are moved to the microplate 2 (step S13 in FIG. 7).

When all the square bars 12*a* in the insert retainer 12 are simultaneously drawn out from the angular holes 10*c* in the insert holding plate 10 with the bottoms of all the cell culture inserts 1 in the wells 2*b* in the microplate 2, the cell culture inserts 1 restricted by the insert holding plate 10 are released, and all the cell culture inserts 1 are simultaneously placed in the wells 2*b* in the microplate 2. When the insert holding plate 10 and the insert retainer 12 are removed from the cell culture inserts 1, the cell culture inserts 1 are fully placed in the wells 2*b* in the microplate 2 in the state shown in FIG. 4A (step S14 in FIG. 7). When the temperature inside the cell culture inserts 1 is raised to 37° C., the vascular endothelial cell 7 stops growing, the temperature-sensitive gel 6 melts (step S15 in FIG. 7), and the vascular endothelial cell 7 comes into contact with the pericyte 8. The temperature inside the cell culture inserts 1 is then maintained at 33° C. to restart culture of the vascular endothelial cell 7. This completes a three-layer BBB model including the vascular endothelial cell 7, the pericyte 8, and the astrocyte 9.

In the cell culture device according to the present embodiment as described above, the insert holding plate 10 and the insert retainer 12 serve as an insert holder for holding the multiple cell culture inserts 1 while allowing the cell culture inserts 1 to be simultaneously insertable into the through-holes 11*b* in the cell culture case 11. Thus, the multiple cell culture inserts 1 can be integrally inverted or transferred to the wells 2*b* in the microplate 2. Thus, the cell culture device according to the present embodiment can efficiently fabricate multiple BBB models in a short time.

The cell culture method according to the present embodiment includes a process of applying the temperature-sensitive gel 6 to the cell layer of the pericyte 8. This process eliminates preparation of a cell sheet of the vascular endothelial cell 7 and thus can eliminate a process of fabricating the cell sheet.

Instead of the through-holes 11*b*, the through-holes in the bottom board 11*a* in the cell culture case 11 may be angular holes or holes with other shapes. However, to prevent leakage of the cell culture medium 5 injected into the cell culture case 11, the cell culture inserts 1 are to fit to the through-holes.

Third Embodiment

Figure 11A:
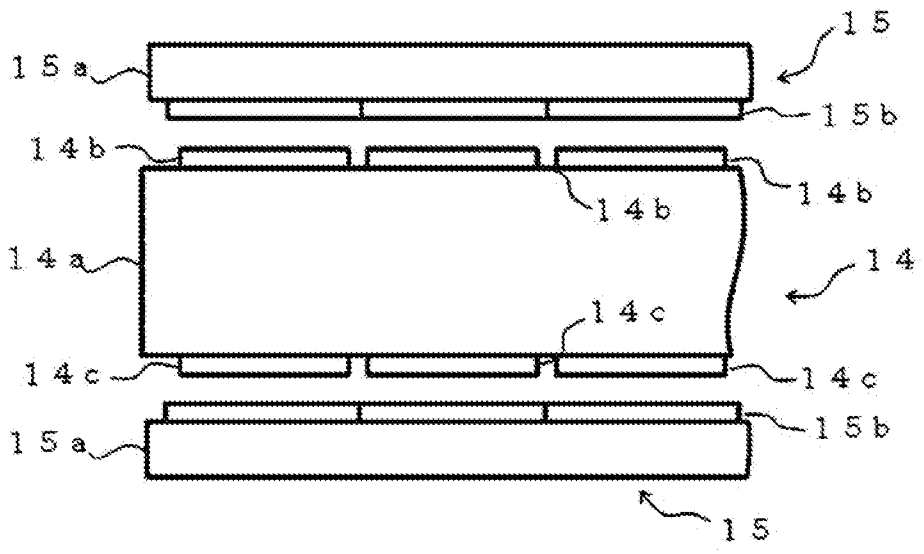
FIG. 11A is a side view of plate covers and a plate.
Figure 11B:
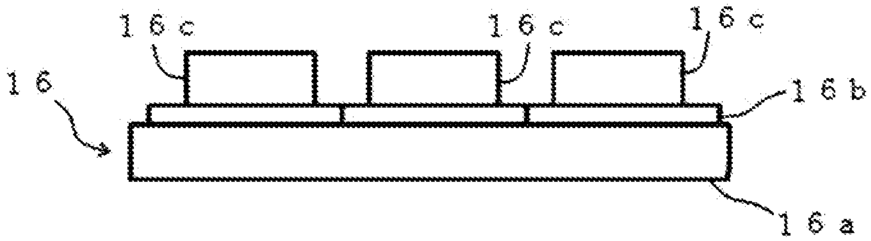
FIG. 11B is a side view of a spacer.
Figure 11C:
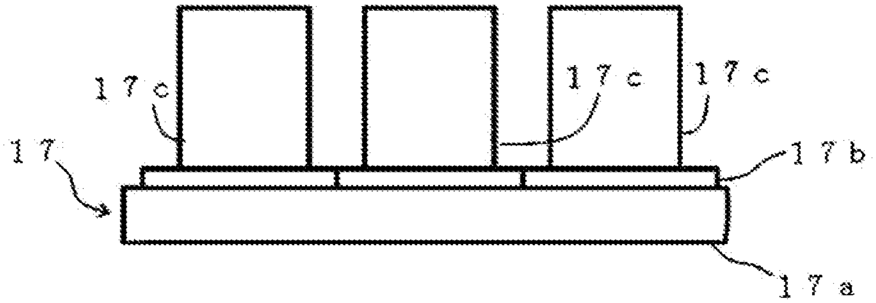
FIG. 11C is a side view of a pusher.
Figure 11D:
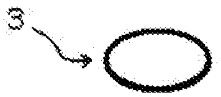
FIG. 11D is an external perspective view of a porous membrane.
Figure 11E:
FIG. 11E is an external perspective view of a membrane holder.
Figure 11F:
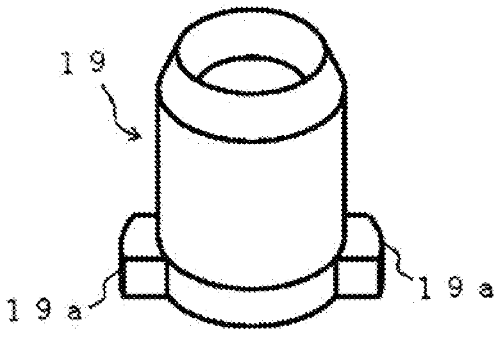
FIG. 11F is an external perspective view of an insert body.
Figure 12A:
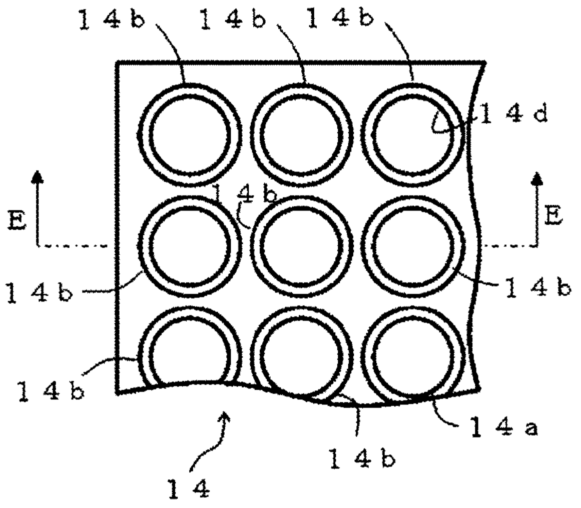
FIG. 12A is a plan view of the plate shown in FIG. 11A.
Figure 12C:
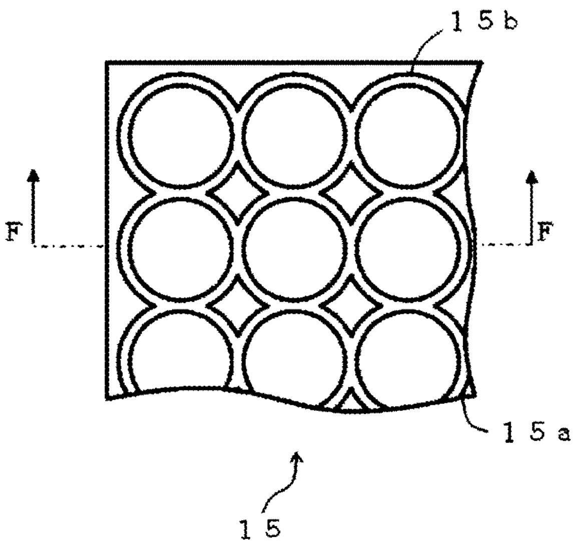
FIG. 12C is a plan view of the plate cover shown in FIG. 11A.
Figure 12B:
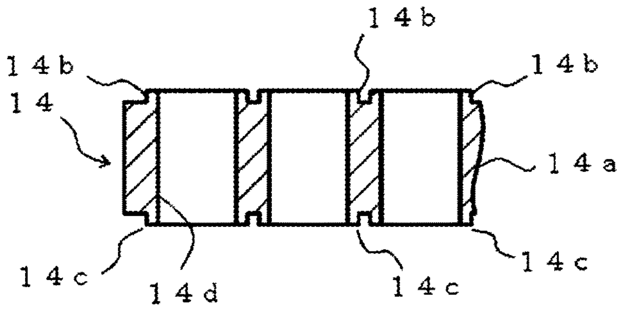
FIG. 12B is a cross-sectional view taken along line E-E as viewed in the direction indicated by arrows in FIG. 12A.
Figure 12D:
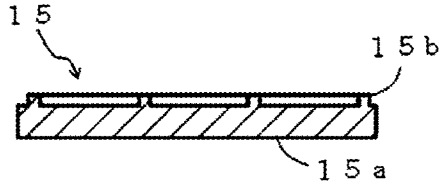
FIG. 12D is a cross-sectional view taken along line F-F as viewed in the direction indicated by arrows in FIG. 12C.

A cell culture device according to a third embodiment of the present invention will now be described with reference to FIGS. 11A to 14D. FIG. 11A is a side view of plate covers and a plate. FIG. 11B is a side view of a spacer. FIG. 11C is a side view of a pusher. FIG. 11D is an external perspective view of a porous membrane. FIG. 11E is an external perspective view of a membrane holder. FIG. 11F is an external perspective view of an insert body. FIG. 12A is a plan view of the plate shown in FIG. 11A. FIG. 12B is a cross-sectional view taken along line E-E as viewed in the direction indicated by arrows in FIG. 12A. FIG. 12C is a plan view of the plate cover shown in FIG. 11A. FIG. 12D is a cross-sectional view taken along line F-F as viewed in the direction indicated by arrows in FIG. 12C.

Figure 13A:
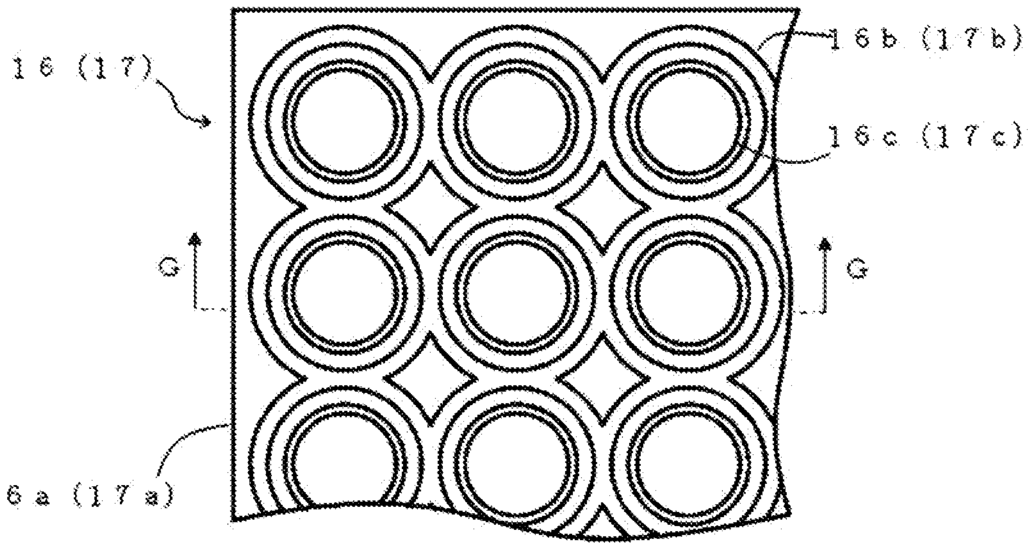
FIG. 13A is a plan view of the spacer shown in FIG. 11B and the pusher shown in FIG. 11C.
Figure 13B:
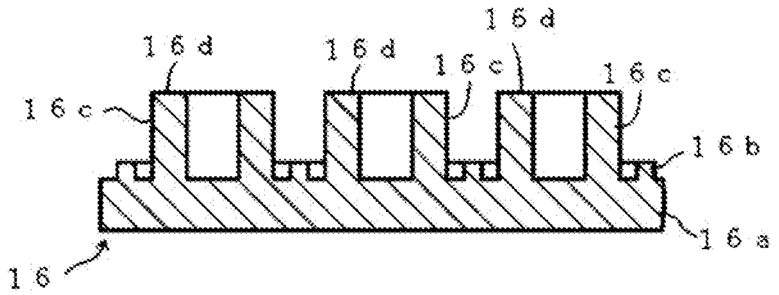
FIG. 13B is a cross-sectional view of the spacer.
Figure 13C:
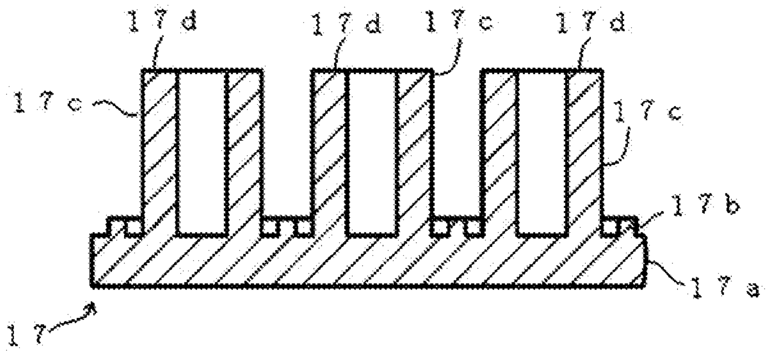
FIG. 13C is a cross-sectional view of the pusher.
Figure 14A:
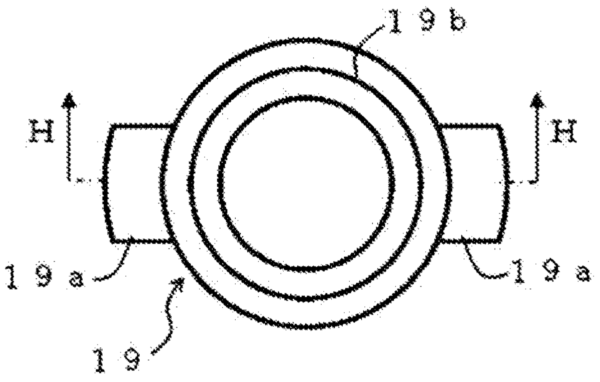
FIG. 14A is a plan view of the insert body shown in FIG. 11F.

FIG. 13A is a plan view of the spacer shown in FIG. 11B and the pusher shown in FIG. 11C. FIG. 13B is a cross-sectional view of the spacer taken along line G-G as viewed in the direction indicated by arrows in FIG. 13A. FIG. 13C is a cross-sectional view of the pusher taken along line G-G as viewed in the direction indicated by arrows in FIG. 13A. FIG. 14A is a plan view of the insert body shown in FIG. 11F. FIG. 14B is a cross-sectional view taken along line H-H as viewed in the direction indicated by arrows in FIG. 14A.

Figure 14C:
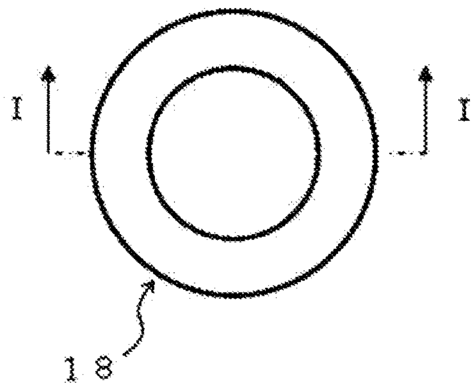
FIG. 14C is a plan view of the membrane holder shown in FIG. 11E.
Figure 14B:
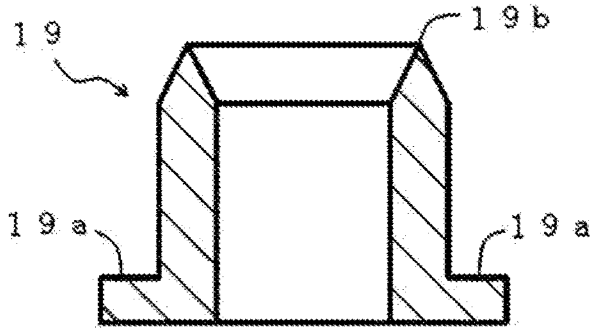
FIG. 14B is a cross-sectional view taken along line H-H as viewed in the direction indicated by arrows in FIG. 14A.
Figure 14D:
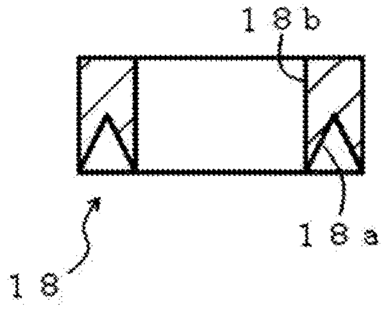
FIG. 14D is a cross-sectional view taken along line I-I as viewed in the direction indicated by arrows in FIG. 14C.

FIG. 14C is a plan view of the membrane holder shown in FIG. 11E. FIG. 14D is a cross-sectional view taken along line I-I as viewed in the direction indicated by arrows in FIG. 14C.

In FIGS. 13A to 13C, the spacer and the pusher are enlarged compared with the plate and the plate cover in FIGS. 12A to 12D. The spacer and the pusher have the same shape as viewed in plan and thus are denoted with their reference numerals in FIG. 13A.

As shown in FIGS. 11A to 11F, the cell culture device according to the present embodiment includes a plate 14, plate covers 15, a spacer 16, and a pusher 17. The plate 14 includes a planar base 14*a*, first annular protrusions 14*b* on one surface of the base 14*a*, and second annular protrusions 14*c* on the other surface of the planar base 14*a*. The first annular protrusions 14*b* and the second annular protrusions 14*c* have the same outer diameter. The plate covers 15 each include a planar base 15*a* and holders 15*b* on one surface of the base 15*a*. The spacer 16 includes a base 16*a* being a flat plate, and holders 16*b* and cylinders 16*c* on one surface of the base 16*a*. The pusher 17 includes a push plate 17*a* being a flat plate, and holders 17*b* and cylindrical push portions 17*c* on one surface of the push plate 17*a*. The cylinders 16*c* and the push portions 17*c* are sized to fit into the first annular protrusions 14*b* and the second annular protrusions 14*c*.

The cell culture device also includes a membrane holder 18, a polycarbonate porous membrane 3, and an insert body 19. The membrane holder 18 is a short cylinder sized to fit into a second annular protrusion 14*c*. The porous membrane 3 is attached to the membrane holder 18 to close one end of the membrane holder 18 and has both surfaces that allow a living organism material to be fixed on them. The insert body 19 is cylindrical, receives the membrane holder 18 on its first end, and includes a pair of flanges 19*a* on its second end. The insert body 19 and the membrane holder 18 form a cell culture insert.

The plate cover 15, the spacer 16, and the pusher 17 are sized to close the openings in the first annular protrusions 14*b* and the second annular protrusions 14*c* in the plate 14. The porous membrane 3 is fixed to the membrane holder 18 through thermal bonding.

As shown in FIGS. 12A and 12B, the base 14*a* in the plate 14 has multiple through-holes 14*d* serving as the inner walls of the cell culture chambers. The first annular protrusions 14*b* and the second annular protrusions 14*c* having the same inner diameter as the through-holes 14*d* are arranged on the two surfaces of the base 14*a* symmetrically with respect to the base 14*a*, and to be connected to each other through the through-holes 14*d*.

As shown in FIGS. 12C and 12D, the holders 15*b* on one surface of each plate cover 15 include multiple short cylinders sized to receive the opening ends of the first annular protrusions 14*b* and the second annular protrusions 14*c* in the plate 14. More specifically, the plate covers 15 serving as cell culture chamber covers are attachable to or detachable from the top and the bottom of the plate 14 with the opening ends of the first annular protrusions 14*b* and the second annular protrusions 14*c* at the holders 15*b* (refer to FIG. 16B).

As shown in FIGS. 13A to 13C, the holders 16*b* on one surface of the spacer 16 and the holders 17*b* on one surface of the pusher 17 include multiple short cylinders that are simultaneously fitted to the opening ends of the multiple first annular protrusions 14*b* in the plate 14. More specifically, the spacer 16 and the pusher 17 are attachable to or detachable from the top and the bottom of the plate 14 with the opening ends of the first annular protrusions 14*b* fitted to the respective holders 16*b* and 17*b* (refer to FIGS. 17B and 20).

The multiple cylinders 16*c* are located on the surface of the base 16*a* in the spacer 16 receiving the holders 16*b* with their cylinder axes aligned with the cylinder axes of the cylinders included in the holders 16*b*, and also to align with the first annular protrusions 14*b* and the second annular protrusions 14*c* as viewed in a direction perpendicular to the base 16*a* and the base 14*a* when the base 16*a* is placed parallel to the base 14*a* in the plate 14. The multiple push portions 17*c* are located on the push plate 17*a* in the pusher 17 on the surface receiving the holders 17*b* with their cylinder axes aligned with the cylinder axes of the cylinders included in the holders 17*b*, and to align with the first annular protrusions 14*b* and the second annular protrusions 14*c* as viewed in a direction perpendicular to the push plate 17*a* and the base 14*a* when the push plate 17*a* is placed parallel to the base 14*a* in the plate 14. More specifically, when the spacer 16 has the base 16*a* placed parallel to the base 14*a* in the plate 14 or when the pusher 17 has the push plate 17*a* placed parallel to the base 14*a* in the plate 14, the cylinder axes of all the cylinders 16*c* and all the push portions 17*c* are aligned with the cylinder axes of the first annular protrusions 14*b* and the second annular protrusions 14*c*.

The cylinders 16*c* and the push portions 17*c* have the outer diameter smaller than the inner diameter of the first annular protrusions 14*b* and are thus fittable to the first annular protrusions 14*b*, the second annular protrusions 14*c*, and the through-holes 14*d*. More specifically, the spacer 16 has all the cylinders 16*c* simultaneously fittable to the first annular protrusions 14*b*, the second annular protrusions 14*c*, and the through-holes 14*d* with the base 16*a* being parallel to the base 14*a* in the plate 14. The spacer 16 has the cylinders 16*c* movable in the through-holes 14*d* while maintaining the base 16*a* parallel to the base 14*a*. The pusher 17 has all the push portions 17*c* simultaneously fittable to the first annular protrusions 14*b*, the second annular protrusions 14*c*, and the through-holes 14*d* with the push plate 17*a* being parallel to the base 14*a* in the plate 14. The pusher 17 has the push portions 17*c* movable in the through-holes 14*d* while maintaining the push plate 17*a* parallel to the base 14*a*.

The sum of the length twice the length of each cylinder 16*c* in the spacer 16 and the length of the membrane holder 18 is equal to the sum of the lengths of each first annular protrusion 14*b*, each second annular protrusion 14*c*, and each through-hole 14*d*. More specifically, the cylinders 16*c* in the two spacers 16 hold the membrane holder 18 from the top and the bottom as described later when the cylinders 16*c* in one spacer 16 are received in the corresponding through-holes 14*d* in the plate 14, the base 16*a* is placed into contact with the end faces of the corresponding second annular protrusions 14*c*, the cylinders 16*c* in another spacer 16 are received in the corresponding through-holes 14*d* in the plate 14, and the base 16*a* is placed into contact with the end faces of the corresponding first annular protrusions 14*b* (refer to FIG. 19B).

The sum of the lengths of each push portion 17*c* of the pusher 17 and the membrane holder 18 is longer than the sum of the lengths of each first annular protrusion 14*b*, each second annular protrusion 14*c*, and the through-hole 14*d*. More specifically, when each push portion 17*c* of the pusher 17 is received in the corresponding through-hole 14*d* in the plate 14, and the push plate 17*a* is placed into contact with the end face of the corresponding second annular protrusion 14*c*, the porous membrane 3 attached to the membrane holder 18 placed on a distal end face 17*d* of the push portion

17*c* is pushed out of the corresponding first annular protrusion 14*b* together with the membrane holder 18 as described later (refer to FIG. 17B).

The inner diameter and the outer diameter of the insert body 19 are equal to the inner diameter and the outer diameter of the membrane holder 18, but the outer diameter of the membrane holder 18 is smaller than the inner diameter of the through-holes 14*d* in the plate 14. As shown in FIG. 14A, the insert body 19 has a taper 19*b* at the end having no flanges 19*a*. The membrane holder 18 has an annular recess (engageable portion 18*a*) at the end to which the porous membrane 3 is attached. The annular recess is engageable with the taper 19*b* in the insert body 19.

The cylinders 16*c* in the spacer 16 and the push portions 17*c* in the pusher 17 have the same inner diameter as the membrane holder 18. Thus, as described later with reference to FIG. 17A, when the cylinders 16*c* in the spacer 16 or the push portions 17*c* in the pusher 17 are received in the through-holes 14*d* in the plate 14 with the porous membranes 3 placed in the through-holes 14*d* in the plate 14 to be parallel to the base 14*a* in the plate 14, distal end faces 16*d* of the cylinders 16*c* (refer to FIG. 13B) are not in contact with the porous membranes 3 (refer to FIG. 20), and the distal end faces 17*d* of the push portions 17*c* (refer to FIG. 13C) are not in contact with the porous membranes 3 (refer to FIG. 17B). More specifically, the cylinders 16*c* in the spacer 16 and the push portions 17*c* in the pusher 17 can push and move the membrane holders 18 without affecting the cell layers on the outer surfaces of the porous membranes 3 by placing the distal end faces 16*d* and 17*d* into contact with the end faces of the membrane holders 18 to which the porous membranes 3 are attached.

As described later, the membrane holders 18 each including a third inner wall 18*b* (refer to FIG. 14D) serving as the inner wall of the cell culture chamber are used as cell culture chambers together with the plate 14 having the multiple through-holes 14*d* in the base 14*a* serving as the inner walls of the cell culture chambers.

A cell culture method according to one or more embodiments of the present invention for fabricating three-layer BBB models including a vascular endothelial cell, a pericyte, and an astrocyte using the cell culture device according to the present embodiment will now be described with reference to FIGS. 15 to 20.

Figure 15:
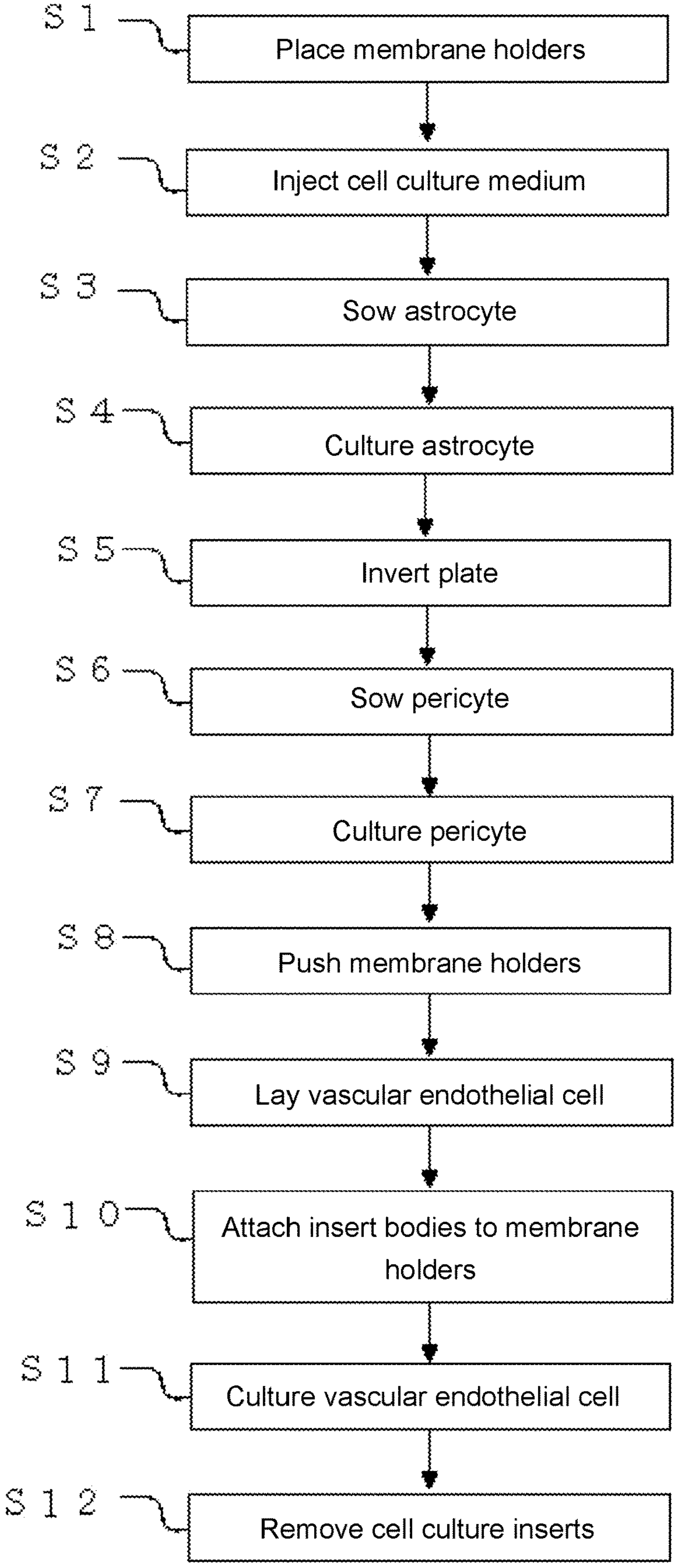
FIG. 15 is a flowchart of a cell culture method according to a third embodiment of the present invention.
Figure 16A:
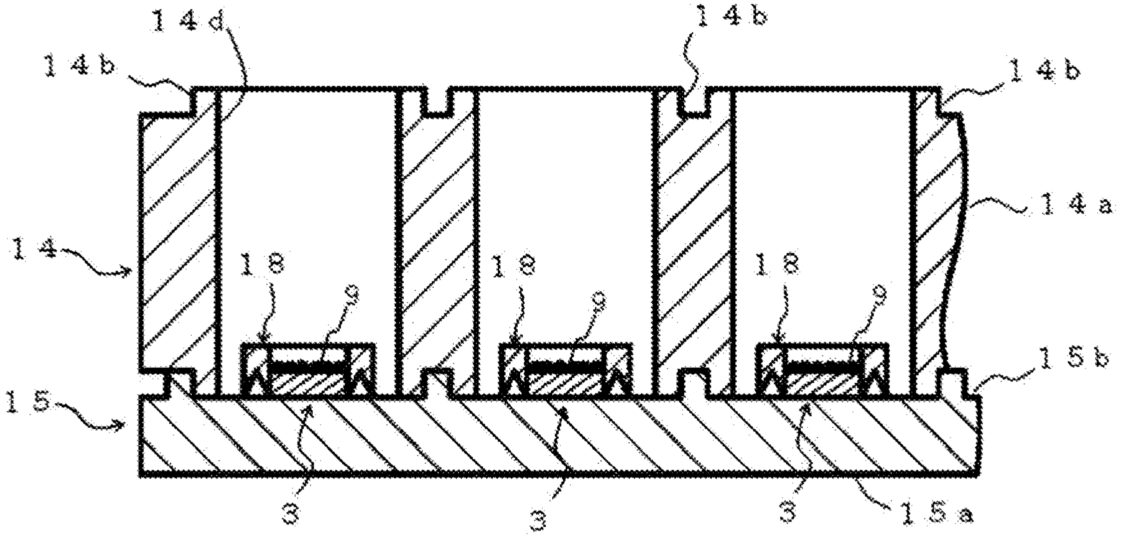
FIG. 16A is a cross-sectional view of a plate having the lower surface covered with a plate cover, and having membrane holders placed inside and seeded with an astrocyte.
Figure 16B:
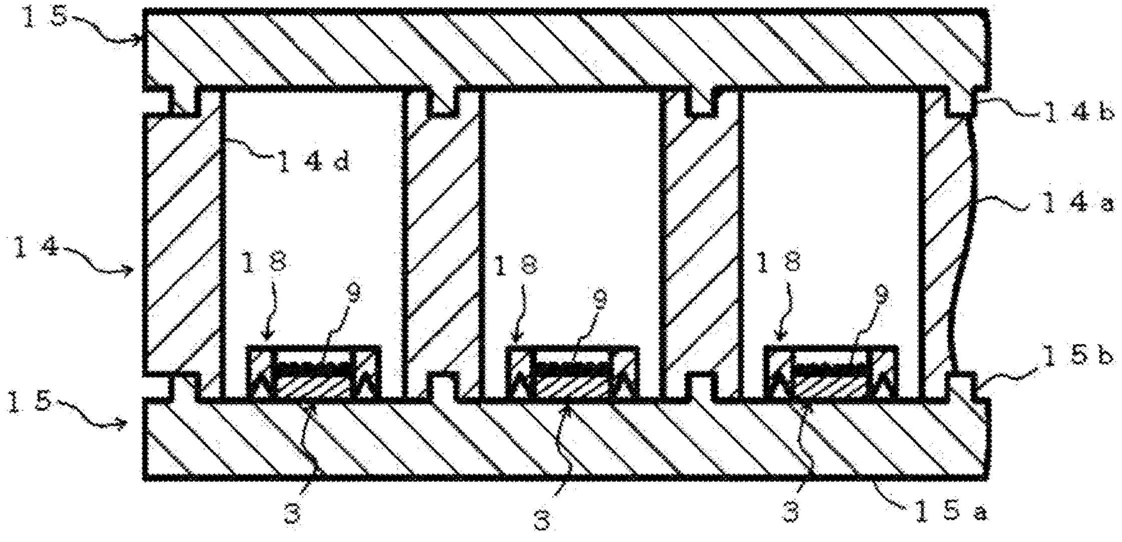
FIG. 16B is a cross-sectional view of the plate covered with the plate cover from above.
Figure 17A:
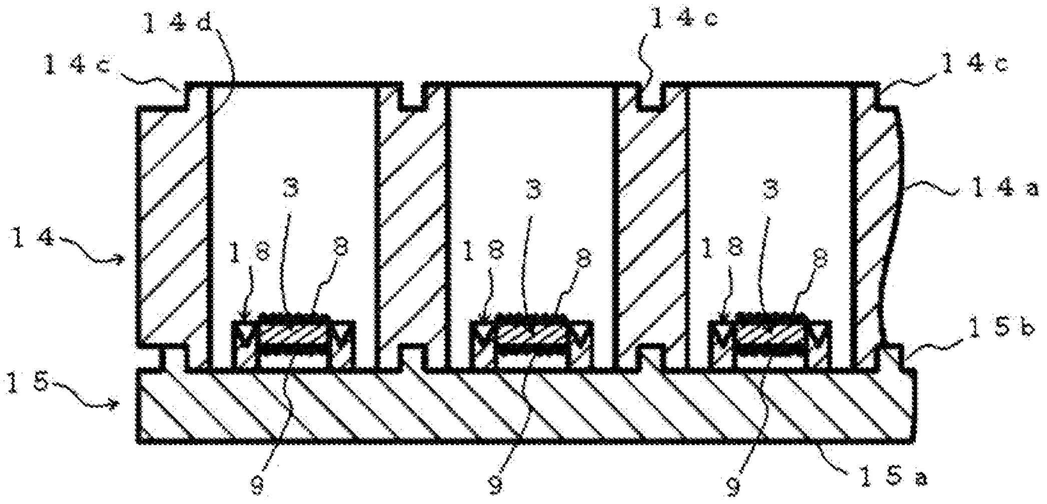
FIG. 17A is a cross-sectional view of the plate inverted in FIG. 16B, having the plate cover removed from its lower surface, and seeded with a pericyte.

FIG. 15 is a flowchart of a cell culture method according to the third embodiment of the present invention. FIG. 16A is a cross-sectional view of a plate having the lower surface covered with a plate cover, and having membrane holders placed inside and seeded with the astrocyte. FIG. 16B is a cross-sectional view of the plate covered with the plate cover from above. FIG. 17A is a cross-sectional view of the plate inverted in FIG. 16B, having the plate cover removed from its lower surface, and seeded with the pericyte. FIG. 17B is a cross-sectional view of the plate having the lower surface from which the plate cover in FIG. 17A is removed and receiving the pusher shown in FIG. 11C.

Figure 17B:
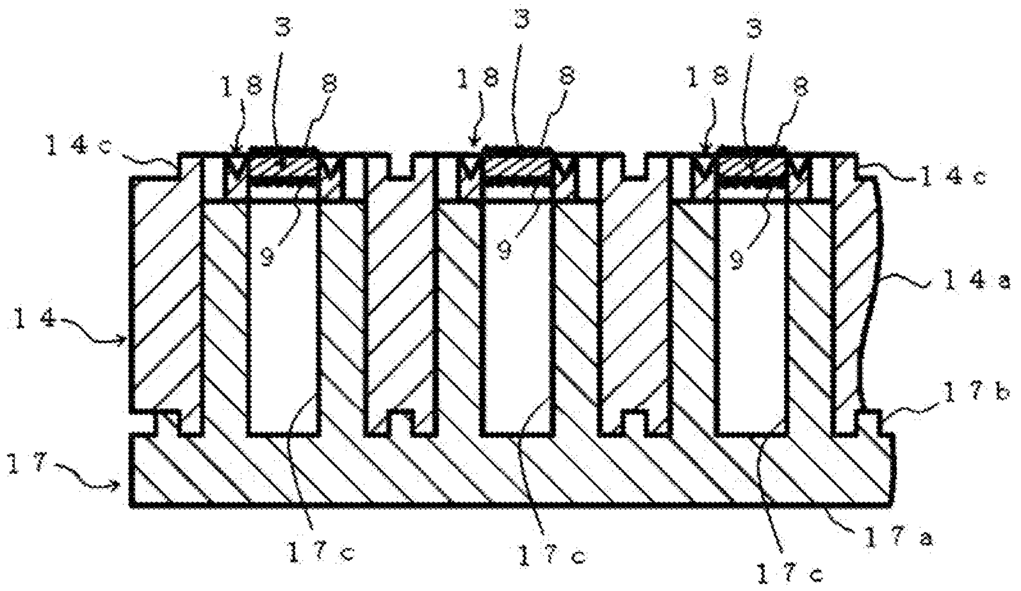
FIG. 17B is a cross-sectional view of the plate having the lower surface from which the plate cover in FIG. 17A is removed and receiving the pusher shown in FIG. 11C.
Figure 18A:
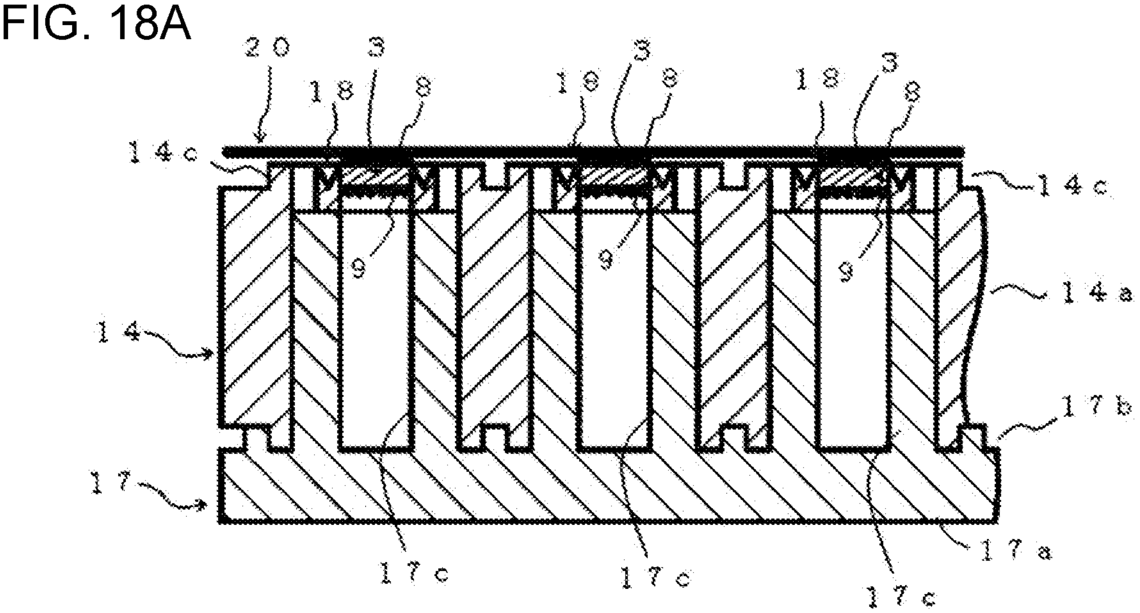
FIG. 18A is a cross-sectional view of a vascular endothelial cell sheet laid on the outer surfaces of the porous membranes in FIG. 17B.
Figure 18B:
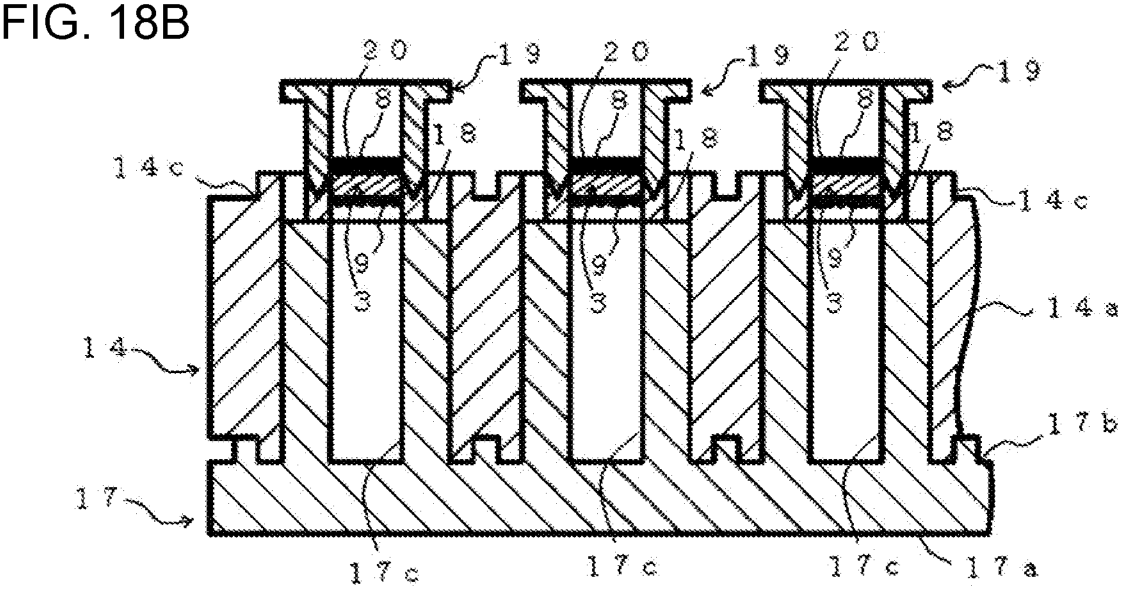
FIG. 18B is a cross-sectional view of the membrane holders in FIG. 18A attached to the lower ends of insert bodies.
Figure 18C:
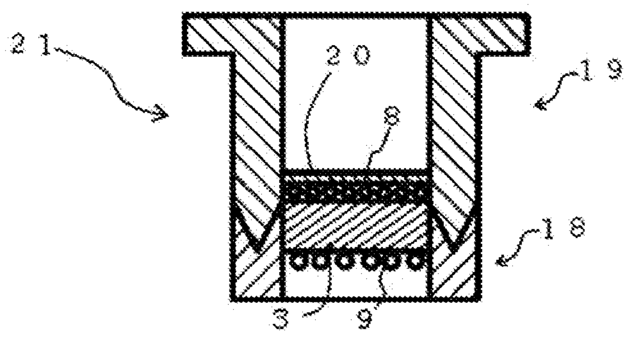
FIG. 18C is a cross-sectional view of a cell culture insert including the membrane holder and the insert body.
Figure 19A:
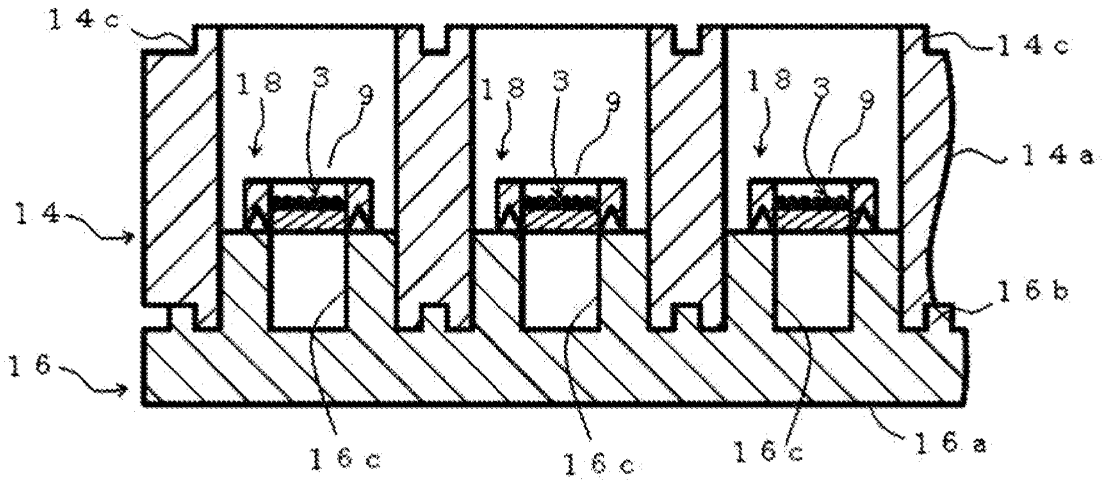
FIG. 19A is a cross-sectional view of the plate having the lower surface covered with the spacer shown in FIG. 11B, receiving the membrane holders inside, and seeded with an astrocyte.
Figure 19B:
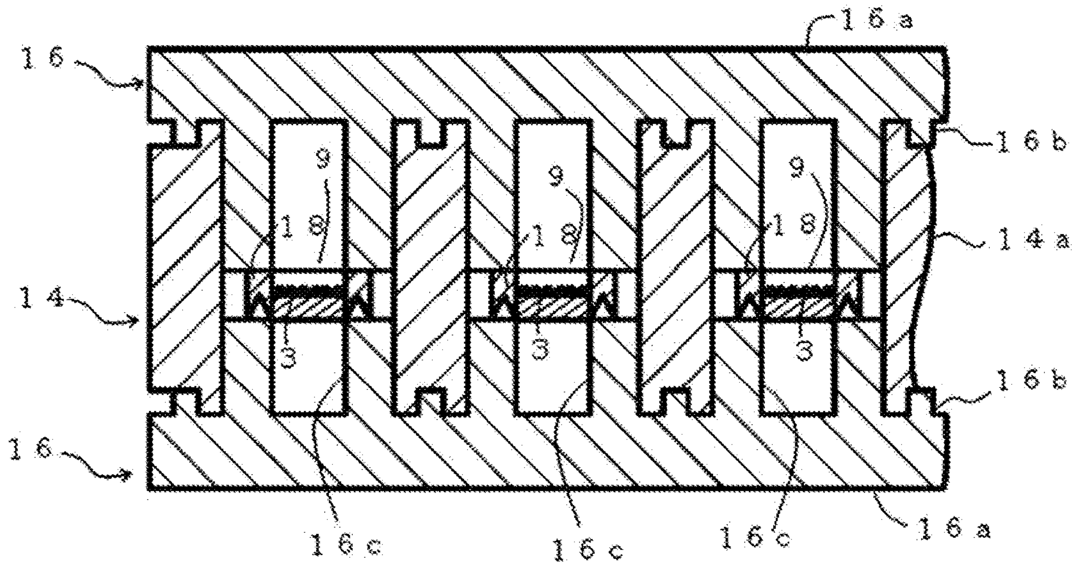
FIG. 19B is a cross-sectional view of the plate covered with the spacers from above and below.
Figure 20:
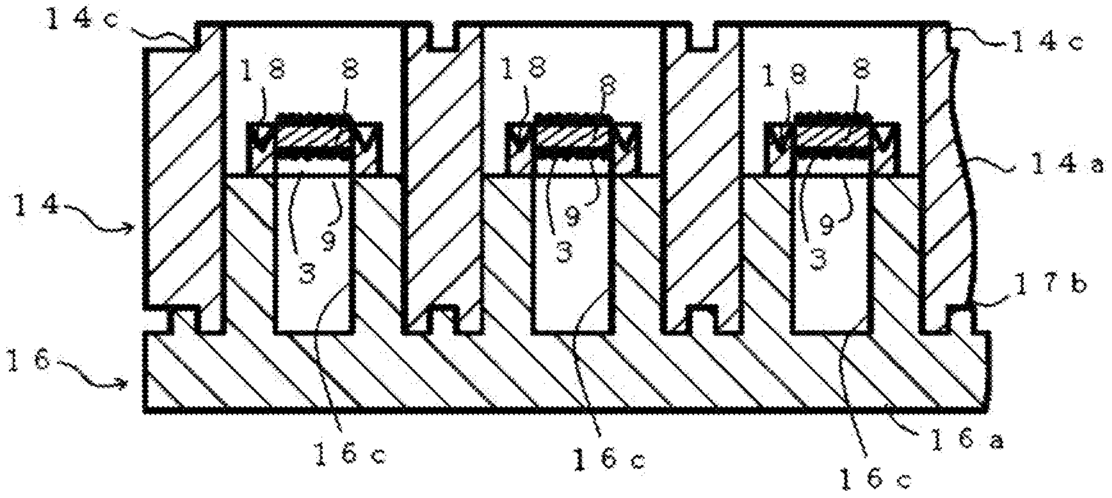
FIG. 20 is a cross-sectional view of the plate inverted in FIG. 19B, having the spacer removed from its lower surface, and seeded with a pericyte.

FIG. 18A is a cross-sectional view of a vascular endothelial cell sheet laid on the outer surfaces of the porous membranes in FIG. 17B. FIG. 18B is a cross-sectional view of the membrane holders in FIG. 18A attached to the lower ends of insert bodies. FIG. 18C is a cross-sectional view of the cell culture insert including the membrane holder and the insert body. FIG. 19A is a cross-sectional view of the plate having the lower surface covered with the spacer shown in FIG. 11B, receiving the membrane holders inside, and seeded with the astrocyte. FIG. 19B is a cross-sectional view of the plate covered with the spacers from above and below. FIG. 20 is a cross-sectional view of the plate inverted in FIG. 19B, having the spacer removed from its lower surface, and seeded with the pericyte.

First, the plate cover 15 is attached to the lower surface of the plate 14 having the base 14*a* located horizontally and the first annular protrusions 14*b* open upward, and the membrane holders 18 are placed in the through-holes 14*d* with the outer surfaces of the porous membranes 3 facing downward (step S1 in FIG. 15). Subsequently, as shown in FIG. 16A, a cell culture medium (not shown) is injected into the through-holes 14*d* in the plate 14 and seeded with the astrocyte 9 (steps S2 and S3 in FIG. 15). In this state, the astrocyte 9 is cultured for several days until forming into a layer with the temperature inside the through-holes 14*d* maintained at, for example, 33° C. (step S4 in FIG. 15).

As shown in FIG. 16B, after the plate cover 15 is attached to the upper surface of the plate 14, the plate 14 is carefully inverted not to spill the cell culture medium and the astrocyte 9 (step S5 in FIG. 15). As shown in FIG. 17A, after the plate cover 15 attached adjacent to the second annular protrusions 14*c* is removed, the pericyte 8 is sown into the through-holes 14*d* in the plate 14 (step S6 in FIG. 15). The pericyte 8 is then cultured for several days until forming into a layer with the temperature inside the through-holes 14*d* maintained at, for example, 33° C. The cell culture medium is removed after the pericyte 8 is grown into a layer (step S7 in FIG. 15). Thus, the astrocyte 9 that has grown into a layer on the inner surface of the porous membrane 3 has cell projections extending through pores in the porous membrane 3 to a position near the pericyte 8 on the outer surface of the porous membrane 3.

In this manner, the inside of each through-hole 14*d* in the plate 14 is used as a cell culture chamber. When the membrane holder 18 is placed, the cell culture chamber is partitioned into two by the porous membrane 3. In the cell culture device according to the present embodiment, the third inner wall 18*b* (refer to FIG. 14D) of each tubular membrane holder 18 and the inner wall of each through-hole 14*d* in the base 14*a* in the plate 14 thus define a pair of upper and lower cell culture chambers divided by the corresponding porous membrane 3. Multiple upper cell culture chambers are integrally coupled together, and lower cell culture chambers are integrally coupled together.

In FIG. 17A, the plate cover 15 is removed from the first annular protrusions 14*b* in the plate 14. As shown in FIG. 17B, the push portions 17*c* in the pusher 17 are received in the through-holes 14*d* in the plate 14 from below. As shown in FIG. 17B, the push portions 17*c* push the membrane holders 18 toward the second annular protrusions 14*c* (step S8 in FIG. 15).

As shown in FIG. 18A, a cell sheet 20 of the vascular endothelial cell 7 is laid on the pericyte 8 exposed outside the plate 14 in FIG. 17B (step S9 in FIG. 15). Each membrane holder 18 is placed at the distal end of the corresponding insert body 19 while punching out the cell sheet 20 of the vascular endothelial cell 7 from above using the insert body 19 and pushing the insert body 19 to the membrane holder 18 (refer to FIG. 18B). Thus, the three cell layers including the cell sheet 20 of the vascular endothelial cell 7, the pericyte 8, and the astrocyte 9 are placed in each insert body 19 (step S10 in FIG. 15). In this state, the temperature inside the insert body 19 is maintained at, for example, 33° C., and the vascular endothelial cell 7 is cultured for several days (step S11 in FIG. 15). After the vascular endothelial cell 7 is fully cultured, a cell culture insert 21 including the insert body 19 and the membrane holder 18 is removed from the plate 14 as shown in FIG. 18C (step S12 in FIG. 5).

When the plate 14 is inverted in step S5, the spacers 16 may be used instead of the plate covers 15 to prevent vertical movement of the membrane holders 18 in the through-holes 14*d*.

More specifically, the plate 14 may be inverted with the spacer 16 attached to the lower surface of the plate 14 instead of the plate cover 15 in step S1 as shown in FIG. 19A and with the spacer 16 attached to the upper surfaces of the through-holes 14*d* instead of the plate cover 15 in step S15 as shown in FIG. 19B. After the spacer 16 attached adjacent to the second annular protrusions 14*c* is removed, the pericyte 8 may be sown into the through-holes 14*d* in the plate 14 in step S6 as shown in FIG. 20. In this case, when the plate 14 is inverted, each membrane holder 18 is held by the cylinders 16*c* in the two spacers 16 not to move vertically in the through-hole 14*d*. Thus, the cell culture medium and the astrocyte 9 in the membrane holder 18 are less likely to be spilled.

As described above, the cell culture device according to the present embodiment performs, simultaneously on the multiple porous membranes 3 or the membrane holders 18, inversion of the porous membranes 3, removal of the membrane holders 18 from the through-holes 14*d* in the plate 14, or placement of the vascular endothelial cell 7 on top of the pericyte 8, which are to be performed in culturing the astrocyte 9 and the pericyte 8 on the two surfaces of the porous membranes 3. Thus, the cell culture device can fabricate multiple BBB models in a short time.

In the cell culture device according to the present embodiment, the holders 15*b* in the plate cover 15 are fitted to the first annular protrusions 14*b* or the second annular protrusions 14*c* in the plate 14 to enhance the adhesiveness of the plate cover 15 to the plate 14. In addition, the holders 17*b* in the pusher 17 are fitted to the first annular protrusions 14*b* or the second annular protrusions 14*c* in the plate 14 to accurately position the pusher 17 with respect to the plate 14.

The cell culture device according to the present embodiment enhances the adhesiveness of the plate cover 15 to the plate 14 using the holders 15*b*. Thus, the cell culture device can effectively prevent leakage of the cell culture medium injected into the through-holes 14*d* between the plate 14 and the plate cover 15. The cell culture device also accurately positions the pusher 17 with respect to the plate 14 using the holders 17*b*. Thus, the plate 14 and the pusher 17 are less likely to be broken.

The cell culture device according to one or more embodiments of the present invention is not limited to the above embodiment. For example, the cell culture device may include a watertight film of, for example, paraffin or polyethylene between each holder 15*b* in the plate cover 15 and the corresponding first annular protrusion 14*b* or second annular protrusion 14*c* in the plate 14, or between each holder 16*b* in the spacer 16 or each holder 17*b* in the pusher 17 and the corresponding first annular protrusion 14*b* or second annular protrusion 14*c* in the plate 14. In this case, the cell culture device improves the watertightness between the plate 14 and the plate cover 15 or between the plate 14 and the spacer 16 or the pusher 17. Thus, the cell culture medium 5 injected into the through-holes 14*d* is less likely to leak between the plate cover 15 and the pusher 17.

Fourth Embodiment

Figure 21A:
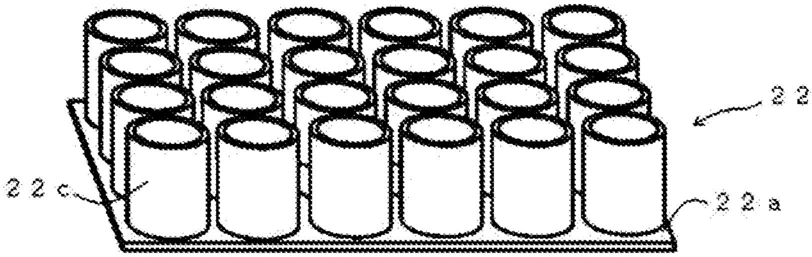
FIGS. 21A and 21B are external perspective views of a plate.
Figure 21B:
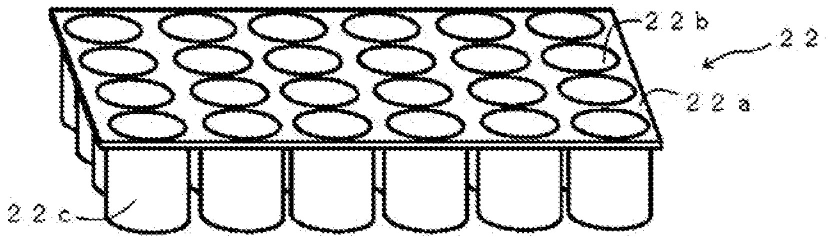
Figure 21C:
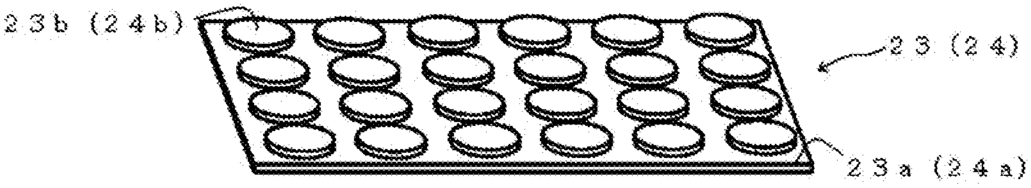
FIG. 21C is an external perspective view of a plate cover (spacer cover)
Figure 21D:
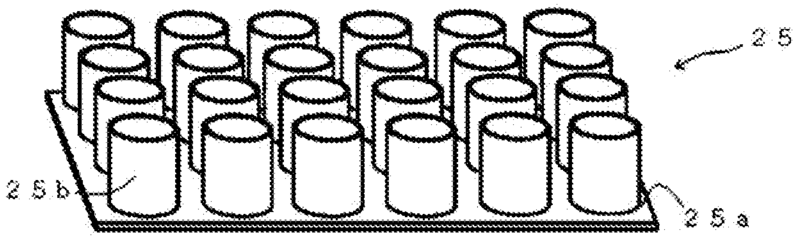
FIG. 21D is an external perspective view of a spacer.
Figure 22A:
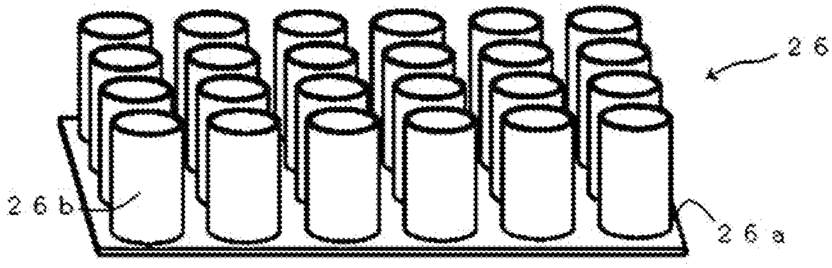
FIG. 22A is an external perspective view of a pusher.
Figure 22B:
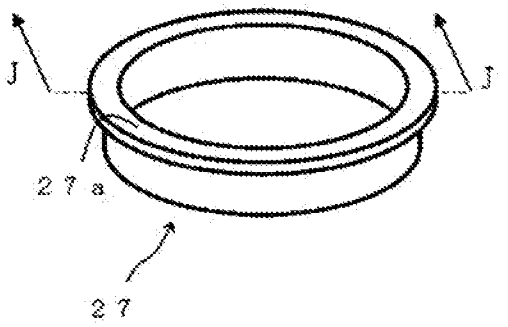
FIG. 22B is an external perspective view of a membrane holder.
Figure 22C:
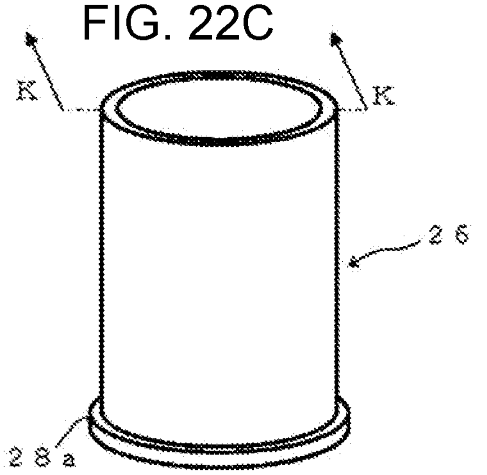
FIG. 22C is an external perspective view of a sleeve.
Figure 22D:
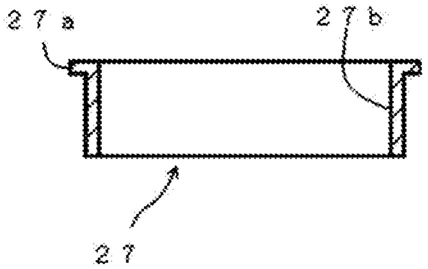
FIG. 22D is a cross-sectional view taken along line J-J as viewed in the direction indicated by arrows in FIG. 22B.
Figure 22E:
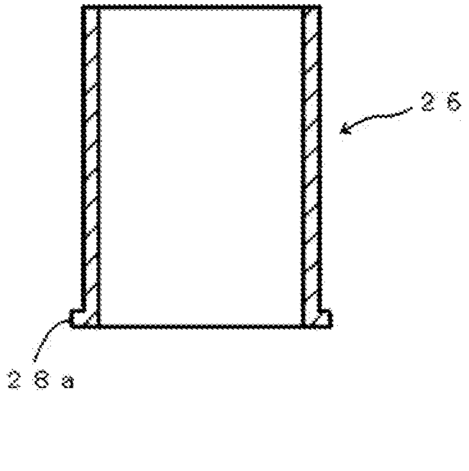
FIG. 22E is a cross-sectional view taken along line K-K as viewed in the direction indicated by arrows in FIG. 22C.
Figure 23A:
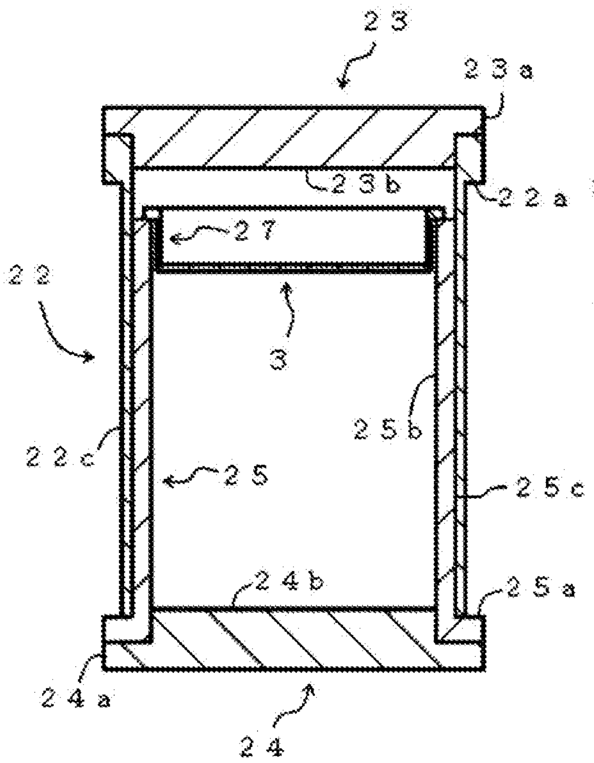
FIG. 23A is a longitudinal sectional view of a cylinder in the plate receiving a cylinder in the spacer.
Figure 23B:
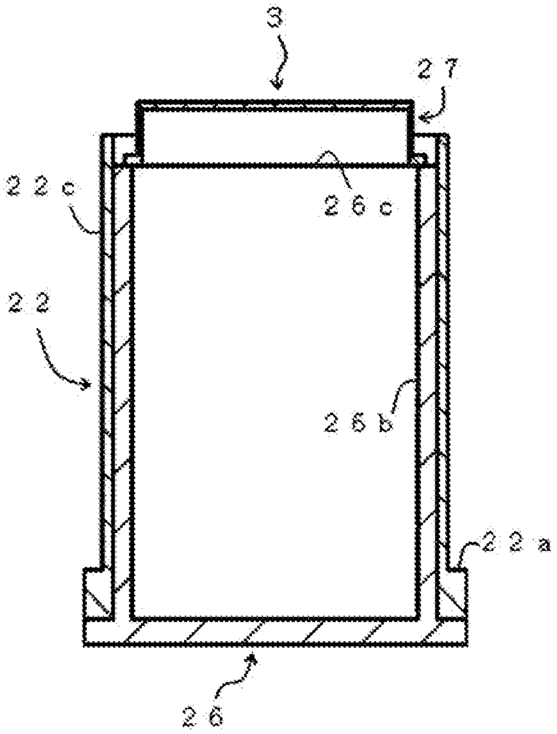
FIG. 23B is a longitudinal sectional view of the cylinder in the plate receiving a push portion of the pusher.

A cell culture device according to a fourth embodiment of the present invention will now be described with reference to FIGS. 21A to 23C. FIGS. 21A and 21B are external perspective views of a plate. FIG. 21C is an external perspective view of a plate cover (spacer cover), and FIG. 21D is an external perspective view of a spacer. FIG. 22A is an external perspective view of a pusher. FIG. 22B is an external perspective view of a membrane holder. FIG. 22C is an external perspective view of a sleeve. FIG. 22D is a cross-sectional view taken along line J-J as viewed in the direction indicated by arrows in FIG. 22B. FIG. 22E is a cross-sectional view taken along line K-K as viewed in the direction indicated by arrows in FIG. 22C. FIG. 23A is a longitudinal sectional view of a cylinder in the plate receiving a cylinder in the spacer. FIG. 23B is a longitudinal sectional view of the cylinder in the plate receiving a push portion of the pusher.

The plate cover and the spacer cover differ from each other simply in the outer diameter of their circular protrusions and have substantially the same outside shape, and thus are commonly shown with both their reference numerals in FIG. 21C. To avoid complexity in the drawings, in FIGS. 21A to 21D and 22A, one of the cylinders, one of the circular protrusions, and one of the through-holes are simply denoted with the reference numerals. FIG. 23A is a cross-sectional view of the cylinder in the plate and part of the surrounding of its base end, the circular protrusions in the plate cover and the spacer cover and part of the surroundings of their base ends, a cylinder in the spacer and part of the surrounding of its base end, and the membrane holder placed in the cylinder in the spacer, taken along a plane including the cylinder axis of the cylinder in the plate. FIG. 23B is a cross-sectional view of the push portion of the pusher and part of the surrounding of its base end, the membrane holder pushed out by the pusher, and the cylinder in the plate and part of the surrounding of its base end, taken along a plane including the cylinder axis of the cylinder in the plate.

As shown in FIGS. 21A to 21D and 22A to 22E, the cell culture device according to the present embodiment includes a plate 22, a plate cover 23, a spacer cover 24, a spacer 25, a pusher 26, membrane holders 27, and a sleeve 28. The plate 22 includes a planar base 22*a* having multiple through-holes 22*b*, and as many cylinders 22*c* as the through-holes 22*b* on a surface of the planar base 22*a* to serve as the inner walls of cell culture chambers. The plate cover 23 includes a planar base 23*a*, and as many circular protrusions 23*b* as the cylinders 22*c* in the plate 22 on a surface of the planar base 23*a* to serve as a cell culture chamber cover. The spacer cover 24 includes a planar base 24*a*, and as many circular protrusions 24*b* as the cylinders 22*c* in the plate 22 on a surface of the planar base 24*a* to serve as a cell culture chamber cover.

The spacer 25 includes a planar base 25*a* having as many through-holes 25*b* (refer to FIG. 23A) as the through-holes 22*b* to serve as the inner walls of cell culture chambers and arranged in the planar base 25*a*, and as many cylinders 25*c* as the through-holes 25*b* on a surface of the planar base 25*a*. The pusher 26 includes a planar push plate 26*a*, and as many cylindrical push portions 26*b* as the cylinders 22*c* in the plate 22 on a surface of the push plate 26*a*. Each membrane holder 27 is a substantial short cylinder insertable into the cylinder 22*c* in the plate 22. The sleeve 28 is substantially cylindrical and receives the membrane holder 27 at one end.

As shown in FIGS. 22B and 22D, the membrane holder 27 has a flange 27*a* at one end, and has the porous membrane 3 fixed to the inner surface at the other end through thermal bonding.

The cylinders 22*c* in the plate 22 have the inner diameter equal to the diameter of the through-holes 22*b*, and have the cylinder axes aligned with the center axes of all the through-holes 22*b*.

The circular protrusions 23*b* in the plate cover 23 can fit to the cylinders 22*c* in the plate 22, and have the center axes aligned with the center axes of all the through-holes 22*b* with the base 22*a* parallel to the base 23*a*. More specifically, when the base 23*a* in the plate cover 23 is moved toward the base 22*a* in the plate 22 while being maintained parallel to the base 22*a*, all the circular protrusions 23*b* simultaneously fit to all the cylinders 22*c* (refer to FIG. 23A).

The circular protrusions 24*b* in the spacer cover 24 can fit to the cylinders 25*c* in the spacer 25, and have the center axes aligned with the cylinder axes of all the cylinders 25*c* with the base 25*a* parallel to the base 24*a*. More specifically, when the base 24*a* in the spacer cover 24 is moved toward the base 25*a* in the spacer 25 while being maintained parallel to the base 25*a*, all the circular protrusions 24*b* simultaneously fit to all the cylinders 25*c* (refer to FIG. 23A).

The cylinders 25*c* in the spacer 25 have the outer diameter smaller than the inner diameter of the cylinders 22*c* in the plate 22 to fit to the cylinders 22*c*, and have the cylinder axes aligned with the center axes of all the through-holes 22*b* with the base 22*a* parallel to the base 25*a*. More specifically, when the base 25*a* in the spacer 25 is moved toward the base 22*a* in the plate 22 while being maintained parallel to the base 22*a*, all the cylinders 25*c* simultaneously fit to all the cylinders 22*c* (refer to FIG. 23A).

The push portions 26*b* in the pusher 26 have the outer diameter smaller than the inner diameter of the cylinders 22*c* in the plate 22 to fit to the cylinder 22*c*, and have the cylinder axes aligned with the center axes of all the through-holes 22*b* with the base 22*a* parallel to the push plate 26*a*. More specifically, when the push plate 26*a* in the pusher 26 is moved toward the base 22*a* in the plate 22 while being maintained parallel to the base 22*a*, all the push portions 26*b* simultaneously fit to all the cylinders 22*c* (refer to FIG. 23B). The sum of the lengths of each push portion 26*b* in the pusher 26 and each membrane holder 27 is greater than the sum of the lengths of the base 22*a* and each cylinder 22*c*. More specifically, when the push portions 26*b* in the pusher 26 are received in the through-holes 22*b* in the plate 22, and the push plate 26*a* is placed into contact with the base 22*a*, the porous membranes 3 attached to the membrane holders 27 placed on distal end faces 26*c* of the push portions 26*b* are pushed out of the cylinders 22*c* together with the membrane holders 27 (refer to FIG. 23B).

As described later, each membrane holder 27 including a second inner wall 27*b* (refer to FIG. 22D) serving as the inner wall of the cell culture chamber is used as a cell culture chamber together with the plate 22 including the base 22*a* with the multiple through-holes 22*b* and the cylinders 22*c* serving as the inner walls of the cell culture chambers and the spacer 25 including the base 25*a* with the multiple through-holes 25*b* and the cylinders 25*c* serving as the inner walls of the cell culture chambers.

A cell culture method according to one or more embodiments of the present invention for fabricating three-layer BBB models including a vascular endothelial cell, a pericyte, and an astrocyte using the cell culture device according to the present embodiment will now be described with reference to FIGS. 24 to 30B.

Figure 24:
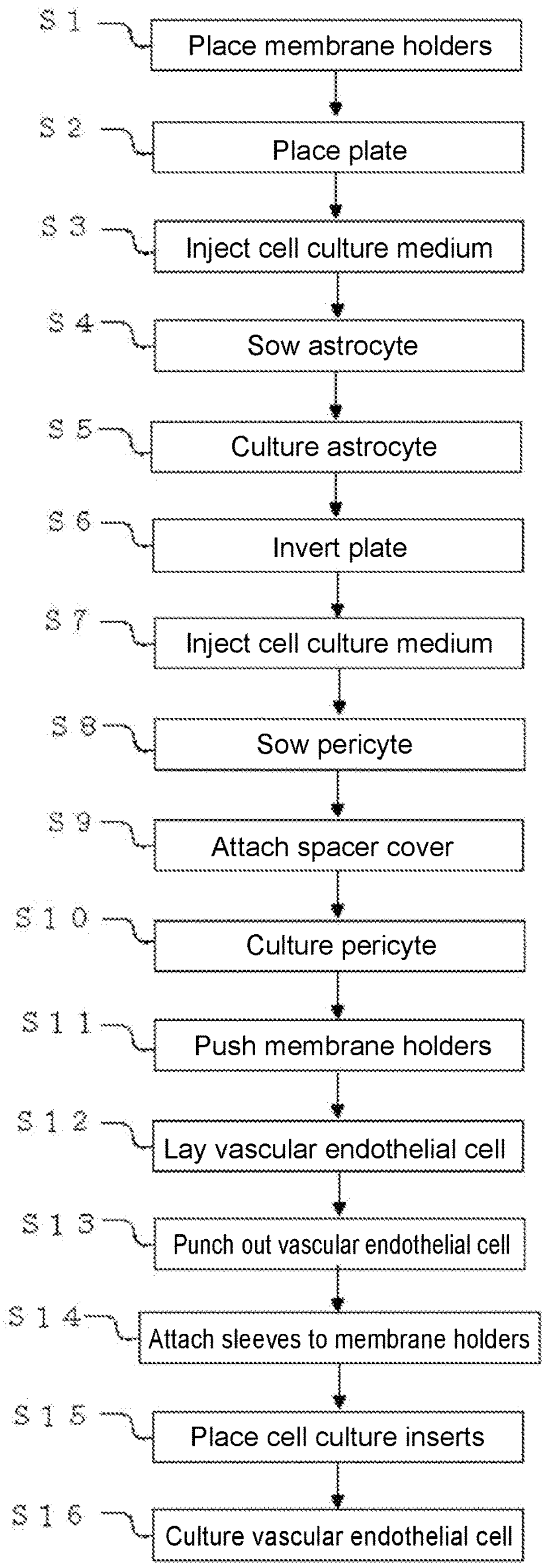
FIG. 24 is a flowchart of a cell culture method according to a fourth embodiment of the present invention.
Figure 25A:
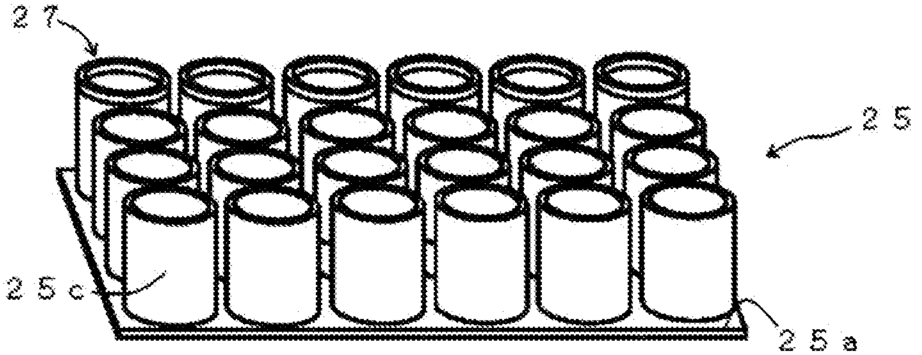
FIG. 25A is a diagram of membrane holders placed on the upper ends of the cylinders in the spacer in FIG. 21D.
Figure 25B:
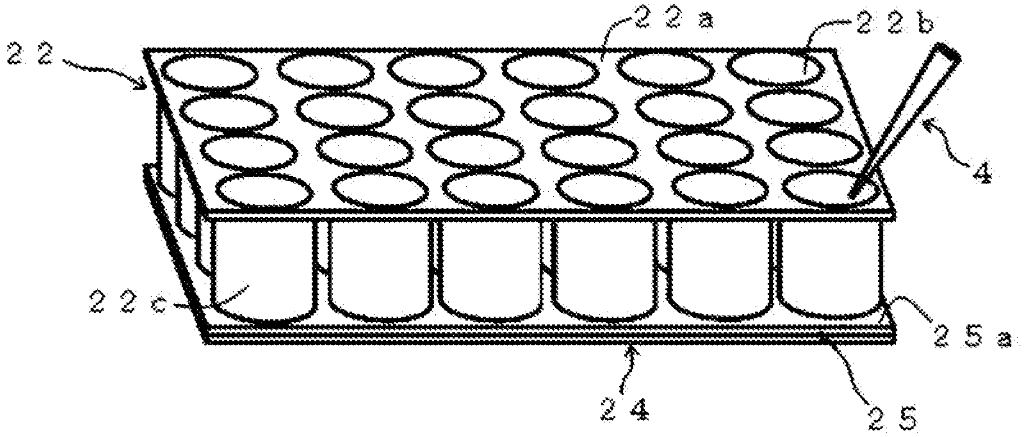
FIG. 25B is a diagram of the spacer in FIG. 25A inverted after the spacer cover and the plate are attached.
Figure 25C:
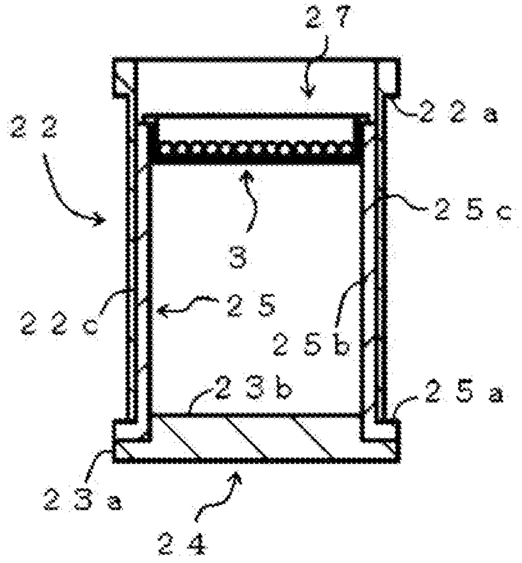
FIG. 25C is a longitudinal sectional view of the spacer, the cylinder in the plate, and the membrane holder in FIG. 25B.
Figure 26A:
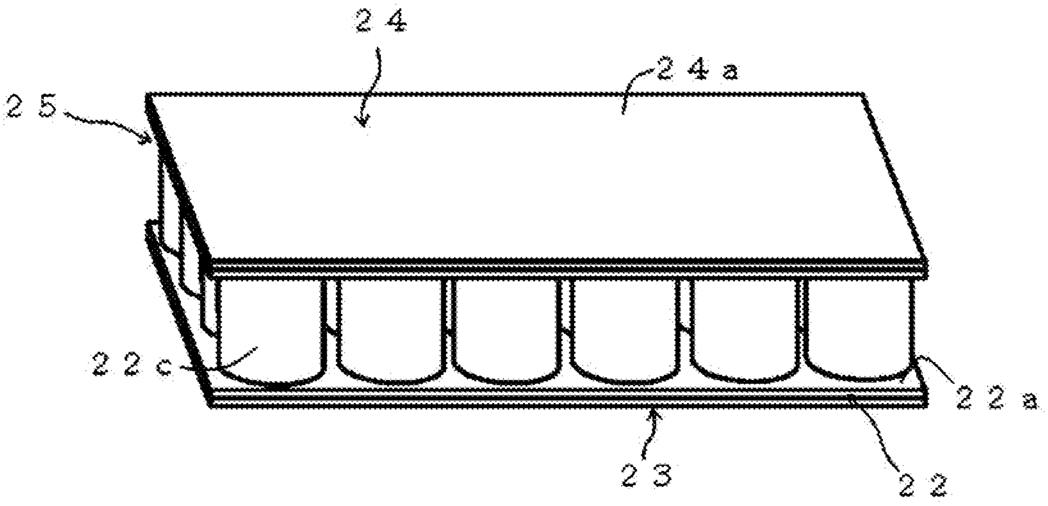
FIG. 26A is a diagram of the plate in FIG. 25B inverted after the plate cover is attached.
Figure 26B:
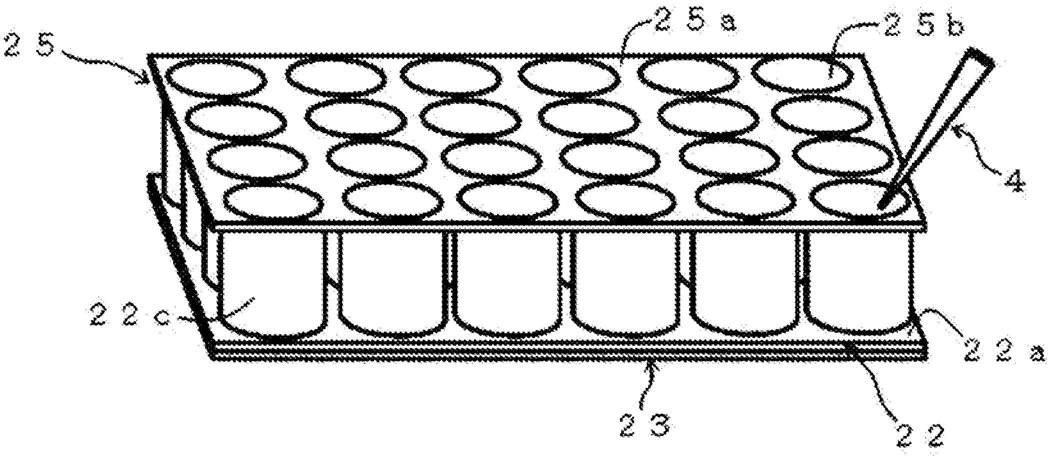
FIG. 26B is a diagram of the plate in FIG. 26A from which the spacer cover is removed.

FIG. 24 is a flowchart of a cell culture method according to the fourth embodiment of the present invention. FIG. 25A is a diagram of membrane holders placed on the upper ends of the cylinders in the spacer in FIG. 21D. FIG. 25B is a diagram of the spacer in FIG. 25A inverted after the spacer cover and the plate are attached. FIG. 25C is a longitudinal sectional view of the spacer, the cylinder in the plate, and the membrane holder in FIG. 25B. FIG. 26A is a diagram of the plate in FIG. 25B inverted after the plate cover is attached. FIG. 26B is a diagram of the plate in FIG. 26A from which the spacer cover is removed.

Figure 27A:
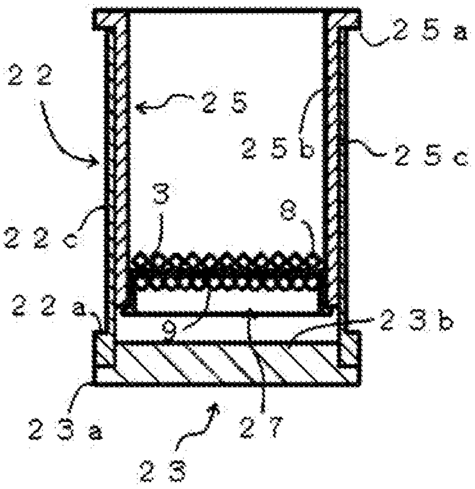
FIG. 27A is a longitudinal sectional view of one of the spacers, the cylinder in the plate, and the membrane holder in FIG. 26B.
Figure 27B:
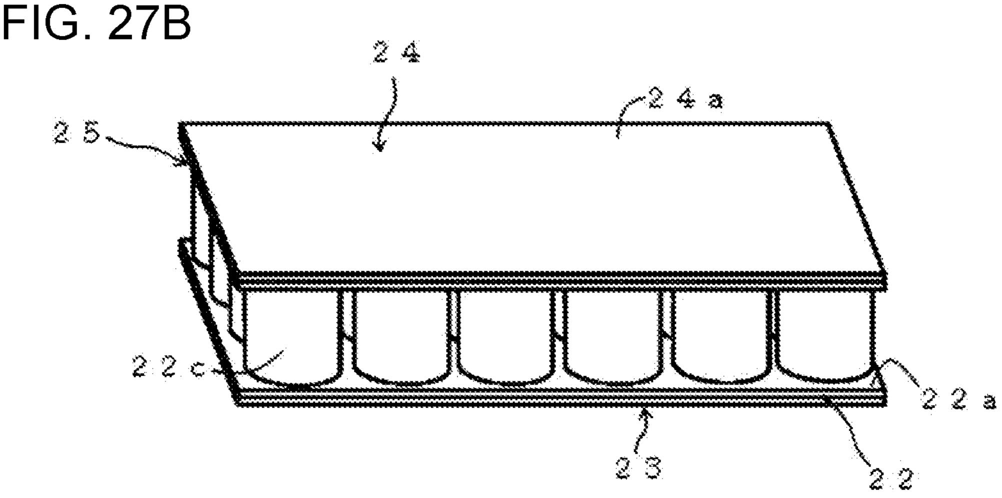
FIG. 27B is a diagram of the spacer in FIG. 26B to which the spacer cover is re-attached.
Figure 27C:
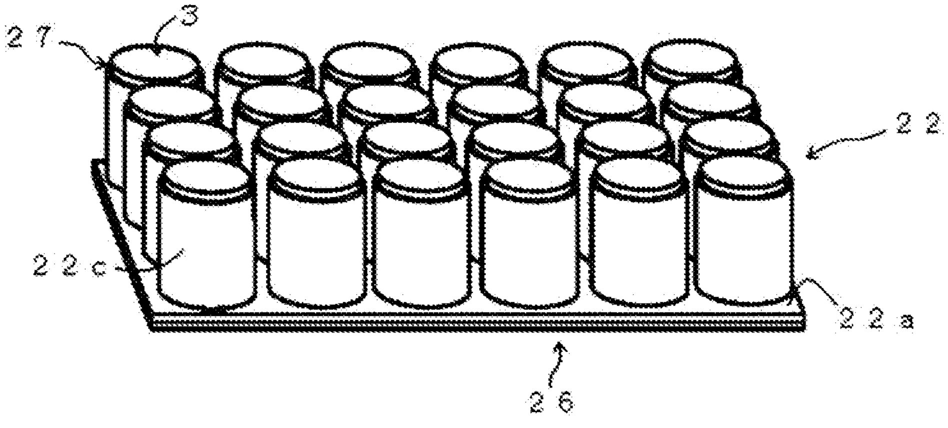
FIG. 27C is the plate to which the pusher is attached after the plate cover and the spacer cover in FIG. 27B are removed.

FIG. 27A is a longitudinal sectional view of the spacer, the cylinder in the plate, and the membrane holder in FIG. 26B. FIG. 27B is a diagram of the spacer in FIG. 26B after the spacer cover is re-attached. FIG. 27C is the plate to which the pusher is attached after the plate cover and the spacer cover in FIG. 27B are removed.

Figure 28A:
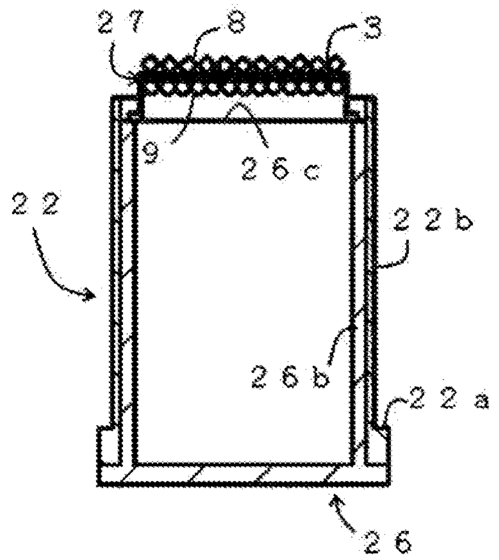
FIG. 28A is a longitudinal sectional view of the cylinder in the plate, the push portion of the pusher, and the membrane holder in FIG. 27C.
Figure 28B:
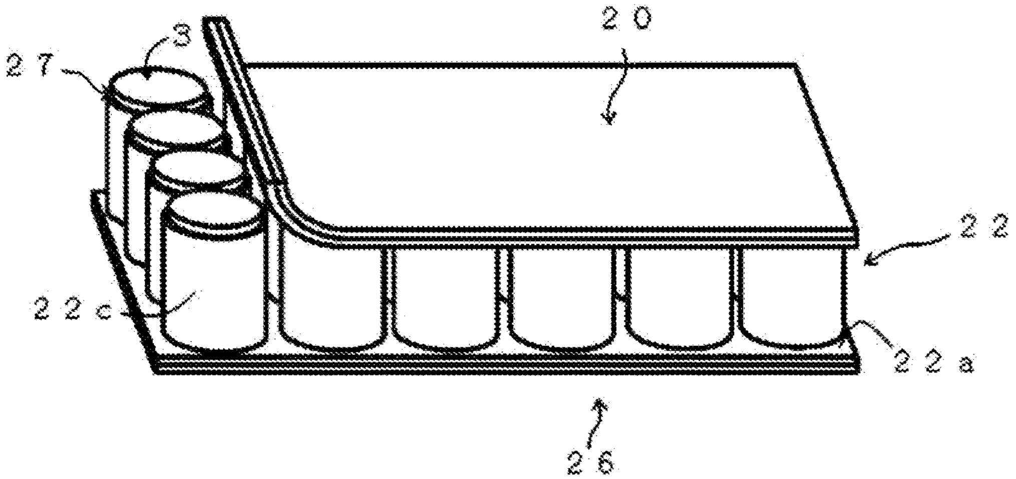
FIG. 28B is a diagram of a vascular endothelial cell sheet laid on the upper surface of the membrane holder pushed upward in the cylinder in the plate in FIG. 27C.
Figure 28C:
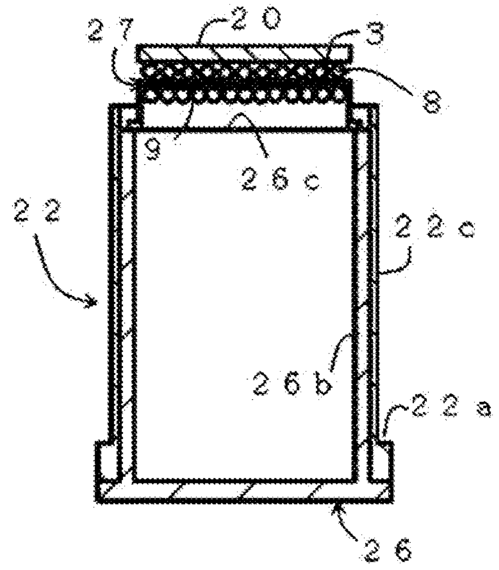
FIG. 28C is a longitudinal sectional view of the cylinder in the plate, the push portion of the pusher, and the membrane holder in FIG. 28B.
Figure 29A:
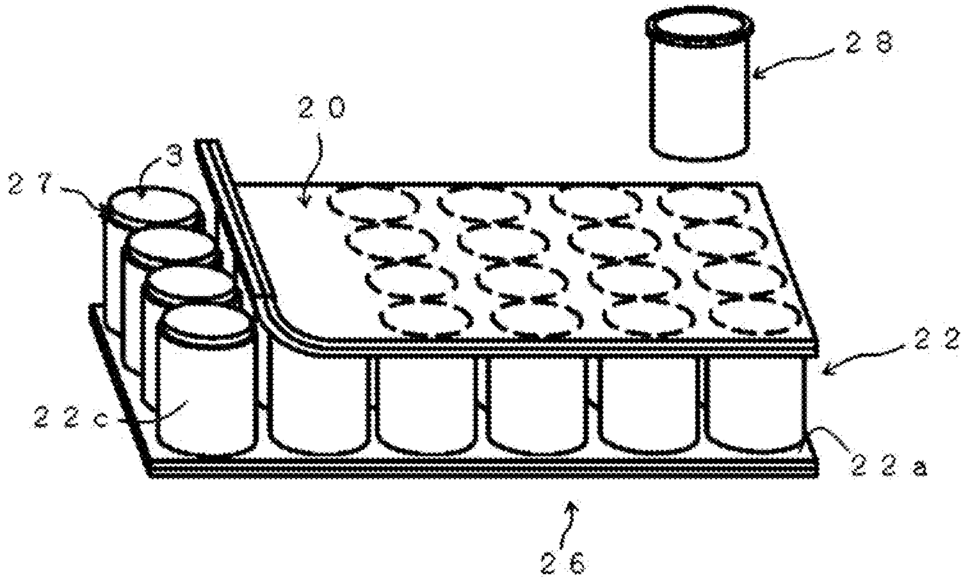
FIG. 29A is a diagram of the vascular endothelial cell sheet shown in FIG. 28B punched out by the sleeve.
Figure 29B:
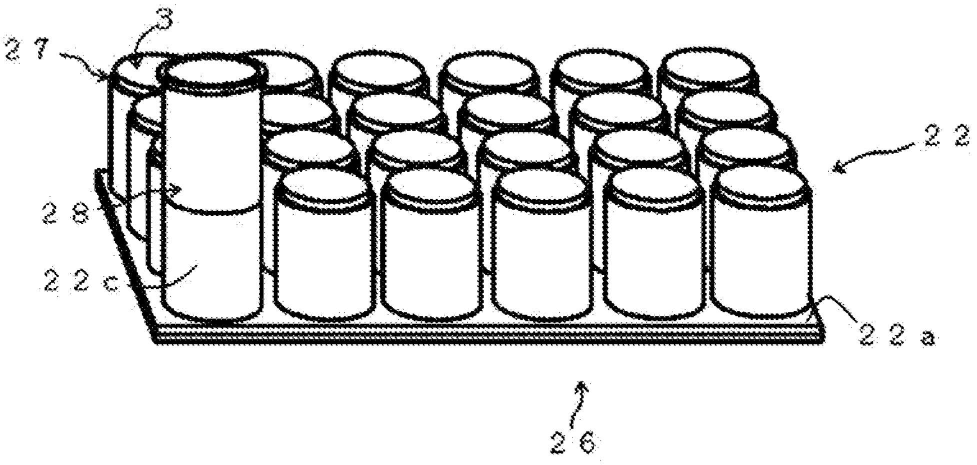
FIG. 29B is a diagram of a membrane holder placed in the sleeve that has punched out the vascular endothelial cell sheet in FIG. 29A.
Figure 30A:
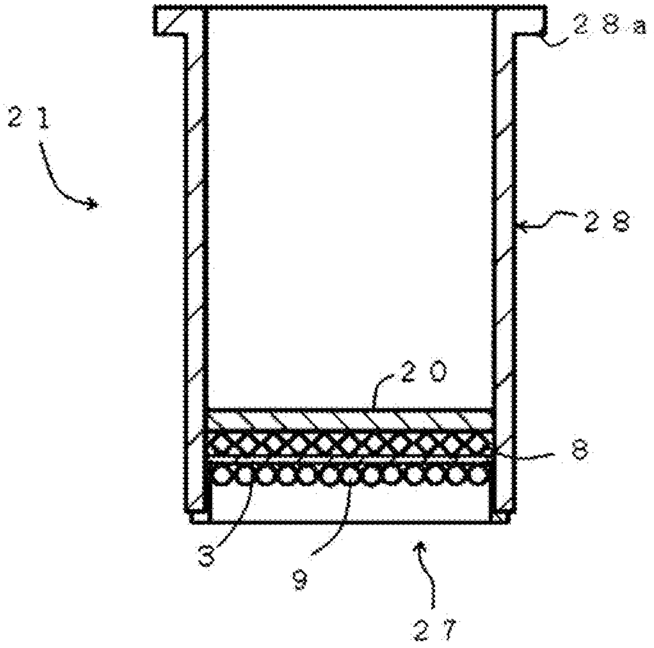
FIG. 30A is a longitudinal sectional view of a cell culture insert including the sleeve and the membrane holder shown in FIG. 29B.
Figure 30B:
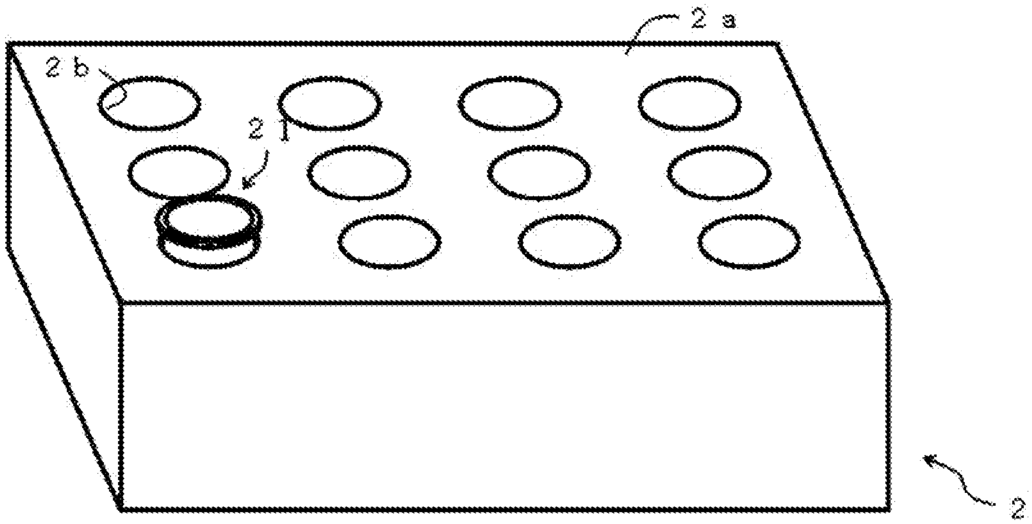
FIG. 30B is a diagram of the cell culture insert shown in FIG. 30A placed in a well in the microplate.

FIG. 28A is a longitudinal sectional view of the cylinder in the plate, the push portion of the pusher, and the membrane holder in FIG. 27C. FIG. 28B is a diagram of a vascular endothelial cell sheet laid on the upper surface of the membrane holder pushed upward in the cylinder in the plate in FIG. 27C. FIG. 28C is a longitudinal sectional view of the cylinder in the plate, the push portion of the pusher, and the membrane holder in FIG. 28B. FIG. 29A is a diagram of the vascular endothelial cell sheet shown in FIG. 28B punched out by the sleeve. FIG. 29B is a diagram of a membrane holder placed in the sleeve that has punched out the vascular endothelial cell sheet in FIG. 29A. FIG. 30A is a longitudinal sectional view of a cell culture insert including the sleeve and the membrane holder shown in FIG. 29B. FIG. 30B is a diagram of the cell culture insert shown in FIG. 30A placed in a well in the cell culture plate.

To avoid complexity in the drawings, FIG. 25A shows the membrane holders 27 alone on a subset of the cylinders. In FIGS. 25A, 25B, 26A, 26B, 27B, 27C, 28B, 29A, and 29B, one of the cylinders, one of the membrane holders, and one of the through-holes are simply denoted with the reference numerals. In FIG. 30B, one well alone is denoted with the reference numeral, and the cell culture insert is placed on simply one of the twelve wells in the cell culture plate.

FIG. 25C is a cross-sectional view of the cylinder in the spacer and part of the surrounding of its base end, the circular protrusion in the spacer cover and part of the surrounding of its base end, the cylinder in the plate and part of the surrounding of its base end, and the membrane holder placed in the cylinder in the spacer, taken along a plane including the cylinder axis of the cylinder in the plate. FIG. 27A is a cross-sectional view of the cylinder in the spacer and part of the surrounding of its base end, the circular protrusion in the plate cover and part of the surrounding of its base end, the cylinder in the plate and part of the surrounding of its base end, and the membrane holder placed in the cylinder in the spacer, taken along a plane including the cylinder axis of the cylinder in the plate. FIGS. 28A and 28C are cross-sectional views of the push portion of the pusher and part of the surrounding of its base end, the membrane holder pushed out by the pusher, and the cylinder in the plate and part of the surroundings of its base end, taken along a plane including the cylinder axis of the cylinder in the plate. FIG. 30A is a cross-sectional view of the cell culture insert taken along a plane including the cylinder axis of the sleeve.

First, as shown in FIG. 25A, the membrane holders 27 are placed at the upper ends of the cylinders 25*c* in the spacer 25 (step S1 in FIG. 24). Subsequently, the plate 22 having the cylinders 22*c* facing downward is placed on the spacer 25 to cause the base 22*a* parallel to the base 25*a* to cover all the cylinders 25*c* with all the cylinders 22*c*. The spacer cover 24 is then attached to the spacer 25 to fit the circular protrusions 24*b* into the cylinders 25*c* from the lower surface of the base 25*a* (step S2 in FIG. 24). Thereafter, as shown in FIG. 25B, a suspended cell culture medium (not shown) is injected into the cylinders 25*c* in the spacer 25 through the through-holes 22*b* in the plate 22 using the pipette 4 and seeded with the astrocyte 9 (refer to FIG. 25C) (steps S3 and S4 in FIG. 24). The astrocyte 9 is then cultured for several days until forming into a layer (step S5 in FIG. 24) with the temperature of the cell culture medium maintained at, for example, 33° C.

After the cell culture medium is removed in the state in FIG. 25B, and the plate cover 23 is attached to the plate 22 to have the circular protrusions 23*b* fitted to the through-holes 22*b* from the lower surface of the base 22*a*, the plate 22 is inverted together with the plate cover 23, the spacer cover 24, and the spacer 25 as shown in FIG. 26A (step S6 in FIG. 24). As shown in FIG. 26B, the spacer cover 24 is then removed, and the cell culture medium is injected into the cylinders 25*c* in the spacer 25 using the pipette 4 to seed the cell culture medium with the pericyte 8 (refer to FIG. 27A) (steps S7 and S8 in FIG. 24). The spacer cover 24 is re-attached to the spacer 25 as shown in FIG. 27B, and the pericyte 8 is cultured for several days until forming into a layer with the temperature inside the cylinders 25*c* in the spacer 25 maintained at, for example, 33° C. The cell culture medium is removed after the pericyte 8 is grown into a layer (steps S9 and S10 in FIG. 24). Thus, the astrocyte 9 that has grown into a layer on the inner surface of the porous membrane 3 has cell projections extending through pores in the porous membrane 3 to a position near the pericyte 8 on the outer surface of the porous membrane 3 as shown in FIG. 28A.

Thus, the insides of the through-holes 22*b* in the plate 22 and the cylinders 25*c* in the spacer 25 are used as cell culture chambers. With the membrane holder 27 placed inside, the cell culture chamber is partitioned into two by the porous membrane 3. In the cell culture device according to the present embodiment, the second inner wall 27*b* (refer to FIG. 22D) in the tubular membrane holder 27, and the inner wall of each of the through-hole 25*b* and the cylinder 25*c* in the base 25*a* in the spacer 25, or the second inner wall 27*b* in the membrane holder 27, and the inner wall of each of the through-hole 22*b* and the cylinder 22*c* in the base 22*a* in the plate 22 thus define a pair of upper and lower cell culture chambers divided by the porous membrane 3. Multiple upper cell culture chambers are integrally coupled together, and lower cell culture chambers are integrally coupled together.

As shown in FIG. 27C, when the pusher 26 is moved toward the plate 22 to place the push plate 26*a* into contact with the base 22*a* after the plate cover 23, the spacer cover 24, and the spacer 25 are removed and the push portions 26*b* in the pusher 26 are received in the through-holes 22*b* in the plate 22, the membrane holders 27 attached to the distal end faces 26*c* (refer to FIG. 28A) of the push portions 26*b* are pushed out of the cylinders 22*c* (step S11 in FIG. 24).

As shown in FIGS. 28B and 28C, the cell sheet 20 of the vascular endothelial cell 7 is laid over the upper surfaces of the membrane holders 27 pushed out of the cylinders 22*c* in the plate 22 in FIG. 27C (step S12 in FIG. 24). The cell sheet 20 of the vascular endothelial cell 7 shown in FIG. 28B is punched out from above by the sleeve 28 as shown in FIG. 29A, and then, the scrap of the cell sheet 20 is removed (step S13 in FIG. 24). The sleeve 28 is then pushed onto the corresponding membrane holder 27 to have the membrane holder 27 at its distal end as shown in FIG. 29B (step S14 in FIG. 24). Thus, the membrane holder 27 and the sleeve 28 are integrated. As shown in FIG. 30A, three cell layers including the cell sheet 20 of the vascular endothelial cell 7, the pericyte 8, and the astrocyte 9 are formed at the bottom of the cell culture insert 21. The cell culture insert 21 is removed from the corresponding push portion 26*b* in the pusher 26 and placed at the corresponding well 2*b* in the microplate 2 as shown in FIG. 30B (step S15 in FIG. 24). The vascular endothelial cell 7 is cultured for several days (step S16 in FIG. 24) with the temperature inside the cell culture inserts 21 maintained at, for example, 33° C.

The cell culture device according to the present embodiment simultaneously performs, on the multiple porous membranes 3 or the multiple membrane holders 27, inversion of the porous membranes 3, removal of the membrane holders 27 from inside the through-holes 22*b* in the plate 22, and placement of the vascular endothelial cells 7 on top of the pericytes 8. The device can thus fabricate multiple BBB models in a short time.

Figure 31:
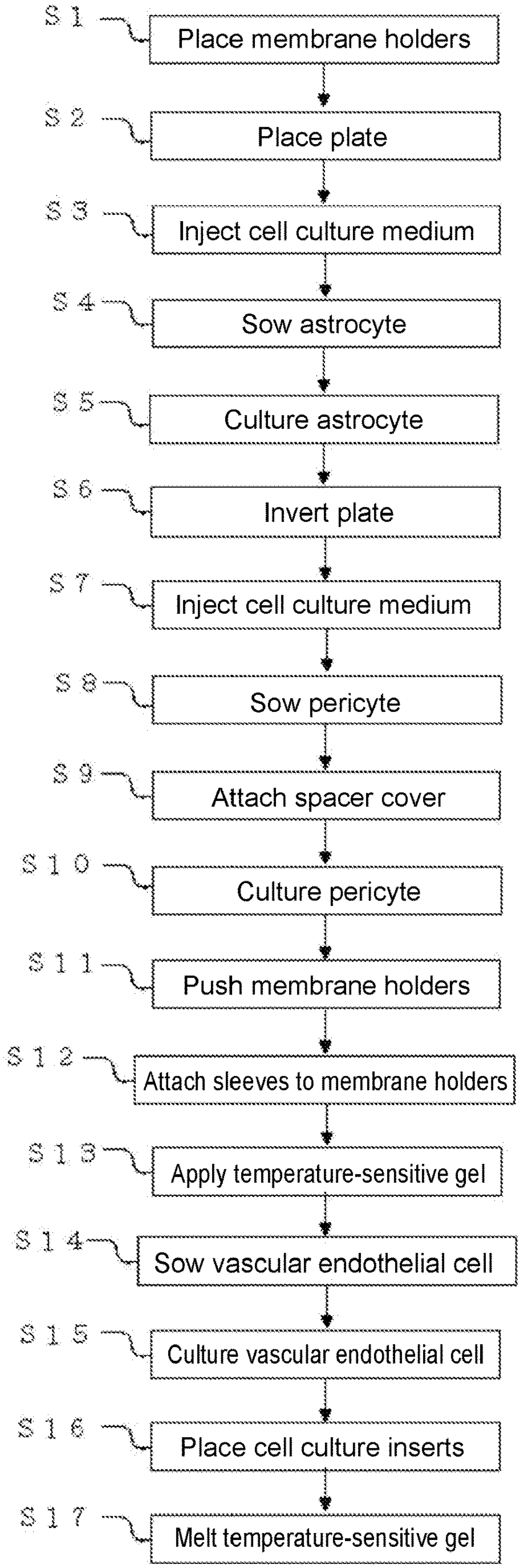
FIG. 31 is a flowchart of a modification of the flowchart shown in FIG. 24.
Figure 32A:
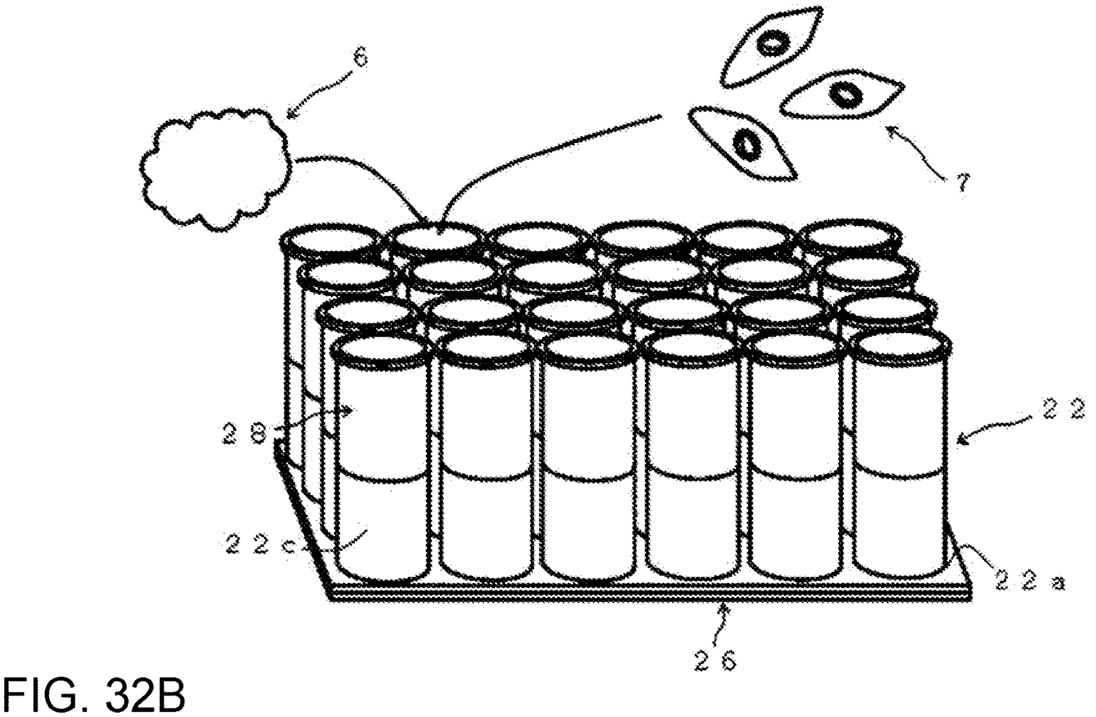
FIG. 32A is a diagram of the membrane holders in FIG. 27C receiving the sleeves.
Figure 32B:
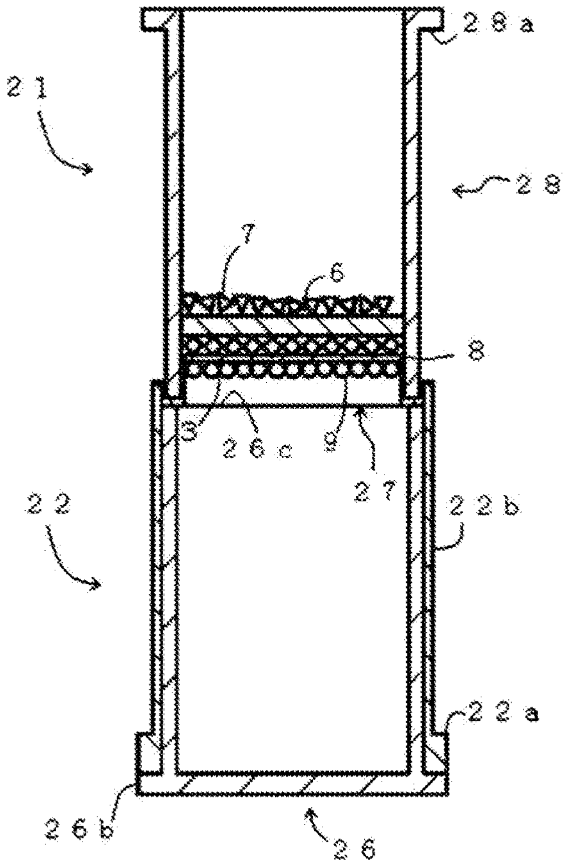
FIG. 32B is a longitudinal sectional view of the cell culture insert including the cylinder in the plate, the push portion of the pusher, the sleeve, and the membrane holder shown in FIG. 32A.

A cell culture method according to a modification of the present embodiment will now be described with reference to FIGS. 31, 32A, and 32B. FIG. 31 is a flowchart of a modification of the flowchart shown in FIG. 24. FIG. 32A is a diagram of the membrane holders in FIG. 27C receiving the sleeves. FIG. 32B is a longitudinal sectional view of the cell culture insert including the cylinder in the plate, the push portion of the pusher, the sleeve, and the membrane holder shown in FIG. 32A. To avoid complexity in the drawings, one of the cylinders and one of the sleeves are simply denoted with the reference numerals in FIG. 32A. FIG. 32B is a cross-sectional view of the push portion of the pusher and part of the surrounding of its base end, the membrane holder pushed by the pusher, and the cylinder in the plate and part of the surroundings of its base end, taken along a plane including the cylinder axis of the cylinder in the plate. In the processes shown in FIG. 31, steps S1 to S11 are the same as steps S1 to S11 in FIG. 24, and are not described.

More specifically, after steps S1 to S11, each sleeve 28 is pushed onto the corresponding membrane holder 27 in FIG. 27C to have the membrane holder 27 at its distal end as shown in FIG. 32A (step S12 in FIG. 31). Subsequently, the temperature-sensitive gel 6 that melts at or over a temperature at which the vascular endothelial cell stops growing (e.g., 37° C.) is applied to the cell layer of the pericyte 8 in each cell culture insert 21 (step S13 in FIG. 31). The vascular endothelial cell 7 is then embedded in the temperature-sensitive gel 6 (step S14 in FIG. 31). The vascular endothelial cell 7 is cultured for several days with the temperature inside the cell culture insert 21 maintained at, for example, 33° C. (step S15 in FIG. 31).

Thus, as shown in FIG. 32B, three cell layers including the vascular endothelial cell 7 embedded in the temperature-sensitive gel 6, the pericyte 8, and the astrocyte 9 are formed at the bottom of the cell culture insert 21. The cell culture insert 21 is removed from the corresponding push portion 26*b* in the pusher 26 and placed at the corresponding well 2*b* in the microplate 2 as shown in FIG. 30B (step S16 in FIG. 31). When the temperature inside the cell culture insert 21 is raised to 37° C., the vascular endothelial cell 7 stops growing and the temperature-sensitive gel 6 melts (step S17 in FIG. 31). The vascular endothelial cell 7 then comes into contact with the pericyte 8. The temperature inside the cell culture insert 21 is maintained at 33° C. to restart culture of the vascular endothelial cell 7. This completes a three-layer BBB model including the vascular endothelial cell 7, the pericyte 8, and the astrocyte 9.

Although the pericyte 8 controls differentiation or growth of the vascular endothelial cell 7, the pericyte 8 cannot perform such functions when the vascular endothelial cell 7 is embedded in the temperature-sensitive gel 6 without being in contact with the pericyte 8. More specifically, the cell culture method shown in FIG. 31 maintains the temperature inside the cell culture insert 21 at the temperature at which the temperature-sensitive gel 6 remains unmelted, and thus maintains the vascular endothelial cell 7, the pericyte 8, and the astrocyte 9 formed at the bottom of the cell culture insert 21 in steps S1 to S15 shown in FIG. 31 to be laminated for a long time. The use of the temperature-sensitive gel 6 eliminates preparation of the vascular endothelial cell sheet and thus can eliminate a process of forming the cell sheet. Thus, the above cell culture method can enhance mass production of BBB models including the three cell layers.

Fifth Embodiment

Figure 33A:
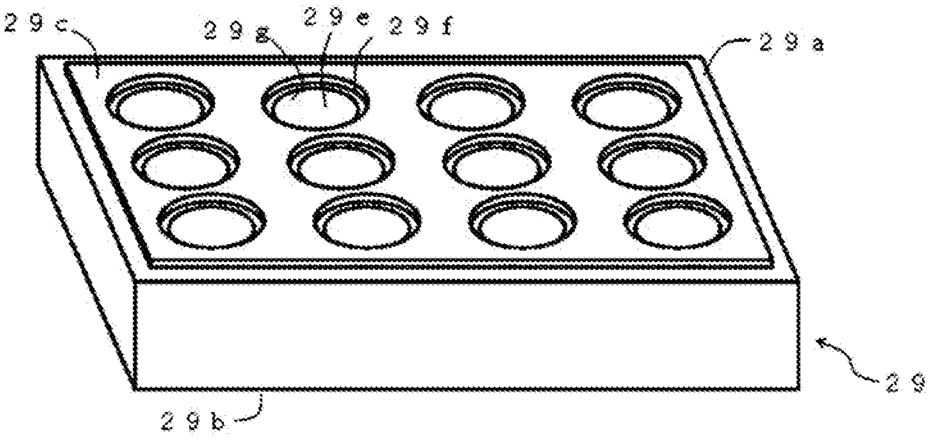
FIG. 33A is an external perspective view of the cell culture plate.
Figure 33B:
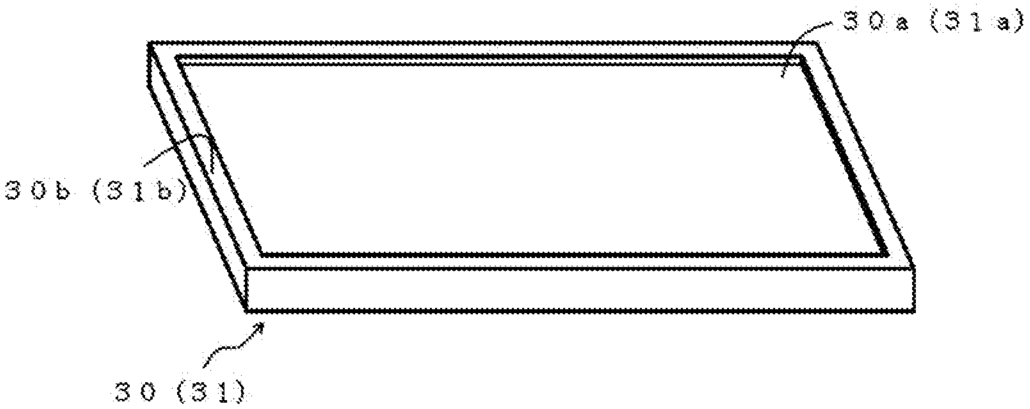
FIG. 33B is an external perspective view of the upper cover (lower cover)
Figure 33C:
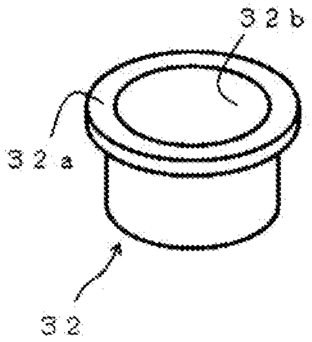
FIG. 33C is an external perspective view of the cell culture insert.

With reference to FIGS. 33A to 33C, a cell culture device according to a fifth embodiment of the present invention will now be described. FIG. 33A is an external perspective view of a cell culture plate. FIG. 33B is an external perspective view of a first plate cover (a second plate cover). FIG. 33C is an external perspective view of a cell culture insert. To avoid complexity in the drawings, one well alone is denoted with the reference numeral in FIG. 33A. The first plate cover and the second plate cover have the same shape as viewed in plan and thus are denoted with their reference numerals in FIG. 33B.

As shown in FIGS. 33A to 33C, the cell culture device according to the present embodiment includes a cell culture plate 29 including circular through-holes 29*e* serving as the inner walls of cell culture chambers, a first plate cover 30 and a second plate cover 31 placed over and under the cell culture plate 29 serving as cell culture chamber covers, and cell culture inserts 32.

As shown in FIG. 33A, the cell culture plate 29 has a substantially rectangular prism shape, and has an upper surface 29*a* having twelve (3 columns by 4 rows) through-holes 29*e* serving as wells, and a lower surface 29*b*. The upper surface 29*a* receives a first rectangular protrusion 29*c*, and the lower surface 29*b* receives a second rectangular protrusion 29*d* (refer to FIG. 35B).

As shown in FIG. 33B, the first plate cover 30 includes a rectangular recess 30*a* and a frame-shaped protrusion 30*b* surrounding the recess 30*a*, and the second plate cover 31 includes a rectangular recess 31*a* and a frame-shaped protrusion 31*b* surrounding the recess 31*a*. When the recess 30*a* or 31*a* is located on the upper surface 29*a* of the cell culture plate 29, the protrusion 30*b* or 31*b* can accommodate the first rectangular protrusion 29*c* or the second rectangular protrusion 29*d*.

As shown in FIG. 33C, the cell culture insert 32 includes a cylinder having one end with a flange 32*a*. The porous membrane 3 is fixed to the inner surface of the other end of the cylinder through thermal bonding. Each through-hole 29*e* in the cell culture plate 29 has a stepped structure including a large-diameter portion 29*f* and a small-diameter portion 29*g*. The large-diameter portion 29*f* has an inner diameter larger than the outer diameter of the flange 32*a*, and has a depth to receive the flange 32*a* inside. The small-diameter portion 29*g* has an inner diameter smaller than the outer diameter of the flange 32*a*, and has a depth to receive the portion of the cell culture insert 32 other than the flange 32*a* and to maintain the end face of the cell culture insert 32 receiving the porous membrane 3 apart from the bottom surface with the flange 32*a* hooked on the large-diameter portion 29*f*.

The cell culture insert 32 including a first inner wall 32*b* (refer to FIG. 33C) as the inner wall of the cell culture chamber is used as the cell culture chamber as described below, together with the cell culture plate 29 having multiple through-holes 29*e* serving as the inner walls of the cell culture chambers.

A cell culture method according to one or more embodiments of the present invention for fabricating three-layer BBB models including a vascular endothelial cell, a pericyte, and an astrocyte using a cell culture device according to the present embodiment will now be described with reference to FIGS. 34 to 37C.

Figure 34:
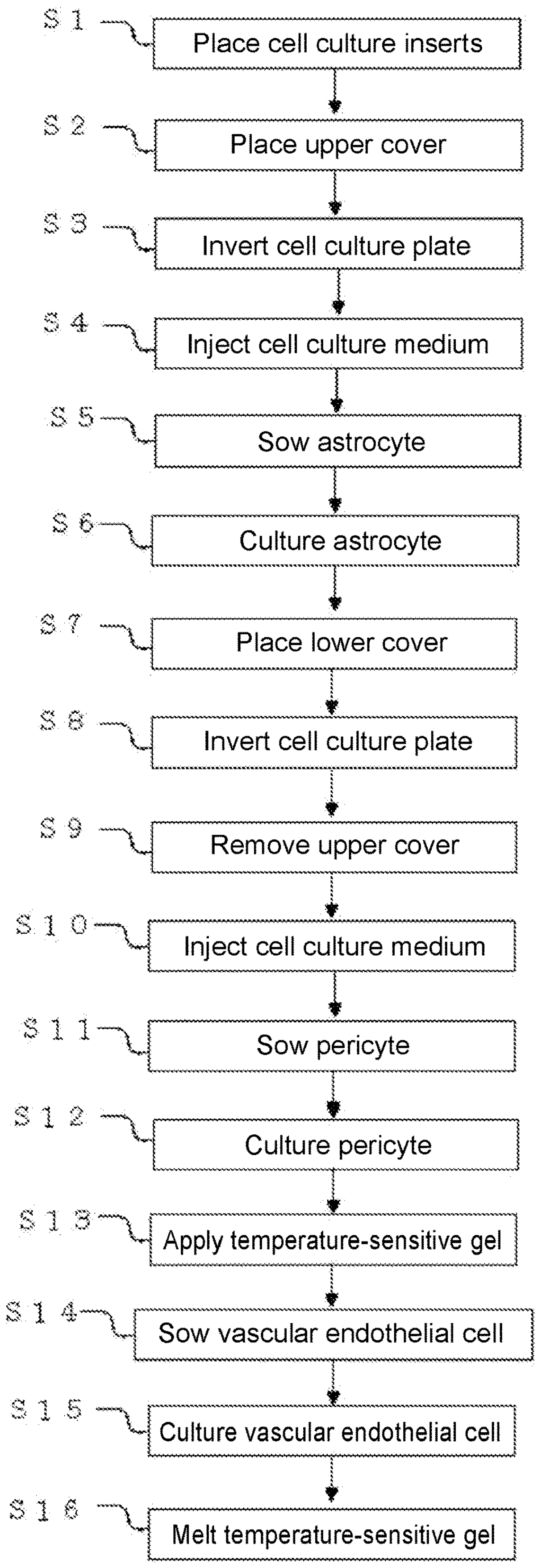
FIG. 34 is a flowchart of a cell culture method according to a fifth embodiment of the present invention.
Figure 35A:
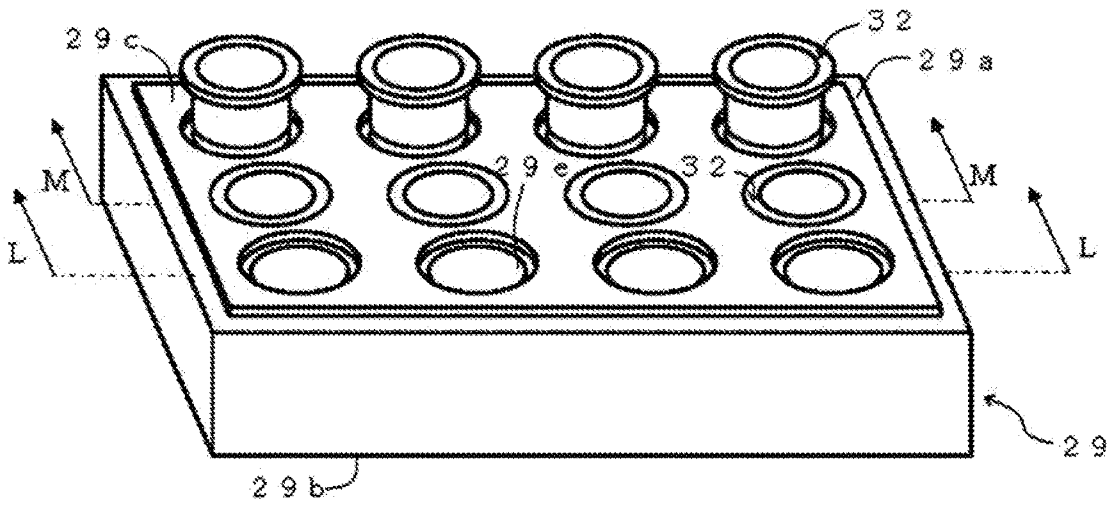
FIG. 35A is a diagram of the cell culture inserts shown in FIG. 33C placed in through-holes in a cell culture plate.
Figure 35B:
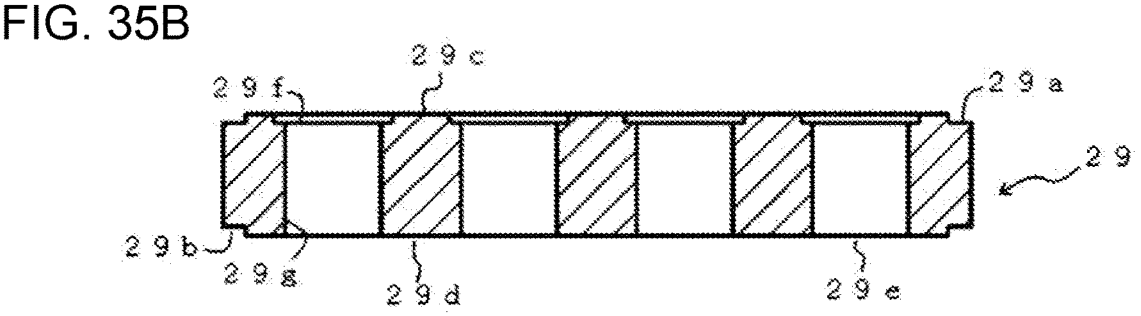
FIG. 35B is a cross-sectional view taken along line L-L as viewed in the direction indicated by arrows in FIG. 35A.
Figure 35C:
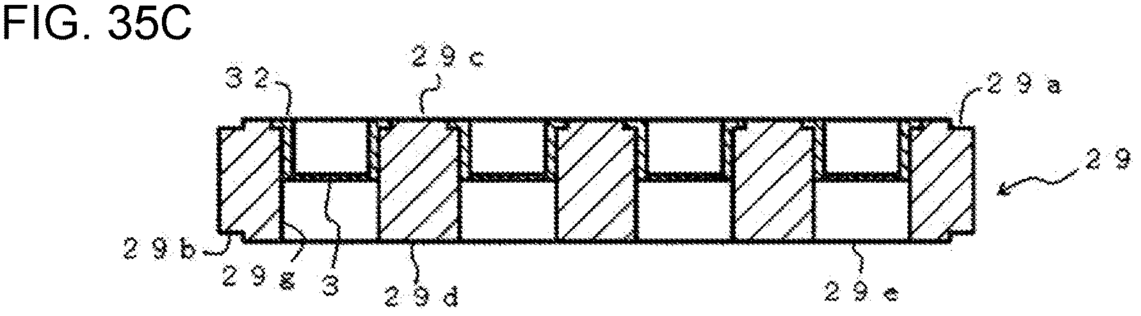
FIG. 35C is a cross-sectional view taken along line M-M as viewed in the direction indicated by arrows in FIG. 35A.
Figure 36A:
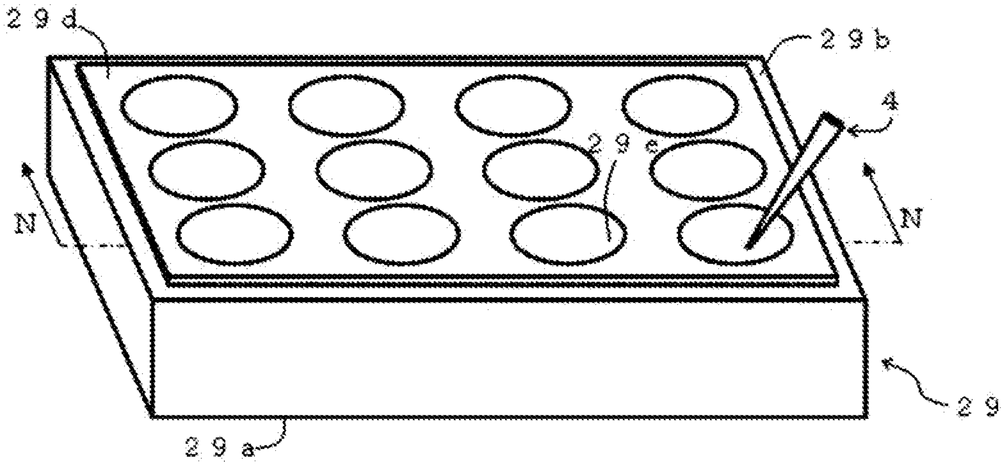
FIG. 36A is a diagram of the cell culture plate with the through-holes receiving the cell culture inserts seeded with cells.
Figure 36B:
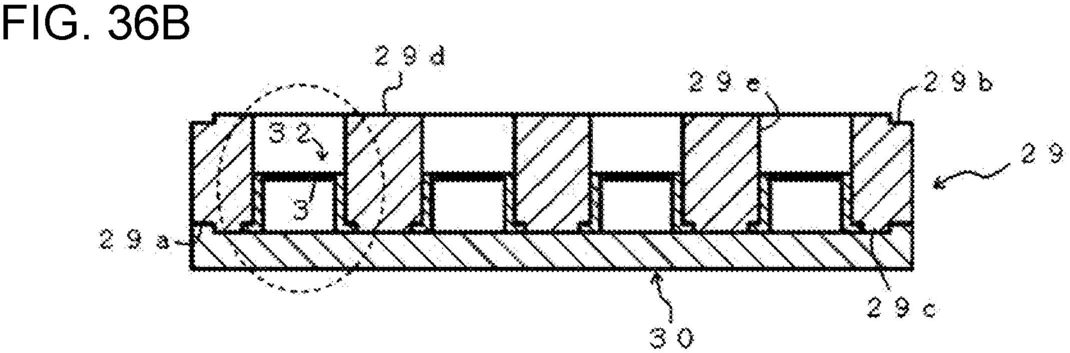
FIG. 36B is a cross-sectional view taken along line N-N as viewed in the direction indicated by arrows in FIG. 36A.
Figure 36C:
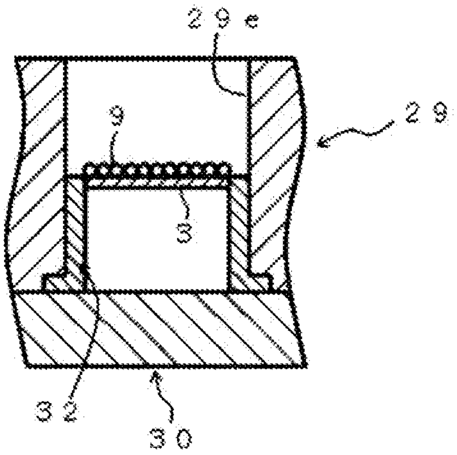
FIG. 36C is an enlarged view of a portion encircled with the dotted line in FIG. 36B.
Figure 37A:
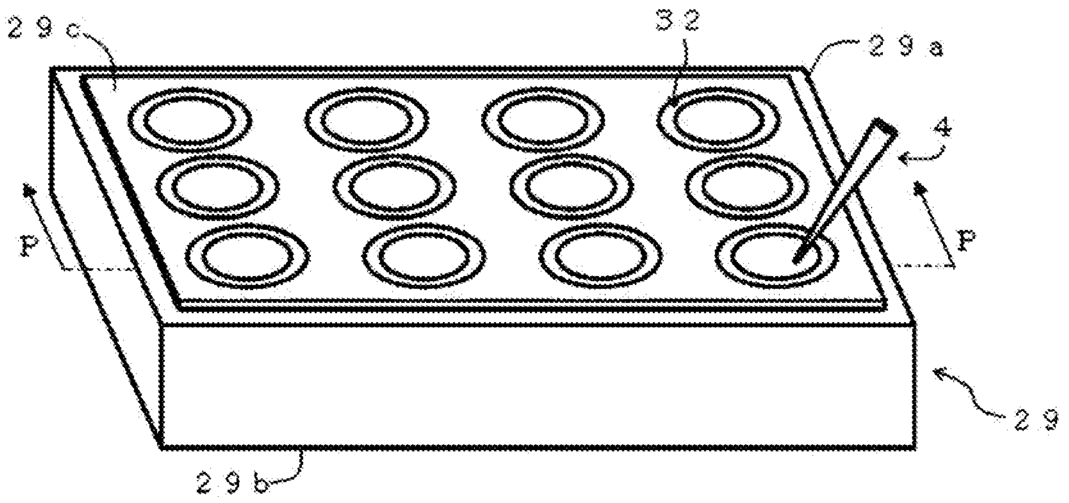
FIG. 37A is a diagram of the cell culture plate with the through-holes inverted from the position in FIG. 36A and receiving the cell culture inserts seeded with the cells.
Figure 37B:
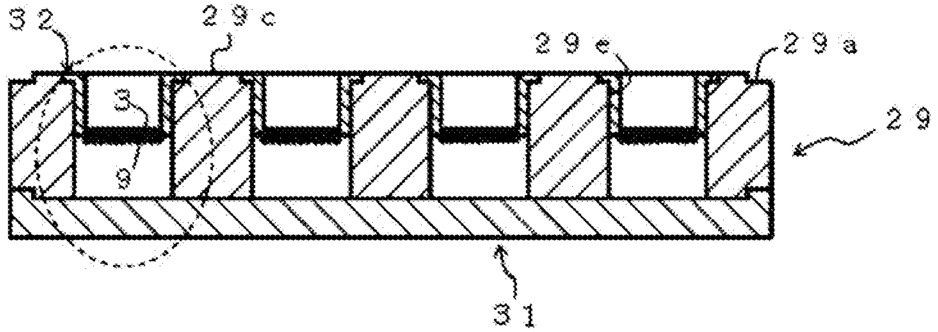
FIG. 37B is a cross-sectional view taken along line P-P as viewed in the direction indicated by arrows in FIG. 37A.
Figure 37C:
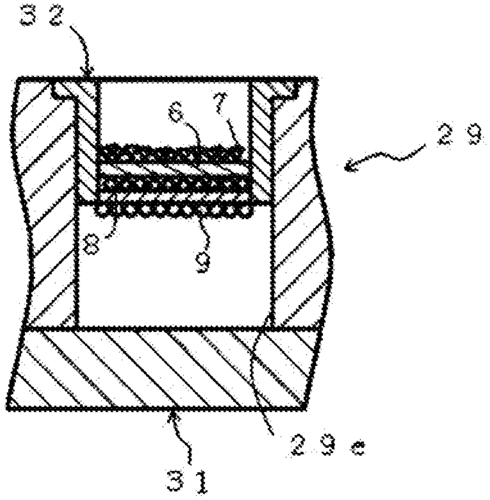
FIG. 37C is an enlarged view of a portion encircled with the dotted line in FIG. 37B.

FIG. 34 is a flowchart of a cell culture method according to the fifth embodiment of the present invention. FIG. 35A is a diagram of the cell culture inserts shown in FIG. 33C placed in the through-holes in the cell culture plate. FIG. 35B is a cross-sectional view taken along line L-L as viewed in the direction indicated by arrows in FIG. 35A. FIG. 35C is a cross-sectional view taken along line M-M as viewed in the direction indicated by arrows in FIG. 35A. FIG. 36A isa diagram of the cell culture plate with the through-holes receiving the cell culture inserts seeded with cells. FIG. 36B is a cross-sectional view taken along line N-N as viewed in the direction indicated by arrows in FIG. 36A. FIG. 36C is an enlarged view of a portion encircled with the dotted line in FIG. 36B. FIG. 37A isa diagram of the cell culture plate with the through-holes inverted from the position in FIG. 36A and receiving the cell culture inserts seeded with the cells. FIG. 37B is a cross-sectional view taken along line P-P as viewed in the direction indicated by arrows in FIG. 37A. FIG. 37C is an enlarged view of a portion encircled with the dotted line in FIG. 37B.

First, as shown in FIGS. 35A and 35C, the cell culture insert 32 is placed in a through-hole 29*e* while placing the flange 32*a* on the large-diameter portion 29*f* of the cell culture plate 29 (step S1 in FIG. 34). After the first plate cover 30 is placed on the upper surface 29*a* of the cell culture plate 29, as shown in FIG. 36B, the cell culture plate 29 integral with the first plate cover 30 is inverted (steps S2 and S3 in FIG. 34). As shown in FIG. 36A, a cell culture medium (not shown) is then injected into the through-holes 29*e* in the cell culture plate 29 using the pipette 4 and seeded with the astrocyte 9 (steps S4 and S5 in FIG. 34). The astrocyte 9 in FIG. 36C is then cultured for several days until forming into a layer (step S6 in FIG. 34) with the temperature inside the through-holes 29*e* maintained at, for example, 33° C. The second plate cover 31 is then placed on the lower surface 29*b* of the cell culture plate 29, and the cell culture plate 29 integral with the first plate cover 30 and the second plate cover 31 is inverted (steps S7 and S8 in FIG. 34).

As shown in FIG. 37B, after the first plate cover 30 is removed from the upper surface 29*a* of the cell culture plate 29, the cell culture medium (not shown) is injected into the cell culture inserts 32 placed in the through-holes 29*e* in the cell culture plate 29 using the pipette 4 as shown in FIG. 37A and seeded with the pericyte 8 (steps S9 to S11 in FIG. 34). The pericyte 8 is then cultured for several days until forming into a layer with the temperature inside the cell culture inserts 32 maintained at, for example, 33° C. The cell culture medium is removed after the pericyte 8 is grown into a layer (step S12 in FIG. 34). Thus, the astrocyte 9 that has grown into a layer on the outer surface of the porous membrane 3 has cell projections extending through pores in the porous membrane 3 to a position near the pericyte 8 on the inner surface of the porous membrane 3.

When the insides of the through-holes 29*e* in the cell culture plate 29 are used as cell culture chambers and the cell culture inserts 32 are placed in the through-holes 29*e*, each cell culture chamber is partitioned into two by the porous membrane 3. In the cell culture device according to the present embodiment, the first inner wall 32*b* (refer to FIG. 33C) of each tubular cell culture insert 32 and the inner wall of the corresponding through-hole 29*e* formed in the cell culture plate 29 thus define a pair of upper and lower cell culture chambers divided by the porous membrane 3. Multiple upper cell culture chambers are integrally coupled together, and lower cell culture chambers are integrally coupled together.

Subsequently, the temperature-sensitive gel 6 that melts at or over a temperature (e.g., 37° C.) at which the vascular endothelial cell stops growing is applied to the cell layer of the pericyte 8 (step S13 in FIG. 34). In addition, the vascular endothelial cell 7 is embedded in the temperature-sensitive gel 6 (step S14 in FIG. 34). The vascular endothelial cell 7 is then cultured for several days with the temperature inside the cell culture inserts 32 maintained at, for example, 33° C. (step S15 in FIG. 34).

Thus, as shown in FIG. 37C, three cell layers including the vascular endothelial cell 7 embedded in the temperature-sensitive gel 6, the pericyte 8, and the astrocyte 9 are formed at the bottoms of the cell culture inserts 32. The cell culture inserts 32 are then removed from the through-holes 29*e* in the cell culture plate 29 and placed in the wells 2*b* in the microplate 2 (refer to FIG. 1C). When the temperature inside the cell culture inserts 32 is raised to 37° C., the vascular endothelial cell 7 stops growing, the temperature-sensitive gel 6 melts (step S16 in FIG. 34), and the vascular endothelial cell 7 comes into contact with the pericyte 8. The temperature inside the cell culture inserts 32 is then maintained at 33° C. to restart culture of the vascular endothelial cell 7. This completes three-layer BBB models including the vascular endothelial cell 7, the pericyte 8, and the astrocyte 9.

Thus, in the cell culture device according to the present embodiment, after the first plate cover 30 is placed on the upper surface 29*a* of the cell culture plate 29 on which the cell culture inserts 32 are placed in the through-holes 29*e* to have the bottoms facing downward, the cell culture plate 29 is inverted together with the first plate cover 30, and the astrocyte 9 and the cell culture medium 5 are sown into the through-holes 29*e*. The inner walls of the through-holes 29*e* then prevent leakage of the cell culture medium 5 and the astrocyte 9. The cell culture device according to the present embodiment thus facilitates culture of the astrocyte 9 on the outer surface of the porous membrane 3. In addition, when the second plate cover 31 is placed on the lower surface 29*b* of the cell culture plate 29, and the cell culture plate 29 is inverted together with the first plate cover 30 and the second plate cover 31, the cell culture inserts 32 are held in the through-holes 29*e* to have the bottoms facing downward. The cell culture device according to the present embodiment thus facilitates sowing the pericyte 8 and the vascular endothelial cell 7 into the cell culture inserts 32 with the cell culture medium 5, or culture of the vascular endothelial cell 7 and the pericyte 8 in the cell culture inserts 32. The cell culture plate 29 receiving the second plate cover 31 functions as the microplate 2. Thus, the cell culture device according to the present embodiment can efficiently fabricate multiple BBB models.

The cell culture method according to the present embodiment includes a process of applying the temperature-sensitive gel 6 to the cell layer of the pericyte 8. The cell culture method thus eliminates preparation of the cell sheet 20 of the vascular endothelial cell 7 and thus can eliminate the process of fabricating the cell sheet.

Sixth Embodiment

Figure 38A:
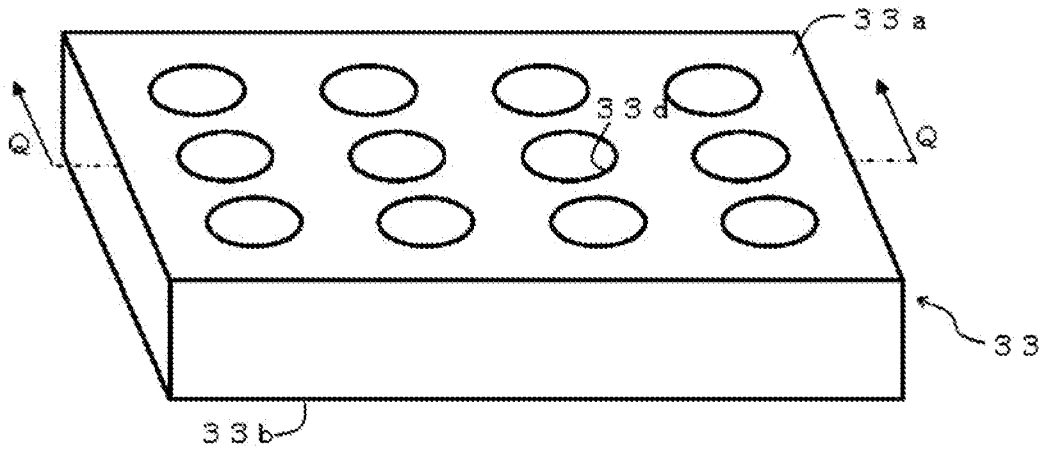
FIGS. 38A and 38C are external perspective views of the cell culture plate.
Figure 38B:
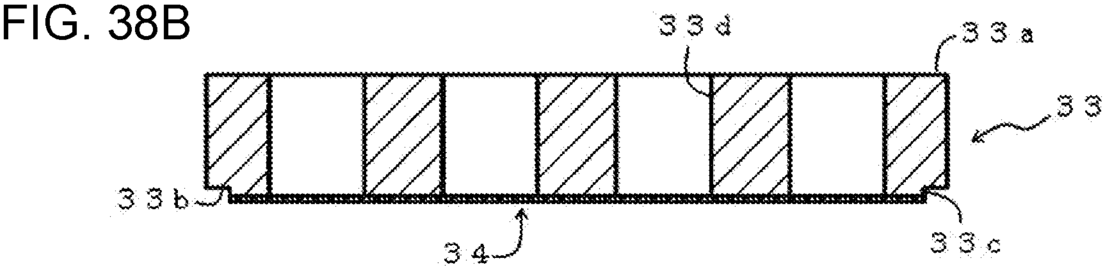
FIG. 38B is a cross-sectional view taken along line Q-Q as viewed in the direction indicated by arrows in FIG. 38A.
Figure 38C:
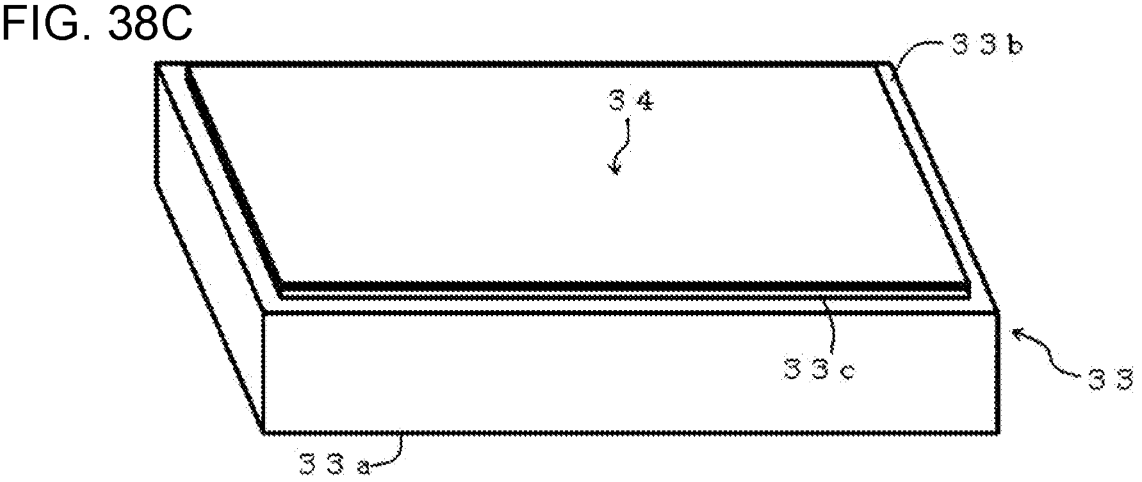
Figure 39A:
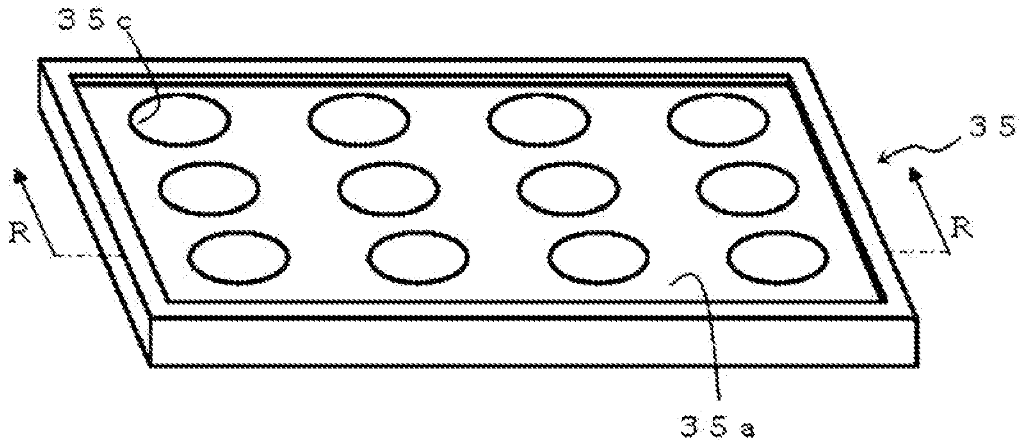
FIG. 39A is an external perspective view of a first bottom cover.
Figure 39B:
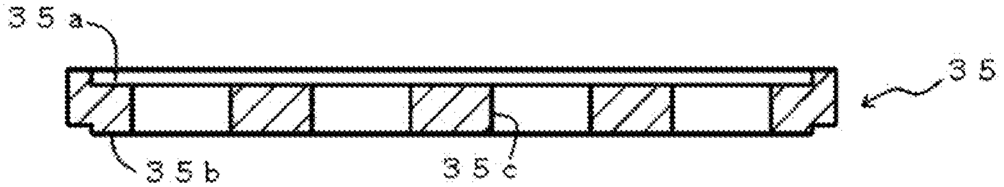
FIG. 39B is a cross-sectional view taken along line R-R as viewed in the direction indicated by arrows in FIG. 39A.
Figure 39C:
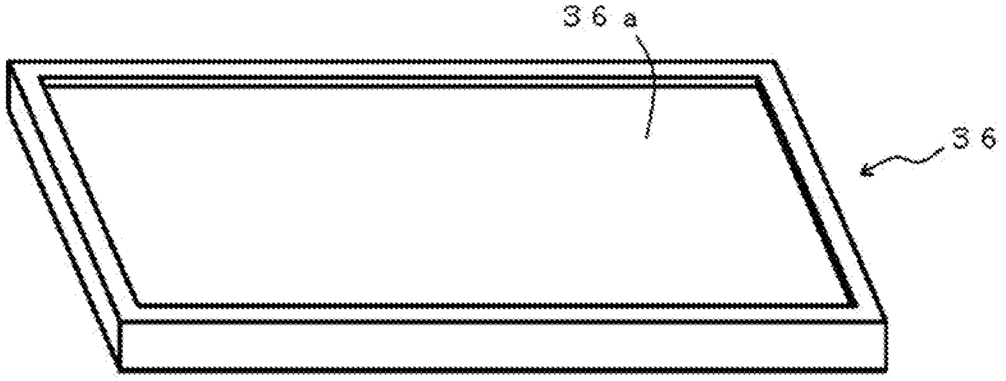
FIG. 39C is an external perspective view of a second bottom cover.

A cell culture device according to a sixth embodiment of the present invention will now be described with reference to FIGS. 38A to 39C. FIGS. 38A and 38C are external perspective views of a cell culture plate. FIG. 38B is a cross-sectional view taken along line Q-Q as viewed in the direction indicated by arrows in FIG. 38A. FIG. 39A is an external perspective view of a first bottom cover. FIG. 39B is a cross-sectional view taken along line R-R as viewed in the direction indicated by arrows in FIG. 39A. FIG. 39C is an external perspective view of a second bottom cover.

As shown in FIGS. 38A to 38C and 39A to 39C, the cell culture device according to the present embodiment includes a cell culture plate 33 including circular through-holes 33*d* serving as the inner walls of cell culture chambers, a first bottom cover 35 placed on a bottom surface 33*b* of the cell culture plate 33, and a second bottom cover 36 placed on a bottom board 35*a* of the first bottom cover 35 and serving as a cell culture chamber cover.

As shown in FIGS. 38A to 38C, the cell culture plate 33 has a substantially rectangular prism shape and has an upper surface 33*a* having twelve (3 columns by 4 rows) through-holes 33*d* serving as wells. A sheet 34 including the porous membrane 3 is attached to or thermally bonded to a rectangular protrusion 33*c* on the bottom surface 33*b*.

As shown in FIGS. 39A to 39C, the first bottom cover 35 includes a rectangular bottom board 35*a* and a frame-shaped protrusion surrounding the bottom board 35*a*, and the second bottom cover 36 includes a rectangular bottom board 36*a* and a frame-shaped protrusion surrounding the bottom board 36*a*. When placed on the bottom surface 33*b* of the cell culture plate 33, the first bottom cover 35 can accommodate the rectangular protrusion 33*c* inside. When placed on the first bottom cover 35, the second bottom cover 36 can accommodate a rectangular protrusion 35*b* inside. The bottom board 35*a* in the first bottom cover 35 has twelve (3 columns by 4 rows) circular through-holes 35*c* serving as the inner walls of the cell culture chambers and having the inner diameter equal to that of the through-holes 33*d* in portions corresponding to the twelve through-holes 33*d* when the bottom board 35*a* is placed on the bottom surface 33*b* of the cell culture plate 33.

The cell culture plate 33 having the through-holes 33*d* serving as the inner walls of the cell culture chambers is used as the cell culture chamber described below, together with the first bottom cover 35 having the multiple through-holes 35*c* serving as the inner walls of the cell culture chambers.

A cell culture method according to one or more embodiments of the present invention for fabricating three-layer BBB models including a vascular endothelial cell, a pericyte, and an astrocyte using a cell culture device according to the present embodiment will now be described with reference to FIGS. 40 to 42C.

Figure 40:
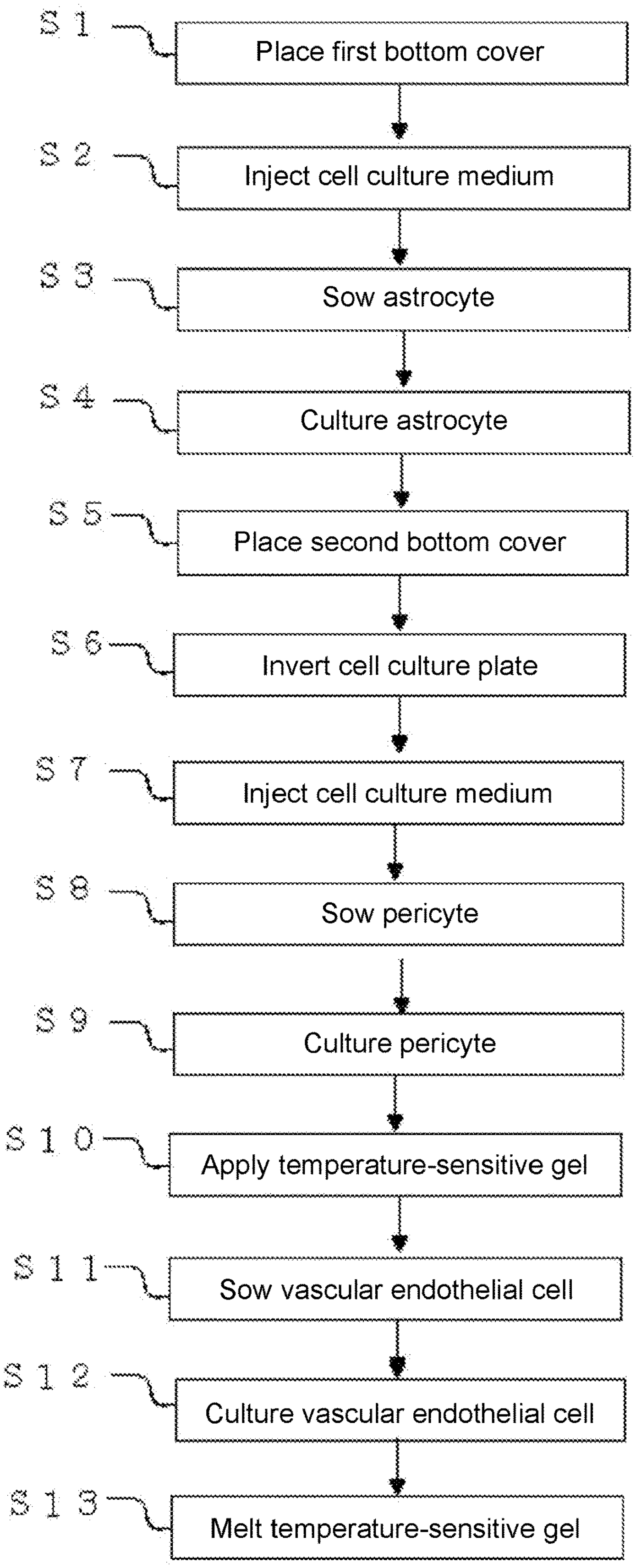
FIG. 40 is a flowchart of a cell culture method according to a sixth embodiment of the present invention.
Figure 41A:
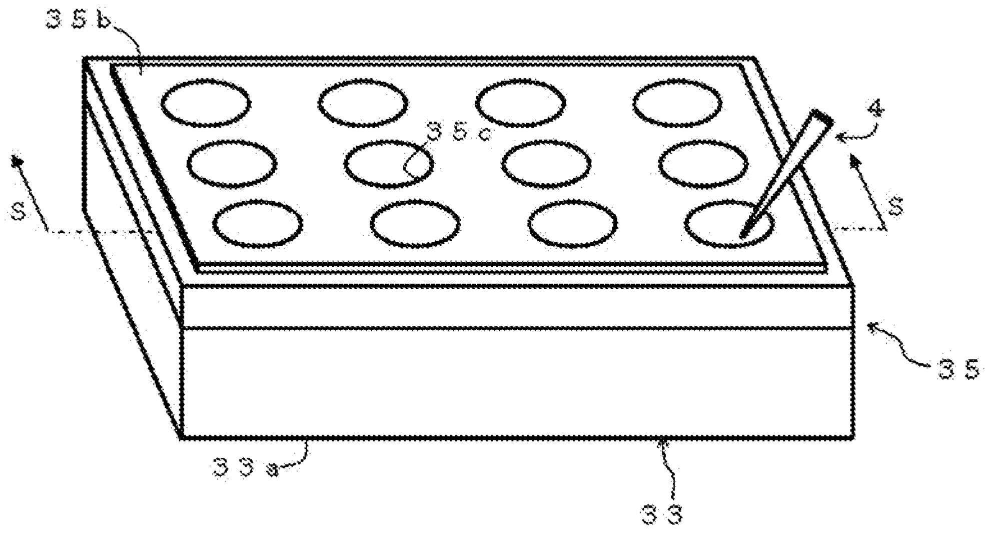
FIG. 41A is a diagram of an inverted cell culture plate to which a first bottom cover is attached.
Figure 41B:
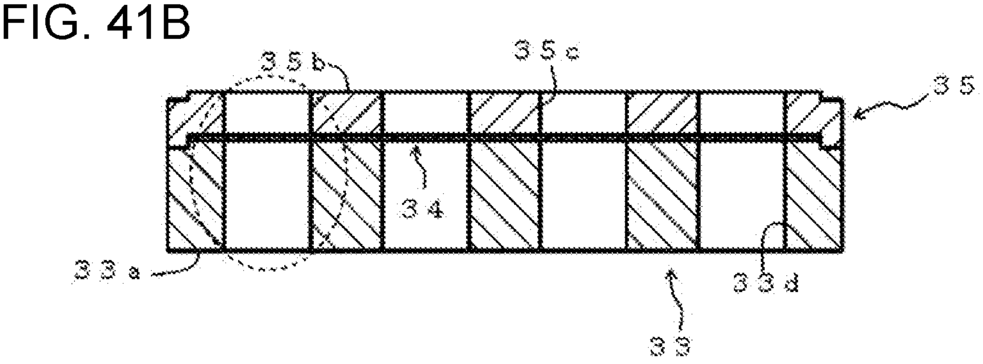
FIG. 41B is a cross-sectional view taken along line S-S as viewed in the direction indicated by arrows in FIG. 41A.
Figure 41C:
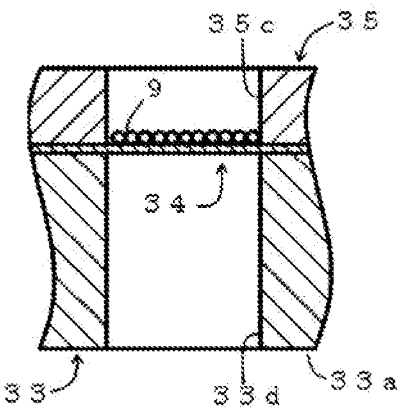
FIG. 41C is an enlarged view of a portion encircled with the dotted line in FIG. 41B.
Figure 42A:
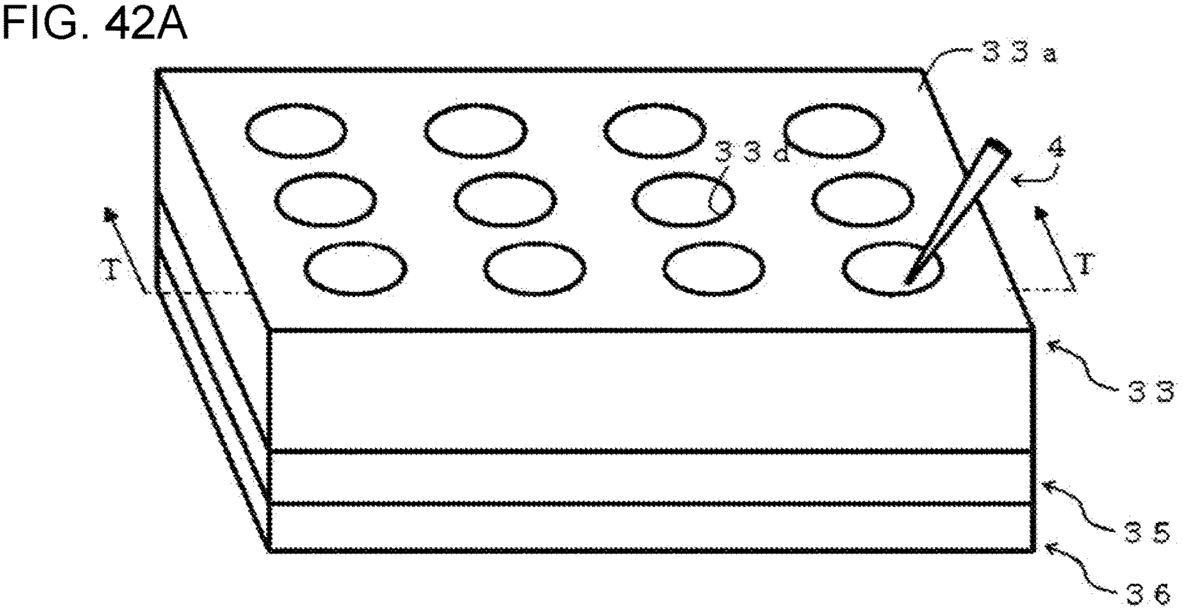
FIG. 42A is a diagram of the inverted cell culture plate and the first bottom cover shown in FIG. 41A to which the second bottom cover is attached.
Figure 42B:
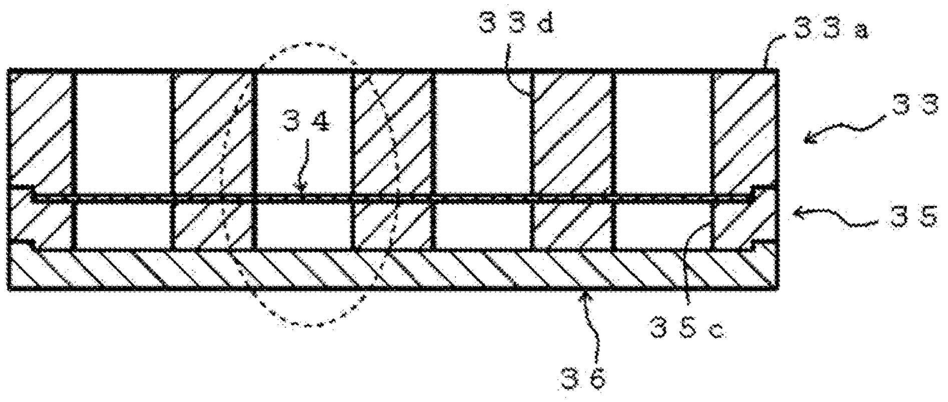
FIG. 42B is a cross-sectional view taken along line T-T as viewed in the direction indicated by arrows in FIG. 42A.
Figure 42C:
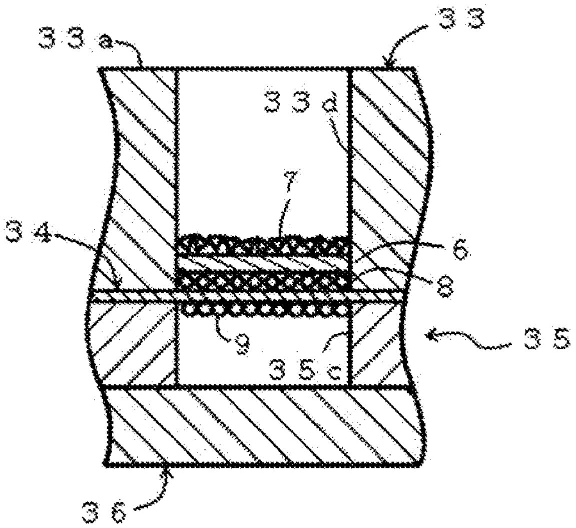
FIG. 42C is an enlarged view of a portion encircled with the dotted line in FIG. 42B.

FIG. 40 is a flowchart of a cell culture method according to the sixth embodiment of the present invention. FIG. 41A is a diagram of an inverted cell culture plate to which the first bottom cover is attached. FIG. 41B is a cross-sectional view taken along line S-S as viewed in the direction indicated by arrows in FIG. 41A. FIG. 41C is an enlarged view of a portion encircled with the dotted line in FIG. 41B. FIG. 42A is a diagram of the inverted cell culture plate and the first bottom cover shown in FIG. 41A to which the second bottom cover is attached. FIG. 42B is a cross-sectional view taken along line T-T as viewed in the direction indicated by arrows in FIG. 42A. FIG. 42C is an enlarged view of a portion encircled with the dotted line in FIG. 42B.

First, as shown in FIGS. 41A and 41B, the first bottom cover 35 is placed on the bottom surface 33*b* of the inverted cell culture plate 33 (step S1 in FIG. 40). Subsequently, as shown in FIG. 41A, a cell culture medium (not shown) is injected into the through-holes 35*c* in the first bottom cover 35 using the pipette 4 and seeded with the astrocyte 9 (steps S2 and S3 in FIG. 40). The astrocyte 9 in FIG. 41C is then cultured for several days until forming into a layer (step S4 in FIG. 40) with the temperature inside the through-holes 35*c* maintained at, for example, 33° C.

The second bottom cover 36 is then placed on the first bottom cover 35, and the cell culture plate 33 integral with the first bottom cover 35 and the second bottom cover 36 is inverted (steps S5 and S6 in FIG. 40). The cell culture medium (not shown) is then injected into the through-holes 33*d* in the cell culture plate 33 using the pipette 4 as shown in FIG. 42A and seeded with the pericyte 8 (steps S7 and S8 in FIG. 40).

The pericyte 8 is then cultured for several days until forming into a layer with the temperature inside the through-holes 33*d* in the cell culture plate 33 maintained at, for example, 33° C. The cell culture medium is removed after the pericyte 8 is grown into a layer (step S9 in FIG. 40). Thus, the astrocyte 9 that has grown into a layer on the outer surface of the porous membrane 3 has cell projections extending through pores in the porous membrane 3 to a position near the pericyte 8 on the inner surface of the porous membrane 3.

When the insides of the through-holes 33*d* in the cell culture plate 33 and the through-holes 35*c* in the first bottom cover 35 are used as cell culture chambers and the first bottom cover 35 is placed on the cell culture plate 33, each cell culture chamber is partitioned into two by one porous membrane 3. In the cell culture device according to the present embodiment, the inner walls of each through-hole 33*d* in the cell culture plate 33 and the corresponding through-hole 35*c* in the first bottom cover 35 thus define a pair of upper and lower cell culture chambers divided by the porous membrane 3. Multiple upper cell culture chambers are integrally coupled together, and lower cell culture chambers are integrally coupled together.

Subsequently, the temperature-sensitive gel 6 that melts at or over a temperature (e.g., 37° C.) at which the vascular endothelial cell stops growing is applied to the cell layer of the pericyte 8 (step S10 in FIG. 40). In addition, the vascular endothelial cell 7 is embedded in the temperature-sensitive gel 6 (step S11 in FIG. 40). The vascular endothelial cell 7 is then cultured for several days with the temperature inside the through-holes 33*d* in the cell culture plate 33 maintained at, for example, 33° C. (step S12 in FIG. 40).

Thus, as shown in FIG. 42C, three cell layers including the vascular endothelial cell 7 embedded in the temperature-sensitive gel 6, the pericyte 8, and the astrocyte 9 are formed at the bottom of the cell culture insert 32. When the temperature inside the through-holes 33*d* in the cell culture plate 33 is raised to 37° C., the vascular endothelial cell 7 stops growing, and the temperature-sensitive gel 6 melts (step S12 in FIG. 40). Thus, the vascular endothelial cell 7 comes into contact with the pericyte 8. In this state, the temperature inside the through-holes 33*d* in the cell culture plate 33 is maintained at 33° C. to restart culture of the vascular endothelial cell 7. This completes a three-layer BBB model including the vascular endothelial cell 7, the pericyte 8, and the astrocyte 9.

In the cell culture device according to the present embodiment, the first bottom cover 35 is placed on the bottom surface 33*b* with the cell culture plate 33 inverted, and the astrocyte 9 is sown into the through-holes 35*c* with the cell culture medium 5. The inner walls of the through-holes 35*c* then prevent leakage of the cell culture medium 5 and the astrocyte 9. The cell culture device according to the present embodiment thus facilitates culture of the astrocyte 9 on the outer surface of the porous membrane 3. In addition, when the second bottom cover 36 is placed on the first bottom cover 35, the cell culture plate 33 is inverted together with the first bottom cover 35 and the second bottom cover 36. The pericyte 8 and the vascular endothelial cell 7 are then sown with the cell culture medium 5 into the through-holes 33*d* in the cell culture plate 33. The inner walls of the through-holes 33*d* then prevent leakage of the cell culture medium 5, the pericyte 8, and the vascular endothelial cell 7. The cell culture device according to the present embodiment thus facilitates culture of the pericyte 8 and the vascular endothelial cell 7 on the inner surface of the porous membrane 3. In addition, the cell culture plate 33 with the first bottom cover 35 and the second bottom cover 36 functions as the microplate 2.

The cell culture device according to the present embodiment eliminates the cell culture insert and allows use of the cell culture plate 33 as the microplate 2. Thus, the cell culture device can enhance mass production of three-layer BBB models including the vascular endothelial cell 7, the pericyte 8, and the astrocyte 9, compared with a cell culture device that involves use of the cell culture inserts and the microplates 2.

The cell culture method according to the present embodiment includes a process of applying the temperature-sensitive gel 6 to the cell layer of the pericyte 8. This method eliminates preparation of the cell sheet 20 of the vascular endothelial cell 7 and thus eliminates the process of fabricating the cell sheet. The above cell culture method can further enhance mass production of the above BBB model.

INDUSTRIAL APPLICABILITY

The cell culture method and the cell culture device used with the cell culture method according to the present invention are applicable to mass production of three-layer BBB models including a vascular endothelial cell, a pericyte, and an astrocyte.

REFERENCE SIGNS LIST

1 cell culture insert
1*a* side surface
1*b* large-diameter opening
1*c* small-diameter opening
1*d* flange
1*e* fourth inner wall
2 microplate
2*a* upper surface
2*b* well
2*c* bottom surface
3 porous membrane
4 pipette
5 cell culture medium
6 temperature-sensitive gel
7 vascular endothelial cell
8 pericyte

9 astrocyte
10 insert holding plate
10*a* side plate
10*b* bottom board
10*c* angular hole
10*d* circular hole
11 cell culture case
11*a* bottom board
11*b* through-hole
12 insert retainer
12*a* square bar
12*b* coupler
13 case lid
13*a* recess
13*b* protrusion
14 plate
14*a* base
14*b* first annular protrusion
14*c* second annular protrusion
14*d* through-hole
15 plate cover
15*a* base
15*b* holder
16 spacer
16*a* base
16*b* holder
16*c* cylinder
16*d* distal end face
17 pusher
17*a* push plate
17*b* holder
17*c* push portion
17*d* distal end face
18 membrane holder
18*a* engageable portion
18*b* third inner wall
19 insert body
19*a* flange
19*b* taper
20 cell sheet
21 cell culture insert
22 plate
22*a* base
22*b* through-hole
22*c* cylinder
23 plate cover
23*a* base
23*b* circular protrusion
24 spacer cover
24*a* base
24*b* circular protrusion
25 spacer
25*a* base
25*b* through-hole
25*c* cylinder
26 pusher
26*a* push plate
26*b* push portion
26*c* distal end face
27 membrane holder
27*a* flange
28 sleeve
28*a* flange
29 cell culture plate
29*a* upper surface
29*b* lower surface
29*c* first rectangular protrusion
29*d* second rectangular protrusion
29*e* through-hole
29*f* large-diameter portion
29*g* small-diameter portion
30 first plate cover
30*a* recess
30*b* protrusion
31 second plate cover
31*a* recess
31*b* protrusion
32 cell culture insert
32*a* flange
32*b* first inner wall
33 cell culture plate
33*a* upper surface
33*b* bottom surface
33*c* rectangular protrusion
33*d* through-hole
34 sheet
35 first bottom cover
35*a* bottom board
35*b* rectangular protrusion
35*c* through-hole
36 second bottom cover
36*a* bottom board

The invention claimed is:

1. A cell culture device comprising:

a plurality of cell culture chambers, each of the plurality comprising a pair consisting of an upper cell culture chamber and a lower cell culture chamber, the pair being defined by a tubular inner wall divided by a porous membrane (3), the porous membrane (3) having two surfaces to which a living organism material is to be fixed, the upper cell culture chambers being coupled and integrated with each other, and the lower cell culture chambers being coupled and integrated with each other;

a cell culture plate (33) having a plurality of first through-holes (33*d*), each through-hole having an inner circumferential surface that forms the inner wall, and a bottom surface (33*b*) receiving a sheet (34) including the porous membrane (3) to cover the plurality of first through-holes (33*d*);

a first bottom cover (35) placeable on the bottom surface (33*b*) of the cell culture plate (33), the first bottom cover (35) including an open top and a bottom board (35*a*), the bottom board (35*a*) having a plurality of second through-holes (35*c*), each through-hole having an inner circumferential surface that forms the inner wall together with a corresponding first through-hole (33*d*) of the plurality of first through-holes (33*d*); and a second bottom cover (36) being the cell culture chamber cover, the second bottom cover (36) being placeable on the bottom board (35*a*) in the first bottom cover (35), wherein the plurality of second through-holes (35*c*) align with the plurality of first through-holes (33*d*) in a plan view of the first bottom cover (35) placed on the bottom surface (33*b*) of the cell culture plate (33).

2. A cell culture device comprising:

a plurality of cell culture chambers, each of the plurality comprising a pair consisting of an upper cell culture chamber and a lower cell culture chamber, the pair being defined by a tubular inner wall divided by a porous membrane (3), the porous membrane (3) having two surfaces to which a living organism material is to be fixed, the upper cell culture chambers being coupled and integrated with each other, and the lower cell culture chambers being coupled and integrated with each other;

a membrane holder (27) including a second inner wall (27*b*) having one end closed by the porous membrane (3), the second inner wall (27*b*) being the inner wall, the membrane holder (27) being one of the plurality of pairs of upper cell culture chambers and lower cell culture chambers;

a plate (22) including a planar first base (22*a*), a plurality of first through-holes (22*b*) in the planar first base (22*a*), and a plurality of first cylinders (22*c*) extending perpendicularly to one surface of the planar first base (22*a*), the plurality of first cylinders (22*c*) being continuous with the plurality of first through-holes (22*b*) and receiving the membrane holder (27) inside, the plurality of first cylinders (22*c*) each being the inner wall together with a corresponding first through-hole (22*b*) of the plurality of first through-holes (22*b*);

a plate cover (23) including a planar second base (23*a*) and a plurality of first protrusions (23*b*) on one surface of the planar second base (23*a*) to simultaneously fit into the plurality of first cylinders (22*c*), the plate cover (23) being the cell culture chamber cover to cover the plurality of first through-holes (22*b*) each receiving the membrane holder (27) inside;

a spacer cover (24) including a planar third base (24*a*) and a plurality of second protrusions (24*b*) on one surface of the planar third base (24*a*) to simultaneously fit into the plurality of first cylinders (22*c*), the spacer cover (24) being the cell culture chamber cover to cover the plurality of first through-holes (22*b*) each receiving the membrane holder (27) inside;

a spacer (25) including a planar fourth base (25*a*) and a plurality of second through-holes (25*b*) in the planar fourth base (25*a*), the plurality of second through-holes (25*b*) being as many as the plurality of first through-holes (22*b*), the plurality of second through-holes (25*b*) each being the inner wall, the spacer (25) including a plurality of second cylinders (25*c*) extending continuously with the plurality of second through-holes (25*b*) and perpendicularly to one surface of the planar fourth base (25*a*), the plurality of second cylinders (25*c*) defining the upper cell culture chambers and the lower cell culture chambers together with the plurality of first cylinders (22*c*), being simultaneously receivable in the plurality of first cylinders (22*c*), and each being the inner wall together with a corresponding second through-hole (25*b*) of the plurality of second through-holes (25*b*); and a pusher (26) including a planar push plate (26*a*) and a plurality of push portions (26*b*) extending perpendicularly to one surface of the planar push plate (26*a*) to be simultaneously received in the plurality of first through-holes (22*b*).

3. A cell culture device comprising:

a plurality of cell culture chambers, each of the plurality comprising a pair consisting of an upper cell culture chamber and a lower cell culture chamber, the pair being defined by a tubular inner wall divided by a porous membrane (3), the porous membrane (3) having two surfaces to which a living organism material is to be fixed, the upper cell culture chambers being coupled and integrated with each other, and the lower cell culture chambers being coupled and integrated with each other;

a membrane holder (18) including a third inner wall (18*b*) having one end closed by the porous membrane (3), the third inner wall (18*b*) being the inner wall, the membrane holder (18) being one of the plurality of pairs of upper cell culture chambers and lower cell culture chambers;

a plate (14) including a planar base (14*a*) and a plurality of through-holes (14*d*) in the planar base (14*a*), and the plurality of through-holes (14*d*) each receiving the membrane holder (18) inside and being the inner wall of each of the upper cell culture chambers and the lower cell culture chambers, the plate (14) being one of the plurality of pairs of upper cell culture chambers and lower cell culture chambers;

two planar plate covers (15) placeable on the plate (14) to cover the plurality of through-holes (14*d*) each receiving the membrane holder (18) inside, the two planar plate covers (15) each being the cell culture chamber cover; and a pusher (17) including a planar push plate (17*a*) and a plurality of push portions (17*c*) extending perpendicularly to one surface of the planar push plate (17*a*) to be simultaneously received in the plurality of through-holes (14*d*).

4. The cell culture device according to claim 3, wherein the plate (14) includes, on two surfaces of the planar base (14*a*), a plurality of first protrusions (14*b*) and a plurality of second protrusions (14*c*) being continuous with the plurality of through-holes (14*d*) and surrounding the plurality of through-holes (14*d*) in a plan view of the planar base (14*a*), the two plate covers (15) each include, on one surface of the plate cover (15), a plurality of first cylinders (15*b*) to simultaneously fit to the plurality of first protrusions (14*b*) or the plurality of second protrusions (14*c*), and the pusher (17) includes a plurality of second cylinders (17*b*) shorter than the plurality of push portions (17*c*) on one surface of the push plate (17*a*), the plurality of second cylinders (17*b*) surround the plurality of push portions (17*c*), and the plurality of second cylinders (17*b*) simultaneously fit to the plurality of first protrusions (14*b*) and the plurality of second protrusions (14*c*).

5. A cell culture device comprising:

a plurality of cell culture chambers, each of the plurality comprising a pair consisting of an upper cell culture chamber and a lower cell culture chamber, the pair being defined by a tubular inner wall divided by a porous membrane (3), the porous membrane (3) having two surfaces to which a living organism material is to be fixed, the upper cell culture chambers being coupled and integrated with each other, and the lower cell culture chambers being coupled and integrated with each other;

a plurality of cell culture inserts (1) each including a fourth inner wall (1*e*) having one end closed by the porous membrane (3), the fourth inner wall (1*e*) being the inner wall, the plurality of cell culture inserts (1) being the upper cell culture chambers and the lower cell culture chambers;

a cell culture case (11) including an open top and a bottom board (11*a*), the bottom board (11*a*) having a plurality of through-holes (11*b*) each being the inner wall and receiving the plurality of cell culture inserts (1), the cell culture case (11) including the upper cell culture chambers and the lower cell culture chambers;

an insert holder (10, 12) configured to hold the plurality of cell culture inserts (1) while allowing the plurality of cell culture inserts (1) to be simultaneously received in the plurality of through-holes (11*b*) in cell culture case (11); and a case lid (13) configured to cover the open top of the cell culture case (11), the case lid (13) being the cell culture chamber cover.

6. A cell culture method for fabricating a three layer blood brain barrier in vitro model including a vascular endothelial cell, a pericyte, and an astrocyte performed with a cell culture device comprising:

a plurality of cell culture chambers, each of the plurality comprising a pair consisting of an upper cell culture chamber and a lower cell culture chamber, the pair being defined by a tubular inner wall divided by a porous membrane (3), the porous membrane (3) having two surfaces to which a living organism material is to be fixed, the upper cell culture chambers being coupled and integrated with each other, and the lower cell culture chambers being coupled and integrated with each other; and a cell culture plate (33) having a plurality of first through-holes (33*d*), each through-hole having an inner circumferential surface that forms the inner wall, the porous membrane (3) covering the plurality of first through-holes (33*d*);

the method comprising:

seeding, with the astrocyte, a first surface of the two surfaces of the porous membrane (3) facing upward;

culturing the astrocyte;

simultaneously closing upper end openings of the plurality of pairs of upper cell culture chambers and lower cell culture chambers;

simultaneously inverting the plurality of pairs of upper cell culture chambers and lower cell culture chambers to seed a second surface of the two surfaces of the porous membrane (3) with the pericyte;

culturing the pericyte;

laying a sheet of the vascular endothelial cell on the second surface of the porous membrane (3);

and culturing the vascular endothelial cell.

7. The cell culture method according to claim 6, wherein the vascular endothelial cell is temperature sensitive and stops growing at a temperature, and the cell culture method includes, instead of laying the sheet of the vascular endothelial cell on the second surface of the porous membrane (3), seeding the second surface of the porous membrane (3) with the vascular endothelial cell embedded in a temperature-sensitive gel, and melting the temperature-sensitive gel after culturing the vascular endothelial cell.

* * * * *